US010125172B2

(12) United States Patent
Marshall et al.

(10) Patent No.: US 10,125,172 B2
(45) Date of Patent: Nov. 13, 2018

(54) CONFORMATIONALLY STABILIZED RSV PRE-FUSION F PROTEINS

(71) Applicants: CALDER BIOSCIENCES INC., New York, NY (US); The United States of America as Represented by the Secretary Department of Health and Human Services, Washington, DC (US)

(72) Inventors: Christopher Patrick Marshall, New York, NY (US); Jason Scott McLellan, Norwich, VT (US); Peter Joseph Alff, New York, NY (US); Claudio Bertuccioli, New York, NY (US); Roberto Mariani, San Diego, CA (US)

(73) Assignees: CALDER BIOSCIENCES INC., New York, NY (US); THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 145 days.

(21) Appl. No.: 14/340,519

(22) Filed: Jul. 24, 2014

(65) Prior Publication Data

US 2015/0030622 A1 Jan. 29, 2015

Related U.S. Application Data

(60) Provisional application No. 61/858,533, filed on Jul. 25, 2013.

(51) Int. Cl.

| | |
|---|---|
| ***C07K 14/005*** | (2006.01) |
| ***A61K 39/155*** | (2006.01) |
| ***A61K 39/12*** | (2006.01) |
| *A61K 39/00* | (2006.01) |

(52) U.S. Cl.

CPC ............ *C07K 14/005* (2013.01); *A61K 39/12* (2013.01); *A61K 39/155* (2013.01); *A61K 2039/525* (2013.01); *C12N 2760/18534* (2013.01)

(58) Field of Classification Search

None

See application file for complete search history.

(56) References Cited

U.S. PATENT DOCUMENTS

| | | | |
|---|---|---|---|
| 7,037,894 | B2 | 5/2006 | Marshall |
| 2005/0054572 | A1 | 3/2005 | Marshall |
| 2007/0184518 | A1 | 8/2007 | Marshall |
| 2011/0123556 | A1 | 5/2011 | Phogat |
| 2013/0236905 | A1 | 9/2013 | Marshall |
| 2013/0317205 | A1 | 11/2013 | Marshall |
| 2015/0030622 | A1 | 1/2015 | Marshall |
| 2015/0056233 | A1 | 2/2015 | Marshall |
| 2016/0046675 | A1 | 2/2016 | Kwong |

FOREIGN PATENT DOCUMENTS

| | | | |
|---|---|---|---|
| WO | 2001029247 | A1 | 4/2001 |
| WO | 2012158613 | A1 | 11/2012 |
| WO | 2015013551 | A1 | 1/2015 |
| WO | 2015020913 | A2 | 2/2015 |

OTHER PUBLICATIONS

Weisshaar et al. DNA and Cell Biology 2015, vol. 34, pp. 505-510.*
Murphy et al. Virus Research 1994 vol. 32, pp. 13-26.*
McClellan et al (Science vol. 340, p. 1114, col. 2 upper part, 2013.*
McClellan et al (Science vol. 342, p. 592ff, 2013.*
International Search Report for PCT/US2014/048086 dated Sep. 19, 2014.
Written Opinion for PCT/US2014/048086 dated Sep. 19, 2014.
International Preliminary Report of Patentability for PCT/US2014/048086 dated Jan. 26, 2016.
"Dityrosine Locked Prefusion F Protein: A Path to a Protective RSV Vaccine." SBIR Source, Jun. 1, 2014.
McLellan. "Structure of RSV Fusion Glycoprotein Trimer Bound to a Prefusion-Specific Neutralizing Antibody" Science. vol. 340, pp. 1113-1117. Apr. 25, 2013 (Apr. 25, 2013).
Magro "Neutralizing antibodies against the preactive form of respiratory syncytial virus fusion protein offer unique possibilities for clinical intervention." Proceedings of The National Academy of Sciences, vol. 109, No. 8, pp. 3089-3094, Feb. 21, 2012 (Feb. 21, 2012).
McLellan "Structure-Based Design of a Fusion Glycoprotein Vaccine for Respiratory Syncytial Virus." Science, vol. 342, No. 6158, pp. 592-598, Oct. 31, 2013 (Oct. 31, 2013).
Costello "Targeting RSV with Vaccines and Small Molecule Drugs." Infectious Disorders Drug Targets, vol. 12, pp. 110-128 (Apr. 2012).
Krarup "A highly stable prefusion RSV F vaccine derived from structural analysis of the fusion mechanism." Nat. Commun. vol. 6: p. 8143 (Sep. 2015).
Dey et al., "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, (2007), vol. 81, No. 11, pp. 5579-5593.

* cited by examiner

*Primary Examiner* — Shanon A. Foley
*Assistant Examiner* — Myron G Hill
(74) *Attorney, Agent, or Firm* — Grimes & Yvon LLP

(57) ABSTRACT

In some embodiments, the present invention provides respiratory syncytial virus (RSV) F proteins, polypeptides and protein complexes that comprise one or more cross-links to stabilize the protein, polypeptide or protein complex in its pre-fusion conformation. In some embodiments the present invention provides RSV F proteins, polypeptides and protein complexes comprising one or more mutations to facilitate such cross-linking. In some embodiments the present invention provides compositions comprising such proteins, polypeptides or protein complexes, including vaccine compositions, and methods of making and using the same.

15 Claims, 31 Drawing Sheets

Specification includes a Sequence Listing.

>RSV_F_WT subtype A soluble

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:1)

Fig. 1A

>WT_RSV-F_full_length_subtype(A) (Accession# AHL84194)

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:2)

Fig. 1B

```
>WT_RSV-F_soluble_subtype(B)

MELLIHRSSAIFLTLAINALYLTSSQNITEEFYQSTCSAVSRGYFSALRTGWYTSVITIELSNITETKCN
GTDTKVKLIKQELDKYKNAVTELQLLMQNTPAANNRARREAPQHMNYTINTTKNLNVSISKKRKRRFLGF
LLGVGSAIASGIAVSKVLHLEGEVNKIKNALLSTNKAVVSLSNGVSVLTSKVLDLKNYINNQLLPIVNQQ
SCRIFNIETVIEFQQKNSRLLEITREFSVNAGVTTPLSTYMLTNSELLSLINDMPITNDQKKLMSSNVQI
VRQQSYSIMSIIKEEVLAYVVQLPIYGVIDTPCWKLHTSPLCTTNIKEGSNICLTRTDRGWYCDNAGSVS
FFPQADTCKVQSNRVFCDTMNSLTLPSEVSLCNTDIFNSKYDCKIMTSKTDISSSVITSLGAIVSCYGKT
KCTASNKNRGIIKTFSNGCDYVSNKGVDTVSVGNTLYYVNKLEGKNLYVKGEPIINYYDPLVFPSDEFDA
SISQVNEKINQSLAFIRKSDELLSAIGGYIPEAPRDGQAYVRKDGEWVLLSTFLGGLVPRGSHHHHHHSA
WSHPQFEK (SEQ ID NO:3)
```

Fig. 2A

```
>WT_RSV_F_Subtype(B) full-length (Accession# AHJ60043.1)

MELLIHRSSAIFLTLAINALYLTSSQNITEEFYQSTCSAVSRGYFSALRTGWYTSVITIELSNITETKCN
GTDTKVKLIKQELDKYKNAVTELQLLMQNTPAANNRARREAPQHMNYTINTTKNLNVSISKKRKRRFLGF
LLGVGSAIASGIAVSKVLHLEGEVNKIKNALLSTNKAVVSLSNGVSVLTSKVLDLKNYINNQLLPIVNQQ
SCRIFNIETVIEFQQKNSRLLEITREFSVNAGVTTPLSTYMLTNSELLSLINDMPITNDQKKLMSSNVQI
VRQQSYSIMSIIKEEVLAYVVQLPIYGVIDTPCWKLHTSPLCTTNIKEGSNICLTRTDRGWYCDNAGSVS
FFPQADTCKVQSNRVFCDTMNSLTLPSEVSLCNTDIFNSKYDCKIMTSKTDISSSVITSLGAIVSCYGKT
KCTASNKNRGIIKTFSNGCDYVSNKGVDTVSVGNTLYYVNKLEGKNLYVKGEPIINYYDPLVFPSDEFDA
SISQVNEKINQSLAFIRKSDELLHNVNTGKSTTNIMITTIIIVIIVVLLSLIAIGLLLYCKAKNTPVTLS
KDQLSGINNIAFSK (SEQ ID NO:4)
```

Fig. 2B

>DS-Cav1 soluble
MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:5)

Fig. 3A

>DS_Cav1_full_length

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:6)

Fig. 3B

>Cav1_soluble

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:7)

Fig. 4A

>Cav1_full_length

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:8)

Fig. 4B

>DS_soluble

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:9)

Fig. 5A

>DS_full_length

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNTGKSTTNIMITTIIIVIIVVLL
SLIAIGLLLYCKAKNTPVTLSKDQLSGINNIAFSK (SEQ ID NO:10)

Fig. 5B

```
CLUSTAL 2.1 multiple sequence alignment

RSV_F_subtype_B_      MELLIHRSSAIFLTLAINALYLTSSQNITEEFYQSTCSAVSRGYFSALRTGWYTSVITIE 60
RSV_F_WT              MELLILKANAITTILTAVTFCFASGQNITEEFYQSTCSAVSKGYLSALRTGWYTSVITIE 60
                      ***** ::.**   *:  :: ::*.***************:**:**************

RSV_F_subtype_B_      LSNITETKCNGTDTKVKLIKQELDKYKNAVTELQLLMQNTPAANNRARREAPQHMNYTIN 120
RSV_F_WT              LSNIKENKCNGTDAKVKLIKQELDKYKNAVTELQLLMQSTPATNNRARRELPRFMNYTLN 120
                      ****.*.******:*********************.***:******* *:.****:*

RSV_F_subtype_B_      TTKNLNVSISKKRKRRFLGFLLGVGSAIASGIAVSKVLHLEGEVNKIKNALLSTNKAVVS 180
RSV_F_WT              NAKKTNVTLSKKRKRRFLGFLLGVGSAIASGVAVSKVLHLEGEVNKIKSALLSTNKAVVS 180
                      .:*: **::**********************:****************.***********

RSV_F_subtype_B_      LSNGVSVLTSKVLDLKNYINNQLLPIVNQQSCRIFNIETVIEFQQKNSRLLEITREFSVN 240
RSV_F_WT              LSNGVSVLTSKVLDLKNYIDKQLLPIVNKQSCSISNIETVIEFQQKNNRLLEITREFSVN 240
                      *******************::*******:*** * ***************.************

RSV_F_subtype_B_      AGVTTPLSTYMLTNSELLSLINDMPITNDQKKLMSSNVQIVRQQSYSIMSIIKEEVLAYV 300
RSV_F_WT              AGVTTPVSTYMLTNSELLSLINDMPITNDQKKLMSNNVQIVRQQSYSIMSIIKEEVLAYV 300
                      ******:****************************.************************

RSV_F_subtype_B_      VQLPIYGVIDTPCWKLHTSPLCTTNIKEGSNICLTRTDRGWYCDNAGSVSFFPQADTCKV 360
RSV_F_WT              VQLPLYGVIDTPCWKLHTSPLCTTNTKEGSNICLTRTDRGWYCDNAGSVSFFPQAETCKV 360
                      ****:******************** *****************************:****

RSV_F_subtype_B_      QSNRVFCDTMNSLTLPSEVSLCNTDIFNSKYDCKIMTSKTDISSSVITSLGAIVSCYGKT 420
RSV_F_WT              QSNRVFCDTMNSLTLPSEVNLCNVDIFNPKYDCKIMTSKTDVSSSVITSLGAIVSCYGKT 420
                      *******************.***.****.************:******************

RSV_F_subtype_B_      KCTASNKNRGIIKTFSNGCDYVSNKGVDTVSVGNTLYYVNKLEGKNLYVKGEPIINYYDP 480
RSV_F_WT              KCTASNKNRGIIKTFSNGCDYVSNKGVDTVSVGNTLYYVNKQEGKSLYVKGEPIINFYDP 480
                      ***************************************** ***.**********:***

RSV_F_subtype_B_      LVFPSDEFDASISQVNEKINQSLAFIRKSDELLHNVN-TGKSTTNIMITTIIIVIIVVLL 539
RSV_F_WT              LVFPSDEFDASISQVNEKINQSLAFIRKSDELLSAIGGYIPEAPRDGQAYVRKDGEWVLL 540
                      *********************************  :.     .:..    : :     ***

RSV_F_subtype_B_      SLIAIGLLLYCKAKNTPVTLSKDQLSGINNIAFSK 574
RSV_F_WT              STFLGGLVPRG-------SHHHHHHSAWSHPQFEK 568
                      * :  **:          :  :.: *. .:  *.*
```

Score: 80.99% identical

Fig. 6

```
CLUSTAL 2.1 multiple sequence alignment

RSV_F_subtypeA      MELLILKANAITTILTAVTFCFASGQNITEEFYQSTCSAVSKGYLSALRTGWYTSVITIE 60
RSV_F_subtypeB      MELLIHRSSAIFLTLAINALYLTSSQNITEEFYQSTCSAVSRGYFSALRTGWYTSVITIE 60
DS_Cav1             MELLILKANAITTILTAVTFCFASGQNITEEFYQSTCSAVSKGYLSALRTGWYTSVITIE 60
                    ***** ::.**   *:  :: ::*.****************:**:***************

RSV_F_subtypeA      LSNIKENKCNGTDAKVKLIKQELDKYKNAVTELQLLMQSTPATNNRARRELPRFMNYTLN 120
RSV_F_subtypeB      LSNITETKCNGTDTKVKLIKQELDKYKNAVTELQLLMQNTPAANNRARREAPQHMNYTIN 120
DS_Cav1             LSNIKENKCNGTDAKVKLIKQELDKYKNAVTELQLLMQSTPATNNRARRELPRFMNYTLN 120
                    ****.*.******:************************.***:******* *:.****:*

RSV_F_subtypeA      NAKKTNVTLSKKRKRRFLGFLLGVGSAIASGVAVCKVLHLEGEVNKIKSALLSTNKAVVS 180
RSV_F_subtypeB      TTKNLNVSISKKRKRRFLGFLLGVGSAIASGIAVSKVLHLEGEVNKIKNALLSTNKAVVS 180
DS_Cav1             NAKKTNVTLSKKRKRRFLGFLLGVGSAIASGVAVCKVLHLEGEVNKIKSALLSTNKAVVS 180
                    .:*: **::**********************:**.*************.***********

RSV_F_subtypeA      LSNGVSVLTFKVLDLKNYIDKQLLPILNKQSCSISNIETVIEFQQKNNRLLEITREFSVN 240
RSV_F_subtypeB      LSNGVSVLTSKVLDLKNYINNQLLPIVNQQSCRIFNIETVIEFQQKNSRLLEITREFSVN 240
DS_Cav1             LSNGVSVLTFKVLDLKNYIDKQLLPILNKQSCSISNIETVIEFQQKNNRLLEITREFSVN 240
                    ********* *********::*****:*:*** * ************.************

RSV_F_subtypeA      AGVTTPVSTYMLTNSELLSLINDMPITNDQKKLMSNNVQIVRQQSYSIMCIIKEEVLAYV 300
RSV_F_subtypeB      AGVTTPLSTYMLTNSELLSLINDMPITNDQKKLMSSNVQIVRQQSYSIMSIIKEEVLAYV 300
DS_Cav1             AGVTTPVSTYMLTNSELLSLINDMPITNDQKKLMSNNVQIVRQQSYSIMCIIKEEVLAYV 300
                    ******:****************************.*************.**********

RSV_F_subtypeA      VQLPLYGVIDTPCWKLHTSPLCTTNTKEGSNICLTRTDRGWYCDNAGSVSFFPQAETCKV 360
RSV_F_subtypeB      VQLPIYGVIDTPCWKLHTSPLCTTNIKEGSNICLTRTDRGWYCDNAGSVSFFPQADTCKV 360
DS_Cav1             VQLPLYGVIDTPCWKLHTSPLCTTNTKEGSNICLTRTDRGWYCDNAGSVSFFPQAETCKV 360
                    ****:******************** *****************************:****

RSV_F_subtypeA      QSNRVFCDTMNSLTLPSEVNLCNVDIFNPKYDCKIMTSKTDVSSSVITSLGAIVSCYGKT 420
RSV_F_subtypeB      QSNRVFCDTMNSLTLPSEVSLCNTDIFNSKYDCKIMTSKTDISSSVITSLGAIVSCYGKT 420
DS_Cav1             QSNRVFCDTMNSLTLPSEVNLCNVDIFNPKYDCKIMTSKTDVSSSVITSLGAIVSCYGKT 420
                    *******************.***.****.************:******************

RSV_F_subtypeA      KCTASNKNRGIIKTFSNGCDYVSNKGVDTVSVGNTLYYVNKQEGKSLYVKGEPIINFYDP 480
RSV_F_subtypeB      KCTASNKNRGIIKTFSNGCDYVSNKGVDTVSVGNTLYYVNKLEGKNLYVKGEPIINYYDP 480
DS_Cav1             KCTASNKNRGIIKTFSNGCDYVSNKGVDTVSVGNTLYYVNKQEGKSLYVKGEPIINFYDP 480
                    ***************************************** ***.**********:***

RSV_F_subtypeA      LVFPSDEFDASISQVNEKINQSLAFIRKSDELLSAIGGYIPEAPRDGQAYVRKDGEWVLL 540
RSV_F_subtypeB      LVFPSDEFDASISQVNEKINQSLAFIRKSDELLHNVN-TGKSTTNIMITTIIIVIIVVLL 539
DS_Cav1             LVFPSDEFDASISQVNEKINQSLAFIRKSDELLSAIGGYIPEAPRDGQAYVRKDGEWVLL 540
                    *********************************  :.    .:..   : :       ***

RSV_F_subtypeA      STFLGGLVPRG--------SHHHHHHSAWSHPQFEK 568
RSV_F_subtypeB      SLIAIGLLLYCKAKNTPVTLSKDQLSGINNIAFSK 574
DS_Cav1             STFLGGLVPRG--------SHHHHHHSAWSHPQFEK 568
                    * :  **:          :  :.: *.  .:   *.*
```

Fig. 7

>RSV_F_A147Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSYIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:11)

Fig. 8

>RSV_F_V220Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETYIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:12)

Fig. 9

>RSV_F_E222Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:13)

Fig. 10

>RSV_F_F223Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEYQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:14)

Fig. 11

>RSV_F_K226Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQYNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:15)

Fig. 12

>RSV_F_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:16)

Fig. 13

>RSV_F_K77Y_E222Y

MELLILKANAITTILTAVTFCFASGQNITEEFYQSTCSAVSKGYLSALRTGWYTSVITIELSNIKENKCNGTDAKVY
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:17)

Fig. 14

>RSV_F_N88Y_S255Y

MELLILKANAITTILTAVTFCFASGQNITEEFYQSTCSAVSKGYLSALRTGWYTSVITIELSNIKENKCNGTDAKVK
LIKQELDKYKYAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNYELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:18)

Fig. 15

>RSV_F_M97Y_H159Y

MELLILKANAITTILTAVTFCFASGQNITEEFYQSTCSAVSKGYLSALRTGWYTSVITIELSNIKENKCNGTDAKVK
LIKQELDKYKNAVTELQLLYQSTPATNNRARRELPRFMNYTLNNAKKTNVTLSKKRKRRFLGFLLGVGSAIASGVAV
SKVLYLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:19)

Fig. 16

>RSV_F_V185Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGYSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:20)

Fig. 17

>RSV_F_V187Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSYLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:21)

Fig. 18

>RSV_F N183Y_K427Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSYGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNYNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:22)

Fig. 19

```
CLUSTAL 2.1 multiple sequence alignment


RSV_F_WT               MELLILKANAITTILTAVTFCFASGQNITEEFYQSTCSAVSKGYLSALRTGWYTSVITIE 60
RSV_F_A147Y            MELLILKANAITTILTAVTFCFASGQNITEEFYQSTCSAVSKGYLSALRTGWYTSVITIE 60
RSV_F_V220Y            MELLILKANAITTILTAVTFCFASGQNITEEFYQSTCSAVSKGYLSALRTGWYTSVITIE 60
RSV_F_E222Y            MELLILKANAITTILTAVTFCFASGQNITEEFYQSTCSAVSKGYLSALRTGWYTSVITIE 60
RSV_F_F223Y            MELLILKANAITTILTAVTFCFASGQNITEEFYQSTCSAVSKGYLSALRTGWYTSVITIE 60
RSV_F_K226Y            MELLILKANAITTILTAVTFCFASGQNITEEFYQSTCSAVSKGYLSALRTGWYTSVITIE 60
RSV_F_V469Y            MELLILKANAITTILTAVTFCFASGQNITEEFYQSTCSAVSKGYLSALRTGWYTSVITIE 60
RSV_F_K77Y_E222Y       MELLILKANAITTILTAVTFCFASGQNITEEFYQSTCSAVSKGYLSALRTGWYTSVITIE 60
RSV_F_N88Y_S255Y       MELLILKANAITTILTAVTFCFASGQNITEEFYQSTCSAVSKGYLSALRTGWYTSVITIE 60
RSV_F_M97Y_H159Y       MELLILKANAITTILTAVTFCFASGQNITEEFYQSTCSAVSKGYLSALRTGWYTSVITIE 60
RSV_F_V185Y_K427Y      MELLILKANAITTILTAVTFCFASGQNITEEFYQSTCSAVSKGYLSALRTGWYTSVITIE 60
RSV_F_V187Y_K427Y      MELLILKANAITTILTAVTFCFASGQNITEEFYQSTCSAVSKGYLSALRTGWYTSVITIE 60
                       ************************************************************

RSV_F_WT               LSNIKENKCNGTDAKVKLIKQELDKYKNAVTELQLLMQSTPATNNRARRELPRFMNYTLN 120
RSV_F_A147Y            LSNIKENKCNGTDAKVKLIKQELDKYKNAVTELQLLMQSTPATNNRARRELPRFMNYTLN 120
RSV_F_V220Y            LSNIKENKCNGTDAKVKLIKQELDKYKNAVTELQLLMQSTPATNNRARRELPRFMNYTLN 120
RSV_F_E222Y            LSNIKENKCNGTDAKVKLIKQELDKYKNAVTELQLLMQSTPATNNRARRELPRFMNYTLN 120
RSV_F_F223Y            LSNIKENKCNGTDAKVKLIKQELDKYKNAVTELQLLMQSTPATNNRARRELPRFMNYTLN 120
RSV_F_K226Y            LSNIKENKCNGTDAKVKLIKQELDKYKNAVTELQLLMQSTPATNNRARRELPRFMNYTLN 120
RSV_F_V469Y            LSNIKENKCNGTDAKVKLIKQELDKYKNAVTELQLLMQSTPATNNRARRELPRFMNYTLN 120
RSV_F_K77Y_E222Y       LSNIKENKCNGTDAKVYLIKQELDKYKNAVTELQLLMQSTPATNNRARRELPRFMNYTLN 120
RSV_F_N88Y_S255Y       LSNIKENKCNGTDAKVKLIKQELDKYKYAVTELQLLMQSTPATNNRARRELPRFMNYTLN 120
RSV_F_M97Y_H159Y       LSNIKENKCNGTDAKVKLIKQELDKYKNAVTELQLLYQSTPATNNRARRELPRFMNYTLN 120
RSV_F_V185Y_K427Y      LSNIKENKCNGTDAKVKLIKQELDKYKNAVTELQLLMQSTPATNNRARRELPRFMNYTLN 120
RSV_F_V187Y_K427Y      LSNIKENKCNGTDAKVKLIKQELDKYKNAVTELQLLMQSTPATNNRARRELPRFMNYTLN 120
                       **************** ********** ******** ***********************

RSV_F_WT               NAKKTNVTLSKKRKRRFLGFLLGVGSAIASGVAVSKVLHLEGEVNKIKSALLSTNKAVVS 180
RSV_F_A147Y            NAKKTNVTLSKKRKRRFLGFLLGVGSYIASGVAVSKVLHLEGEVNKIKSALLSTNKAVVS 180
RSV_F_V220Y            NAKKTNVTLSKKRKRRFLGFLLGVGSAIASGVAVSKVLHLEGEVNKIKSALLSTNKAVVS 180
RSV_F_E222Y            NAKKTNVTLSKKRKRRFLGFLLGVGSAIASGVAVSKVLHLEGEVNKIKSALLSTNKAVVS 180
RSV_F_F223Y            NAKKTNVTLSKKRKRRFLGFLLGVGSAIASGVAVSKVLHLEGEVNKIKSALLSTNKAVVS 180
RSV_F_K226Y            NAKKTNVTLSKKRKRRFLGFLLGVGSAIASGVAVSKVLHLEGEVNKIKSALLSTNKAVVS 180
RSV_F_V469Y            NAKKTNVTLSKKRKRRFLGFLLGVGSAIASGVAVSKVLHLEGEVNKIKSALLSTNKAVVS 180
RSV_F_K77Y_E222Y       NAKKTNVTLSKKRKRRFLGFLLGVGSAIASGVAVSKVLHLEGEVNKIKSALLSTNKAVVS 180
RSV_F_N88Y_S255Y       NAKKTNVTLSKKRKRRFLGFLLGVGSAIASGVAVSKVLHLEGEVNKIKSALLSTNKAVVS 180
RSV_F_M97Y_H159Y       NAKKTNVTLSKKRKRRFLGFLLGVGSAIASGVAVSKVLYLEGEVNKIKSALLSTNKAVVS 180
RSV_F_V185Y_K427Y      NAKKTNVTLSKKRKRRFLGFLLGVGSAIASGVAVSKVLHLEGEVNKIKSALLSTNKAVVS 180
RSV_F_V187Y_K427Y      NAKKTNVTLSKKRKRRFLGFLLGVGSAIASGVAVSKVLHLEGEVNKIKSALLSTNKAVVS 180
                       ************************** ***********:*********************

RSV_F_WT               LSNGVSVLTSKVLDLKNYIDKQLLPIVNKQSCSISNIETVIEFQQKNNRLLEITREFSVN 240
RSV_F_A147Y            LSNGVSVLTSKVLDLKNYIDKQLLPIVNKQSCSISNIETVIEFQQKNNRLLEITREFSVN 240
RSV_F_V220Y            LSNGVSVLTSKVLDLKNYIDKQLLPIVNKQSCSISNIETYIEFQQKNNRLLEITREFSVN 240
RSV_F_E222Y            LSNGVSVLTSKVLDLKNYIDKQLLPIVNKQSCSISNIETVIYFQQKNNRLLEITREFSVN 240
RSV_F_F223Y            LSNGVSVLTSKVLDLKNYIDKQLLPIVNKQSCSISNIETVIEYQQKNNRLLEITREFSVN 240
RSV_F_K226Y            LSNGVSVLTSKVLDLKNYIDKQLLPIVNKQSCSISNIETVIEFQQYNNRLLEITREFSVN 240
RSV_F_V469Y            LSNGVSVLTSKVLDLKNYIDKQLLPIVNKQSCSISNIETVIEFQQKNNRLLEITREFSVN 240
RSV_F_K77Y_E222Y       LSNGVSVLTSKVLDLKNYIDKQLLPIVNKQSCSISNIETVIYFQQKNNRLLEITREFSVN 240
RSV_F_N88Y_S255Y       LSNGVSVLTSKVLDLKNYIDKQLLPIVNKQSCSISNIETVIEFQQKNNRLLEITREFSVN 240
RSV_F_M97Y_H159Y       LSNGVSVLTSKVLDLKNYIDKQLLPIVNKQSCSISNIETVIEFQQKNNRLLEITREFSVN 240
RSV_F_V185Y_K427Y      LSNGYSVLTSKVLDLKNYIDKQLLPIVNKQSCSISNIETVIEFQQKNNRLLEITREFSVN 240
RSV_F_V187Y_K427Y      LSNGVSYLTSKVLDLKNYIDKQLLPIVNKQSCSISNIETVIEFQQKNNRLLEITREFSVN 240
                       **** * ******************************** * :** **************
```

Fig. 20A

```
RSV_F_WT              AGVTTPVSTYMLTNSELLSLINDMPITNDQKKLMSNNVQIVRQQSYSIMSIIKEEVLAYV 300
RSV_F_A147Y           AGVTTPVSTYMLTNSELLSLINDMPITNDQKKLMSNNVQIVRQQSYSIMSIIKEEVLAYV 300
RSV_F_V220Y           AGVTTPVSTYMLTNSELLSLINDMPITNDQKKLMSNNVQIVRQQSYSIMSIIKEEVLAYV 300
RSV_F_E222Y           AGVTTPVSTYMLTNSELLSLINDMPITNDQKKLMSNNVQIVRQQSYSIMSIIKEEVLAYV 300
RSV_F_F223Y           AGVTTPVSTYMLTNSELLSLINDMPITNDQKKLMSNNVQIVRQQSYSIMSIIKEEVLAYV 300
RSV_F_K226Y           AGVTTPVSTYMLTNSELLSLINDMPITNDQKKLMSNNVQIVRQQSYSIMSIIKEEVLAYV 300
RSV_F_V469Y           AGVTTPVSTYMLTNSELLSLINDMPITNDQKKLMSNNVQIVRQQSYSIMSIIKEEVLAYV 300
RSV_F_K77Y_E222Y      AGVTTPVSTYMLTNSELLSLINDMPITNDQKKLMSNNVQIVRQQSYSIMSIIKEEVLAYV 300
RSV_F_N88Y_S255Y      AGVTTPVSTYMLTNYELLSLINDMPITNDQKKLMSNNVQIVRQQSYSIMSIIKEEVLAYV 300
RSV_F_M97Y_H159Y      AGVTTPVSTYMLTNSELLSLINDMPITNDQKKLMSNNVQIVRQQSYSIMSIIKEEVLAYV 300
RSV_F_V185Y_K427Y     AGVTTPVSTYMLTNSELLSLINDMPITNDQKKLMSNNVQIVRQQSYSIMSIIKEEVLAYV 300
RSV_F_V187Y_K427Y     AGVTTPVSTYMLTNSELLSLINDMPITNDQKKLMSNNVQIVRQQSYSIMSIIKEEVLAYV 300
                      ************** *********************************************

RSV_F_WT              VQLPLYGVIDTPCWKLHTSPLCTTNTKEGSNICLTRTDRGWYCDNAGSVSFFPQAETCKV 360
RSV_F_A147Y           VQLPLYGVIDTPCWKLHTSPLCTTNTKEGSNICLTRTDRGWYCDNAGSVSFFPQAETCKV 360
RSV_F_V220Y           VQLPLYGVIDTPCWKLHTSPLCTTNTKEGSNICLTRTDRGWYCDNAGSVSFFPQAETCKV 360
RSV_F_E222Y           VQLPLYGVIDTPCWKLHTSPLCTTNTKEGSNICLTRTDRGWYCDNAGSVSFFPQAETCKV 360
RSV_F_F223Y           VQLPLYGVIDTPCWKLHTSPLCTTNTKEGSNICLTRTDRGWYCDNAGSVSFFPQAETCKV 360
RSV_F_K226Y           VQLPLYGVIDTPCWKLHTSPLCTTNTKEGSNICLTRTDRGWYCDNAGSVSFFPQAETCKV 360
RSV_F_V469Y           VQLPLYGVIDTPCWKLHTSPLCTTNTKEGSNICLTRTDRGWYCDNAGSVSFFPQAETCKV 360
RSV_F_K77Y_E222Y      VQLPLYGVIDTPCWKLHTSPLCTTNTKEGSNICLTRTDRGWYCDNAGSVSFFPQAETCKV 360
RSV_F_N88Y_S255Y      VQLPLYGVIDTPCWKLHTSPLCTTNTKEGSNICLTRTDRGWYCDNAGSVSFFPQAETCKV 360
RSV_F_M97Y_H159Y      VQLPLYGVIDTPCWKLHTSPLCTTNTKEGSNICLTRTDRGWYCDNAGSVSFFPQAETCKV 360
RSV_F_V185Y_K427Y     VQLPLYGVIDTPCWKLHTSPLCTTNTKEGSNICLTRTDRGWYCDNAGSVSFFPQAETCKV 360
RSV_F_V187Y_K427Y     VQLPLYGVIDTPCWKLHTSPLCTTNTKEGSNICLTRTDRGWYCDNAGSVSFFPQAETCKV 360
                      ************************************************************

RSV_F_WT              QSNRVFCDTMNSLTLPSEVNLCNVDIFNPKYDCKIMTSKTDVSSSVITSLGAIVSCYGKT 420
RSV_F_A147Y           QSNRVFCDTMNSLTLPSEVNLCNVDIFNPKYDCKIMTSKTDVSSSVITSLGAIVSCYGKT 420
RSV_F_V220Y           QSNRVFCDTMNSLTLPSEVNLCNVDIFNPKYDCKIMTSKTDVSSSVITSLGAIVSCYGKT 420
RSV_F_E222Y           QSNRVFCDTMNSLTLPSEVNLCNVDIFNPKYDCKIMTSKTDVSSSVITSLGAIVSCYGKT 420
RSV_F_F223Y           QSNRVFCDTMNSLTLPSEVNLCNVDIFNPKYDCKIMTSKTDVSSSVITSLGAIVSCYGKT 420
RSV_F_K226Y           QSNRVFCDTMNSLTLPSEVNLCNVDIFNPKYDCKIMTSKTDVSSSVITSLGAIVSCYGKT 420
RSV_F_V469Y           QSNRVFCDTMNSLTLPSEVNLCNVDIFNPKYDCKIMTSKTDVSSSVITSLGAIVSCYGKT 420
RSV_F_K77Y_E222Y      QSNRVFCDTMNSLTLPSEVNLCNVDIFNPKYDCKIMTSKTDVSSSVITSLGAIVSCYGKT 420
RSV_F_N88Y_S255Y      QSNRVFCDTMNSLTLPSEVNLCNVDIFNPKYDCKIMTSKTDVSSSVITSLGAIVSCYGKT 420
RSV_F_M97Y_H159Y      QSNRVFCDTMNSLTLPSEVNLCNVDIFNPKYDCKIMTSKTDVSSSVITSLGAIVSCYGKT 420
RSV_F_V185Y_K427Y     QSNRVFCDTMNSLTLPSEVNLCNVDIFNPKYDCKIMTSKTDVSSSVITSLGAIVSCYGKT 420
RSV_F_V187Y_K427Y     QSNRVFCDTMNSLTLPSEVNLCNVDIFNPKYDCKIMTSKTDVSSSVITSLGAIVSCYGKT 420
                      ************************************************************

RSV_F_WT              KCTASNKNRGIIKTFSNGCDYVSNKGVDTVSVGNTLYYVNKQEGKSLYVKGEPIINFYDP 480
RSV_F_A147Y           KCTASNKNRGIIKTFSNGCDYVSNKGVDTVSVGNTLYYVNKQEGKSLYVKGEPIINFYDP 480
RSV_F_V220Y           KCTASNKNRGIIKTFSNGCDYVSNKGVDTVSVGNTLYYVNKQEGKSLYVKGEPIINFYDP 480
RSV_F_E222Y           KCTASNKNRGIIKTFSNGCDYVSNKGVDTVSVGNTLYYVNKQEGKSLYVKGEPIINFYDP 480
RSV_F_F223Y           KCTASNKNRGIIKTFSNGCDYVSNKGVDTVSVGNTLYYVNKQEGKSLYVKGEPIINFYDP 480
RSV_F_K226Y           KCTASNKNRGIIKTFSNGCDYVSNKGVDTVSVGNTLYYVNKQEGKSLYVKGEPIINFYDP 480
RSV_F_V469Y           KCTASNKNRGIIKTFSNGCDYVSNKGVDTVSVGNTLYYVNKQEGKSLYYKGEPIINFYDP 480
RSV_F_K77Y_E222Y      KCTASNKNRGIIKTFSNGCDYVSNKGVDTVSVGNTLYYVNKQEGKSLYVKGEPIINFYDP 480
RSV_F_N88Y_S255Y      KCTASNKNRGIIKTFSNGCDYVSNKGVDTVSVGNTLYYVNKQEGKSLYVKGEPIINFYDP 480
RSV_F_M97Y_H159Y      KCTASNKNRGIIKTFSNGCDYVSNKGVDTVSVGNTLYYVNKQEGKSLYVKGEPIINFYDP 480
RSV_F_V185Y_K427Y     KCTASNYNRGIIKTFSNGCDYVSNKGVDTVSVGNTLYYVNKQEGKSLYVKGEPIINFYDP 480
RSV_F_V187Y_K427Y     KCTASNYNRGIIKTFSNGCDYVSNKGVDTVSVGNTLYYVNKQEGKSLYVKGEPIINFYDP 480
                      ****** ***************************************** ***********
```

Fig. 20B

```
RSV_F_WT             LVFPSDEFDASISQVNEKINQSLAFIRKSDELLSAIGGYIPEAPRDGQAYVRKDGEWVLL 540
RSV_F_A147Y          LVFPSDEFDASISQVNEKINQSLAFIRKSDELLSAIGGYIPEAPRDGQAYVRKDGEWVLL 540
RSV_F_V220Y          LVFPSDEFDASISQVNEKINQSLAFIRKSDELLSAIGGYIPEAPRDGQAYVRKDGEWVLL 540
RSV_F_E222Y          LVFPSDEFDASISQVNEKINQSLAFIRKSDELLSAIGGYIPEAPRDGQAYVRKDGEWVLL 540
RSV_F_F223Y          LVFPSDEFDASISQVNEKINQSLAFIRKSDELLSAIGGYIPEAPRDGQAYVRKDGEWVLL 540
RSV_F_K226Y          LVFPSDEFDASISQVNEKINQSLAFIRKSDELLSAIGGYIPEAPRDGQAYVRKDGEWVLL 540
RSV_F_V469Y          LVFPSDEFDASISQVNEKINQSLAFIRKSDELLSAIGGYIPEAPRDGQAYVRKDGEWVLL 540
RSV_F_K77Y_E222Y     LVFPSDEFDASISQVNEKINQSLAFIRKSDELLSAIGGYIPEAPRDGQAYVRKDGEWVLL 540
RSV_F_N88Y_S255Y     LVFPSDEFDASISQVNEKINQSLAFIRKSDELLSAIGGYIPEAPRDGQAYVRKDGEWVLL 540
RSV_F_M97Y_H159Y     LVFPSDEFDASISQVNEKINQSLAFIRKSDELLSAIGGYIPEAPRDGQAYVRKDGEWVLL 540
RSV_F_V185Y_K427Y    LVFPSDEFDASISQVNEKINQSLAFIRKSDELLSAIGGYIPEAPRDGQAYVRKDGEWVLL 540
RSV_F_V187Y_K427Y    LVFPSDEFDASISQVNEKINQSLAFIRKSDELLSAIGGYIPEAPRDGQAYVRKDGEWVLL 540
                     ************************************************************

RSV_F_WT             STFLGGLVPRGSHHHHHHSAWSHPQFEK 568
RSV_F_A147Y          STFLGGLVPRGSHHHHHHSAWSHPQFEK 568
RSV_F_V220Y          STFLGGLVPRGSHHHHHHSAWSHPQFEK 568
RSV_F_E222Y          STFLGGLVPRGSHHHHHHSAWSHPQFEK 568
RSV_F_F223Y          STFLGGLVPRGSHHHHHHSAWSHPQFEK 568
RSV_F_K226Y          STFLGGLVPRGSHHHHHHSAWSHPQFEK 568
RSV_F_V469Y          STFLGGLVPRGSHHHHHHSAWSHPQFEK 568
RSV_F_K77Y_E222Y     STFLGGLVPRGSHHHHHHSAWSHPQFEK 568
RSV_F_N88Y_S255Y     STFLGGLVPRGSHHHHHHSAWSHPQFEK 568
RSV_F_M97Y_H159Y     STFLGGLVPRGSHHHHHHSAWSHPQFEK 568
RSV_F_V185Y_K427Y    STFLGGLVPRGSHHHHHHSAWSHPQFEK 568
RSV_F_V187Y_K427Y    STFLGGLVPRGSHHHHHHSAWSHPQFEK 568
                     ****************************
```

Fig. 20C

>DS-Cav1_A147Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSYIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:23)

Fig. 21

>DS-Cav1_V220Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETYIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:24)

Fig. 22

>DS-Cav1_E222Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIYFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:25)

Fig. 23

>DS-Cav1_F223Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEYQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:26)

Fig. 24

>DS-Cav1_K226Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQYNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:27)

Fig. 25

>DS-Cav1_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:28)

Fig. 26

>RSV_F_E222Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIYFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:29)

Fig. 27

>RSV_F_K226Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQYNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK  (SEQ ID NO:30)

Fig. 28

>DS-Cav1_E222Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIyFQQKNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYyKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:31)

Fig. 29

>DS-Cav1_K226Y_V469Y

MELLILKANAITTILTAVTFCFASGQNITEEFYQSTCSAVSKGYLSALRTGWYTSVITIELSNIKENKCNGTDAKVK
LIKQELDKYKNAVTELQLLMQSTPATNNRARRELPRFMNYTLNNAKKTNVTLSKKRKRRFLGFLLGVGSAIASGVAV
CKVLHLEGEVNKIKSALLSTNKAVVSLSNGVSVLTFKVLDLKNYIDKQLLPILNKQSCSISNIETVIEFQQYNNRLL
EITREFSVNAGVTTPVSTYMLTNSELLSLINDMPITNDQKKLMSNNVQIVRQQSYSIMCIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYYKGEPIINFYDPLVFPSDEFDASISQVNEKINQSLAFIRKSDELLSAIGGYIPEAPRDGQAYVRKDGEWVL
LSTFLGGLVPRGSHHHHHHSAWSHPQFEK (SEQ ID NO:32)

Fig. 30

```
RSF_F_WT_Subtype_A      ATGGAGTTGCTAATCCTCAAAGCAAATGCAATTACCACAATCCTCACTGCAGTCACATTT 60
RSF_F_WT_Subtype_B      ATGGAGTTGCTGATCCACAGGTCAAGTGCAATCTTCCTAACTCTTGCTATTAATGCATTG 60
                        ***********.****:**.. ***.****** : *. **  ** .**. :.: .****

RSF_F_WT_Subtype_A      TGTTTTGCTTCTGGTCAAAACATCACTGAAGAATTTTATCAATCAACATGCAGTGCAGTT 120
RSF_F_WT_Subtype_B      TACCTCACCTCAAGTCAGAACATAACTGAGGAGTTTTACCAATCGACATGTAGTGCAGTT 120
                        *.  * .* **:.****.*****.*****.**.***** *****.***** *********

RSF_F_WT_Subtype_A      AGCAAAGGCTATCTTAGTGCTCTGAGAACTGGTTGGTATACCAGTGTTATAACTATAGAA 180
RSF_F_WT_Subtype_B      AGCAGAGGTTATTTTAGTGCTTTAAGAACAGGTTGGTATACCAGTGTCATAACAATAGAA 180
                        ****.*** *** ******** *.*****:**************** *****:******

RSF_F_WT_Subtype_A      TTAAGTAATATCAAGAAAAATAAGTGTAATGGAACAGATGCTAAGGTAAAATTGATAAAA 240
RSF_F_WT_Subtype_B      TTAAGTAATATAACAGAAACCAAATGCAATGGAACTGACACTAAAGTAAAACTTATAAAA 240
                        ***********.*...***. **.** ********:** .****.****** * ******

RSF_F_WT_Subtype_A      CAAGAATTAGATAAATATAAAAATGCTGTAACAGAATTGCAGTTGCTCATGCAAAGCACA 300
RSF_F_WT_Subtype_B      CAAGAATTAGATAAGTATAAGAATGCAGTAACAGAATTACAGCTACTTATGCAAAACACG 300
                        **************.*****.*****:***********.*** *.** *******.***.

RSF_F_WT_Subtype_A      CCAGCAACAAACAATCGAGCCAGAAGAGAACTACCAAGGTTTATGAATTATACACTCAAC 360
RSF_F_WT_Subtype_B      CCAGCTGCCAACAACCGGGCCAGAAGAGAAGCACCACAGCACATGAACTACACAATCAAT 360
                        *****:.*.***** **.************  ****..* : ***** ** ***.****

RSF_F_WT_Subtype_A      AATGCCAAAAAAACCAATGTAACATTAAGCAAGAAAAGGAAAAGAAGATTTCTTGGTTTT 420
RSF_F_WT_Subtype_B      ACCACTAAAAACCTAAATGTATCAATAAGCAAGAAGAGGAAACGAAGATTTCTGGGCTTC 420
                        *.  .* *****.. .******:**:**********.******.********** ** **

RSF_F_WT_Subtype_A      TTGTTAGGTGTTGGATCTGCAATCGCCAGTGGCGTTGCTGTATCTAAGGTCCTGCACCTA 480
RSF_F_WT_Subtype_B      TTGTTAGGTGTAGGATCTGCAATAGCAAGTGGTATAGCTGTATCCAAAGTTCTACACCTT 480
                        ***********:***********.**.*****  .*:******** **.** **.*****:

RSF_F_WT_Subtype_A      GAAGGGGAAGTGAACAAGATCAAAAGTGCTCTACTATCCACAAACAAGGCTGTAGTCAGC 540
RSF_F_WT_Subtype_B      GAAGGAGAAGTGAACAAAATCAAAAATGCTTTGTTGTCTACAAACAAAGCTGTAGTCAGT 540
                        *****.***********.*******.**** *. *.** ********.**********

RSF_F_WT_Subtype_A      TTATCAAATGGAGTCAGTGTCTTAACCAGCAAAGTGTTAGACCTCAAAAACTATATAGAT 600
RSF_F_WT_Subtype_B      CTATCAAATGGGGTCAGTGTTTTAACCAGCAAAGTGTTAGATCTCAAGAATTACATAAAT 600
                         **********.******** ******************** *****.** ** ***.**

RSF_F_WT_Subtype_A      AAACAATTGTTACCTATTGTGAACAAGCAAAGCTGCAGCATATCAAATATAGAAACTGTG 660
RSF_F_WT_Subtype_B      AACCAATTATTACCCATAGTAAATCAACAGAGCTGTCGCATCTTCAACATTGAAACAGTT 660
                        **.*****.*****  **:**.** .*.**.***** .****.* .** **:*****:**

RSF_F_WT_Subtype_A      ATAGAGTTCCAACAAAAGAACAACAGACTACTAGAGATTACCAGGGAATTTAGTGTTAAT 720
RSF_F_WT_Subtype_B      ATAGAATTCCAACAGAAGAATAGCAGATTGTTGGAAATCACCAGAGAATTTAGTGTCAAT 720
                        *****.********.***** *.**** *. *.**.** *****.*********** ***

RSF_F_WT_Subtype_A      GCAGGTGTAACTACACCTGTAAGCACTTACATGTTAACTAATAGTGAATTATTGTCATTA 780
RSF_F_WT_Subtype_B      GCAGGTGTAACAACACCTTTAAGCACTTACATGTTAACAAACAGTGAGTTACTATCATTG 780
                        ***********:****** *******************:** *****.*** *.*****.

RSF_F_WT_Subtype_A      ATCAATGATATGCCTATAACAAATGATCAGAAAAAGTTAATGTCCAACAATGTTCAAATA 840
RSF_F_WT_Subtype_B      ATCAATGATATGCCTATAACAAATGATCAGAAAAAATTAATGTCAAGCAATGTTCAGATA 840
                        ***********************************.********.*.*********.***

RSF_F_WT_Subtype_A      GTTAGACAGCAAAGTTACTCTATCATGTCCATAATAAAAGAGGAAGTCTTAGCATATGTA 900
RSF_F_WT_Subtype_B      GTAAGGCAACAAAGTTATTCTATCATGTCTATAATAAAGGAAGAAGTCCTTGCATATGTT 900
                        **:**.**.******** *********** ********.**.****** *:********:
```

Fig. 36A

```
RSF_F_WT_Subtype_A      GTACAATTACCACTATATGGTGTTATAGATACACCCTGTTGGAAACTACACACATCCCCT 960
RSF_F_WT_Subtype_B      GTACAGCTACCTATCTATGGTGTAATAGATACACCTTGCTGGAAATTACACACATCACCT 960
                        *****. ****:.*.********:*********** ** ****** **********.***

RSF_F_WT_Subtype_A      CTATGTACAACCAACACAAAAGAAGGGTCCAACATCTGTTTAACAAGAACTGACAGAGGA 1020
RSF_F_WT_Subtype_B      CTATGCACCACCAACATCAAAGAAGGATCAAATATTTGTTTAACAAGGACTGATAGAGGA 1020
                        ***** **.*******  .********.**.** ** ***********.***** ******

RSF_F_WT_Subtype_A      TGGTACTGTGACAATGCAGGATCAGTATCTTTCTTCCCACAACCTGAAACATGTAAAGTT 1080
RSF_F_WT_Subtype_B      TGGTATTGTGATAATGCAGGATCAGTATCCTTCTTCCCACAGGCTGACACTTGCAAAGTA 1080
                        ***** ***** ***************** ***********.*****.**:** *****:

RSF_F_WT_Subtype_A      CAATCAAATCGAGTATTTTGTGACACAATGAACAGTTTAACATTACCAAGTGAAGTAAAT 1140
RSF_F_WT_Subtype_B      CAGTCCAATCGAGTATTTTGTGACACTATGAACAGTTTGACATTACCAAGTGAAGTCAGC 1140
                        **.**.*******************:***********.*****************.*.

RSF_F_WT_Subtype_A      CTCTGCAATGTTGACATATTCAACCCCAAATATGATTGTAAAATTATGACTTCAAAAACA 1200
RSF_F_WT_Subtype_B      CTTTGTAACACTGACATATTCAATTCCAAGTATGACTGCAAAATTATGACATCAAAAACA 1200
                        ** ** **  . ***********  ****.***** ** ***********:*********

RSF_F_WT_Subtype_A      GATGTAAGCAGCTCCGTTATCACATCTCTAGGAGCCATTGTGTCATGCTATGGCAAAACT 1260
RSF_F_WT_Subtype_B      GACATAAGCAGCTCAGTAATTACTTCTCTTGGAGCTATAGTGTCATGTTATGGTAAAACT 1260
                        **  .**********.**:** **:*****:***** **:******** ***** ******

RSF_F_WT_Subtype_A      AAATGTACAGCATCCAATAAAAATCGTGGAATCATAAAGACATTTTCTAACGGGTGCGAT 1320
RSF_F_WT_Subtype_B      AAATGCACTGCATCCAATAAAAATCGTGGGATTATAAAGACATTTTCTAATGGTTGTGAC 1320
                        ***** **:*******************.** ***************** ** ** **

RSF_F_WT_Subtype_A      TATGTATCAAATAAAGGGGTGGACACTGTGTCTGTAGGTAACACATTATATTATGTAAAT 1380
RSF_F_WT_Subtype_B      TATGTGTCAAACAAAGGAGTAGATACTGTGTCAGTGGGCAACACTTTATACTATGTAAAC 1380
                        *****.***** *****.**.** ********:**.** *****:***** ********

RSF_F_WT_Subtype_A      AAGCAAGAAGGTAAAAGTCTCTATGTAAAAGGTGAACCAATAATAAATTTCTATGACCCA 1440
RSF_F_WT_Subtype_B      AAGCTGGAAGGCAAGAACCTTTATGTAAAAGGGGAACCTATAATAAATTACTATGATCCT 1440
                        ****:.***** **.*. ** *********** *****:**********:****** **:

RSF_F_WT_Subtype_A      TTAGTATTCCCCTCTGATGAATTTGATGCATCAATATCTCAAGTCAACGAGAAGATTAAC 1500
RSF_F_WT_Subtype_B      CTAGTGTTTCCTTCTGATGAGTTTGATGCATCAATATCTCAAGTCAATGAAAAAATCAAT 1500
                         ****.** ** ********.************************** **.**.** **

RSF_F_WT_Subtype_A      CAGAGCCTAGCATTTATTCGTAAATCCGATGAATTATTACATAATGTAAATGCCGGTAAA 1560
RSF_F_WT_Subtype_B      CAAAGTTTAGCTTTTATTCGTAAATCTGATGAATTACTACATAATGTAAATACTGGCAAA 1560
                        **.**  ****:************** ********* **************.* ** ***

RSF_F_WT_Subtype_A      TCCACCACAAATATCATGATAACTACTATAATTATAGTGATTATAGTAATATTGTTATCA 1620
RSF_F_WT_Subtype_B      TCTACTACAAATATTATGATAACTACAATTATTATAGTAATCATTGTAGTATTGTTATCA 1620
                        ** ** ******** ***********:**:********.** **:***.***********

RSF_F_WT_Subtype_A      TTAATTGCTGTTGGACTGCTCTTATACTGTAAGGCCAGAAGCACACCAGTCACACTAAGC 1680
RSF_F_WT_Subtype_B      TTAATAGCTATTGGTTTACTGTTGTATTGCAAAGCCAAAAACACACCAGTTACACTAAGC 1680
                        *****:***.****: *.** **.** ** **.****.**.********* *********

RSF_F_WT_Subtype_A      AAAGATCAACTGAGTGGTATAAATAATATTGCATTTAGTAACTAA 1725
RSF_F_WT_Subtype_B      AAAGACCAACTAAGTGGAATCAATAATATTGCATTCAGCAAATAG 1725
                        ***** *****.*****:**.************** ** **.**.
```

Sequence identity: 81.57%

Fig. 36 B

>RSV_F_subytpeA_nt_human_codon_opti

ATGGAGCTGCTCATCCTGAAGGCCAACGCCATCACCACCATCCTCACCGCCGTGACCTTCTGCTTCGCCAGCGGCCAGAATATCACCGAGGAGTTCT
ACCAGAGCACCTGCAGCGCCGTGAGCAAGGGCTACCTGAGCGCCCTGAGAACCGGCTGGTACACCAGCGTGATCACCATCGAGCTGAGCAACATCAA
GAAGAACAAGTGCAACGGCACCGACGCCAAGGTGAAGCTCATCAAGCAGGAGCTGGACAAGTACAAGAACGCCGTGACCGAGCTGCAGCTGCTCATG
CAGAGCACCCAGGCCACCAACAACAGGGCCAGAAGGGAGCTGCCCCGGTTCATGAACTACACCCTGAACAACGCCAAGAAAACCAACGTGACCCTGA
GCAAGAAGCGGAAGCGGAGATTCCTGGGCTTCCTGCTGGGCGTGGGCAGCGCCATCGCCAGCGGAGTGGCCGTGTCCAAGGTGCTGCACCTGGAGGG
CGAGGTCAACAACATCAAGAGCGCCCTCCTGAGCACCAACAAGGCCCTGGTGAGCCTGAGCAACGGCGTGAGCGTGCTCACCAGCAAGGTGCTGGAT
CTGAAGAACTACATCGACAAGCAGCTGCTGCCCATCGTGAACAAGCAGAGCTGCAGCATCAGCAACATCGAGACCGTGATCGAGTTCCAGCAGAAGA
ACAACCGGCTGCTGGAGATCACCAGGGAGTTCAGCGTGAACGCCGGCGTGACCACCCCCCTGACCACCTACATGCTCACCAACAGCGAGCTGCTGAG
CCTCATCAACGACATGCCCATCACCAACGACCAGAAGAAGCTCATGAGCAACAACGTGCAGATCCTGCGGCAGCAGAGCTACTCCATCATGAGCATC
ATCAAGGAGGAGGTGCTGGCCTACGTGGTGCAGCTGCCCCTGTACGGCGTGATCGATACCCCTTGCTGGAAGCTGCACACCAGCCCCCTGTGCACCA
CCAACACCAAGGAGGGCAGCAACATCTGCCTCACCAGGACCGATAGAGGCTGGTACTGCGACAACGCCGGCAGCGTGTCATTCTTTCCACAGGCCGA
GACCTGCAAGGTGCAGAGCAACCGGGTGTTCTGCGACACCATGAACAGCCTCACCCTGCCCAGCGAAGTGAACCTGTGCAACGTGGACATCTTCAAC
CCCAAGTACGACTGCAAGATCATGACCAGCAAGACCGACGTGAGCAGCAGCGTGATTACCAGCCTGGGCGCCATCGTGAGCTGCTACGGCAAGACCA
AGTGCACCGCCAGCAACAAGAACCGGGGGATCATCAAGACCTTCAGCAACGGCTGCGACTACGTGAGCAACAAGGGCGTGGATACCGTGAGCGTGGG
CAACACCCTGTACTACGTGAATAAGCAGGAGGGCAAGAGCCTGTACGTGAAGGGCGAGCCCATCATCAACTTCTACGACCCCCTGGTGTTCCCTAGC
GACGAGTTCGATGCCAGCATCAGCCAGGTGAACGAGAAGATCAACCAGAGCCTGGCCTTCATCAGGAAGAGCGACGAGCTGCTGCACAATGTGAATG
CCGGCAAGAGCACCACCAATATCATGATCACCACAATCATCATCGTGATCATTGTGATCCTGCTGTCCCTCATCGCCGTGGGCCTGCTGCTGTACTG
CAAGGCCAGAAGCACCCCTGTGACCCTGTCCAAGGATCAGCTGAGCGGCATCAACAATATCGCCTTCTCCAACTGA

Fig. 37

>RSV_F_subytpeA_nt_CHO_codon_opti

ATGGAACTGCTGATCCTGAAGGCCAACGCCATCACCACCATCCTGACCGCCGTGACCTTCTGCTTCGCCTCCGGCCAGAACATCACCGAGGAATTCT
ACCAGTCTACCTGCTCCGCCGTGTCCAAGGGCTACCTGTCTGCTCTGAGAACCGGCTGGTACACCTCCGTGATCACCATCGAGCTGTCCAACATCAA
GAAAAACAAGTGCAACGGCACCGACGCCAAAGTGAAGCTGATCAAGCAGGAACTGGACAAGTACAAGAATGCCGTGACCGAACTGCAGCTGCTGATG
CAGTCTACCCAGGCCACCAACAACCGGGCCAGACGCGAGCTGCCCAGATTCATGAACTACACCCTGAACAACGCCAAAAAGACCAACGTGACCCTGT
CCAAGAAGCGGAAGCGGCGGTTCCTGGGCTTTCTGCTGGGAGTGGGCTCCGCTATCGCTTCTGGCGTGGCCGTGTCTAAGGTGCTGCACCTGGAAGG
CGAAGTGAACAAGATCAAGTCCGCCCTGCTGAGCACCAACAAGGCCGTGGTGTCCCTGAGCAACGGCGTGTCCGTGCTGACCTCCAAGGTGCTGGAT
CTGAAGAACTACATCGACAAACAGCTGCTGCCCATCGTGAACAAGCAGTCCTGCTCCATCTCCAACATCGAGACAGTGATCGAGTTCCAGCAGAAGA
ACAACCGGCTGCTGGAAATCACCCGCGAGTTCTCCGTGAATGCCGGCGTGACCACCCCCGTGTCCACCTACATGCTGACCAACTCCGAGCTGCTGTC
TCTGATCAACGACATGCCCATCACCAACGACCAGAAAAAGCTGATGTCCAACAACGTGCAGATCGTGCGGCAGCAGTCCTACAGCATCATGTCCATC
ATCAAAGAAGAGGTGCTGGCCTACGTGGTGCAGCTGCCTCTGTACGGCGTGATCGACACCCCCTGCTGGAAGCTGCACACCAGCCCTCTGTGCACCA
CCAACACCAAAGAGGGCAGCAACATCTGCCTGACCCGGACCGACAGAGGCTGGTACTGTGACAACGCTGGCTCCGTCTCATTCTTTCCACAAGCCGA
GACATGCAAGGTGCAGTCCAACCGGGTGTTCTGCGACACCATGAACTCCCTGACCCTGCCCTCTGAAGTGAACCTGTGCAACGTGGACATCTTCAAC
CCTAAGTACGACTGCAAGATCATGACCAGCAAGACCGACGTGTCCAGCTCTGTGATCACCTCCCTGGGCGCCATCGTGTCCTGCTACGGCAAGACCA
AGTGCACCGCCTCCAACAAGAACCGGGGCATCATCAAGACCTTCTCCAACGGCTGCGACTATGTGTCTAACAAGGGCGTGGACACCGTGTCTGTGGG
CAACACCCTGTACTACGTGAACAAACAGGAAGGCAAGTCCCTGTACGTGAAGGGCGAGCCTATCATCAACTTCTACGACCCCCTGGTGTTCCCCAGC
GACGAGTTCGACGCCTCCATCAGCCAAGTGAACGAGAAGATCAACCAGTCCCTGGCCTTCATCCGGAAGTCCGATGAGCTGCTGCACAATGTGAACG
CCGGCAAGTCCACCACCAATATCATCATCACCACAATCATCATCGTCATTATCGTCATCCTGCTCACCCTGATCGCCGTGGGCCTGCTGCTGTACTG
CAAGGCCAGATCCACCCCTGTGACACTGAGCAAGGACCAGCTGTCCGGCATCAACAATATCGCCTTCAGCAACTGA

Fig. 38

>RSV_F_subytpeA_nt_SF9_codon_opti

ATGGAACTGCTGATCCTGAAGGCTAACGCTATCACCACCATCCTGACCGCTGTGACCTTCTGCTTCGCTTCCGGCCAGAACATCACCGAGGAATTCT
ACCAGTCTACCTGCTCCGCTGTGTCCAAGGGTTACCTGTCCGCTCTGCGTACCGGCTGGTACACCTCCGTGATCACCATCGAGCTGTCCAACATCAA
GAAGAACAAGTGCAACGGCACCGACGCTAAAGTGAAGCTGATCAAGCAAGAGCTGGACAAGTACAAGAACGCTGTCACCGAACTGCAGCTGCTGATG
CAGTCCACCCAGGCTACCAACAACCGTGCTCGTCGCGAGCTGCCCCGTTTCATGAACTACACCCTGAACAACGCCAAGAAGACCAACGTCACCCTGT
CCAAGAAGCGCAAGCGCCGTTTCCTGGGTTTCCTGCTGGGTGTCGGTTCCGCTATCGCCTCCGGTGTCGCTGTCTCTAAGGTGCTGCACCTCGAGGG
CGAAGTGAACAAGATCAAGTCCGCCCTGCTGTCCACCAACAAGGCTGTGGTGTCCCTGTCTAACGGTGTCTCCGTGCTGACCTCCAAGGTCCTGGAC
CTGAAGAACTACATCGACAAGCAACTGCTCCCCATCGTGAACAAGCAGTCCTGCTCCATCTCCAACATCGAGACTGTGATCGAGTTCCAGCAAAAGA
ACAACCGCCTGCTCGAGATCACCCGCGAGTTCTCCGTGAACGCTGGTGTCACCACCCCCGTGTCCACCTACATGCTGACCAACTCCGAGCTGCTGTC
CCTGATCAACGACATGCCCATCACCAACGACCAAAAGAAGCTGATGTCCAACAACGTGCAGATCGTGCGTCAGCAGTCCTACTCTATCATGAGCATC
ATCAAGGAAGAGGTGCTGGCTTACGTGGTGCAGCTGCCCCTGTACGGTGTCATCGACACCCCCTGCTGGAAGCTGCACACCTCCCCACTGTGCACCA
CCAACACCAAGGAAGGTTCCAACATCTGCCTGACCCGTACCGACCGTGGCTGGTACTGCGACAACGCTGGTTCCGTTTCATTCTTCCCACAAGCCGA
GACTTGCAAGGTGCAGTCCAACCGTGTGTTCTGCGACACCATGAACTCCCTGACCCTGCCCTCCGAAGTCAACCTGTGCAACGTGGACATCTTCAAC
CCTAAGTACGACTGCAAGATCATGACCAGCAAGACCGACGTGTCCTCCTCTGTCATCACCTCCCTGGGTGCTATCGTGTCCTGCTACGGCAAGACCA
AGTGCACCGCTTCCAACAAGAACCGCGGTATCATCAAGACCTTCTCCAACGGTTGCGACTACGTCAGCAACAAGGGCGTGGACACCGTGTCCGTGGG
CAACACCCTGTACTACGTCAACAAGCAAGAGGGCAAGTCCCTGTACGTGAAGGGCGAGCCCATCATCAACTTCTACGACCCCCTGGTGTTCCCATCC
GACGAGTTCGACGCTTCCATCTCCCAAGTGAACGAGAAGATCAACCAGTCCCTGGCTTTCATCCGCAAGTCCGACGAGCTGCTCCACAACGTCAACG
CTGGCAAGTCCACCACTAACATCATGATCACTACCATCATCATCGTGATCATCGTCATCCTGCTGAGCCTGATCGCTGTGGGCCTGCTGCTGTACTG
CAAGGCTCGTTCCACCCCTGTGACTCTGTCCAAGGACCAGCTGTCCGGTATCAACAACATCGCCTTCAGCAACTAA

Fig. 39

>RSV_F_subytpeA_nt_Mouse_codon_opti

ATGGAACTGCTGATCCTGAAGGCCAACGCCATCACCACCATCCTGACCGCCGTGACCTTCTGCTTCGCCAGCGGCCAGAACATCACCGAGGAATTCT
ACCAGAGCACCTGTAGCGCCGTGTCCAAGGGCTACCTGAGCGCCCTGAGAACCGGCTGGTACACCAGCGTGATCACCATCGAGCTGAGCAACATCAA
GAAAAACAAGTGCAACGGCACCGACGCCAAAGTGAAGCTGATCAAGCAGGAACTGGACAAGTACAAGAACGCCGTGACAGAACTGCAGCTGCTGATG
CAGAGCACCCAGGCCACCAACAACAGAGCCAGACGCGAGCTGCCCAGATTCATGAACTACACCCTGAACAACGCCAAAAAGACCAACGTGACCCTGA
GCAAGAAGAGGAAGCGCAGATTCCTGGGCTTCCTGCTGGGCGTGGGCAGCGCTATTGCTTCTGGCGTGGCCGTGTCTAAGGTGCTGCACCTGGAAGG
CGAAGTGAACAAGATCAAGTCCGCCCTGCTGAGCACCAACAAGGCCGTGGTGTCTCTGAGCAACGGCGTGTCCGTGCTGACCAGCAAGGTGCTGGAT
CTGAAGAACTACATCGACAAACAGCTGCTGCCCATCGTGAACAAGCAGAGCTGCAGCATCAGCAACATCGAGACAGTGATCGAGTTCCAGCAGAAGA
ACAACCGGCTGCTGGAAATCACCCGCGAGTTCAGCGTGAACGCTGGCGTGACCACCCCCGTGTCCACCTACATGCTGACCAACAGCGAGCTGCTGAG
CCTGATCAACGACATGCCCATCACCAACGACCAGAAAAAGCTGATGAGCAACAACGTGCAGATCGTGCGGCAGCAGAGCTACTCCATCATGAGCATC
ATCAAAGAAGAGGTGCTGGCCTACGTGGTGCAGCTGCCTCTGTACGGCGTGATCGACACCCCCTGCTGGAAGCTGCACACCAGCCCTCTGTGCACCA
CCAACACCAAACAGGGCTCCAACATCTGCCTGACCAGAACCGACAGAGGCTGGTACTGCGACAACGCCGGCTCCGTCTCATTCTTTCCACAAGCCGA
GACATGCAAGGTGCAGAGCAACAGAGTGTTCTGCGACACCATGAACAGCCTGACCCTGCCCTCTGAAGTGAACCTGTGCAACGTGGACATCTTCAAC
CCTAAGTACGACTGCAAGATCATGACCTCCAAGACCGACGTGTCCAGCTCCGTGATCACAAGCCTGGGCGCCATCGTGTCCTGCTACGGCAAGACCA
AGTGCACCGCCAGCAACAAGAACAGGGGAATCATCAAGACCTTCAGCAACGGCTGCGACTACGTGTCCAACAAGGGGGTGGACACCGTGTCTGTGGG
CAACACCCTGTACTACGTGAACAAACAGGAAGGCAAGAGCCTGTACGTGAAGGGCGAGCCCATCATCAACTTCTACGACCCCCTGGTGTTCCCCAGC
GACGAGTTCGACGCCAGCATCTCCCAAGTGAACGAGAAGATCAACCAGAGCCTGGCCTTCATCAGAAAGTCCGATGAGCTGCTGCACAATGTGAACG
CCGGCAAGAGCACCACAAACATCATGATCACCACTATCATCATCGTGATCATTGTGATCCTGCTGTCCCTGATCGCCGTGGGCCTGCTGCTGTACTG
CAAGGCCAGATCCACCCCTGTGACCCTGTCCAAGGACCAGCTGAGCGGCATCAACAATATCGCCTTCTCCAACTGA

Fig. 40

>RSV-F_subtypeB_HUMAN_codonOPTI

ATGGAACTGCTGATCCACAGAAGCAGCGCCATCTTCCTGACCCTGGCCATCAACGCCCTGTACCTGACCAGCAGCCAGAACATCACCGAGGAATTCT
ACCAGAGCACCTGTAGCGCCGTGTCCCGGGGCTACTTTAGCGCCCTGAGAACCGGCTGGTACACCAGCGTGATCACCATCGAGCTGAGCAATATCAC
CGAGACAAAGTGCAACGGCACCGACACCAAAGTGAAGCTGATCAAGCAGGAACTGGACAAGTACAAGAACGCCGTGACCGAACTGCAGCTGCTGATG
CAGAATACCCCTGCCGCCAACAACCGCGCCAGAAGAGAAGCCCCCCAGCACATGAACTACACCATCAACACCACCAAGAACCTGAACGTGTCCATCA
GCAAGAAGCGGAAGCGGCGGTTCCTGGCTTTCTGCTGGGAGTGGAAGCGCCATTGCCAGCGGAATCGCCGTGTCTAAGCTGCTGCACCTGGAAGG
CGAAGTGAACAAGATCAAGAATGCCCTGCTGAGCACCAACAAGGCCGTGGTGTCCCTGAGCAACGGCGTGTCCGTGCTGACCTCCAAGGTGCTGGAT
CTGAAGAACTACATCAACAACCAGCTGCTGCCCATCGTGAACCAGCAGAGCTGCCGGATCTTCAACATCGAGACAGTGATCCAGTTCCAGCAGAAGA
ACAGCAGGCTGCTGGAAATCACCCGCGAGTTCAGCGTGAACGCTGGCGTGACCACACCCCTGAGCACCTACATGCTGACCAACAGCGAGCTGCTGTC
CCTGATCAATGACATGCCCATCACCAACGACCAGAAAAAGCTGATGAGCAGCAACGTGCAGATCGTGCGGCAGCAGTCCTACAGCATCATGAGCATC
ATCAAAGAAGAGGTGCTGGCCTACGTGGTGCAGCTGCCTATCTACGGCGTGATCGACACCCCCTGCTGGAAGCTGCACACCAGCCCTCTGTGCACCA
CCAACATCAAAGAGGGCAGCAACATCTGCCTGACCAGAACCGACCGGGGCTGGTACTGCGATAATGCCGGCTCCGTCTCATTCTTTCCACAAGCCGA
TACCTGCAAGGTGCAGAGCAACCGGGTGTTCTGCGACACCATGAACAGCCTGACACTGCCCAGCGAAGTGTCCCTGTGTAACACCGACATCTTCAAC
TCTAAGTACGACTGCAAGATCATGACCAGCAAGACCGACATCAGCTCCTCCGTGATCACAAGCCTGGGCGCCATCGTGTCCTGCTACGGCAAGACCA
AGTGCACCGCCAGCAACAAGAACCGGGGAATCATCAAGACCTTCAGCAACGGCTGCGACTACGTGTCCAACAAGGGGGTGGACACCGTGTCTGTGGG
CAACACCCTGTACTACGTGAACAAGCTGGAAGGGAAGAATCTGTACGTGAAGGGCGAGCCCATCATCAACTACTACGACCCCCTGGTGTTCCCCAGC
GACGAGTTCGATGCCAGCATCAGCCAAGTGAACGAGAAGATCAACCAGAGCCTGGCCTTCATCAGAAAGTCCGATGAGCTGCTGCACAATGTGAACA
CCGGCAAGTCCACCACAAATATCATGATCACCACCATCATTATCGTGATCATCGTGGTGCTGCTGAGCCTCATCGCCATCGGCCTGCTGCTGTACTG
CAAGGCCAAGAACACCCCCGTGACCCTGTCCAAGGATCAGCTGAGCGGCATCAACAATATCGCCTTCTCCAACTGA

Fig. 41

>RSV-F_subtypeB_CHO_codonOPTI

ATGGAACTGCTGATCCACCGGTCCTCCGCCATCTTCCTGACCCTGGCCATCAACGCCCTGTACCTGACCTCCTCCCAGAACATCACCGAGGAATTCT
ACCAGTCTACCTGCTCCGCCGTGTCCCGGGGCTACTTCTCTGCTCTGAGAACCGGCTGGTACACCTCCGTGATCACCATCGAGCTGTCCAATATCAC
CGAGACAAAGTGCAACGGCACCGACACCAAAGTGAAGCTGATCAAGCAGGAACTGGACAAGTACAAGAACGCCGTGACCGAACTGCAGCTGCTGATG
CAGAATACCCCTGCCGCCAACAACCGGGCCAGAAGAGAAGCCCCCCAGCACATGAACTACACCATCAACACCACCAAGAACCTGAACGTGTCCATCT
CCAAGAAGCGGAAGCGGCGGTTCCTGGGCTTTCTGCTCGGAGTGGGCTCCGCTATCGCCTCCGGAATCGCCGTGTCTAAGGTGCTGCACCTGGAAGG
CGAAGTGAACAAGATCAAGAATGCCCTGCTGTCCACCAACAAGGCCGTGGTGTCCCTGTCCAACGGCGTGTCCGTGCTGACCTCCAAGGTGCTGGAT
CTGAAGAACTACATCAACAACCAGCTGCTGCCCATCGTGAACCAGCAGTCCTGCCGGATCTTCAACATCGAGACAGTGATCGAGTTCCAGCACAAGA
ACTCCCGGCTGCTGGAAATCACCCGCGAGTTCTCTGTGAATGCCGGCGTGACCACCCCCCTGTCCACCTACATGCTGACCAACTCCGAGCTGCTGTC
CCTGATCAACGACATGCCCATCACCAACGACCAGAAAAAGCTGATGTCCTCCAACGTGCAGATCGTGCGGCAGCAGAGCTACTCCATCATGTCCATT
ATCAAAGAAGAGGTGCTGGCCTACGTGGTGCAGCTGCCTATCTACGGCGTGATCGACACCCCCTGCTGGAAGCTGCACACCAGCCCTCTGTGCACCA
CCAACATCAAAGAGGGCTCCAACATCTGCCTGACCAGAACCGACCGGGGCTGGTACTGTGACAACGCTGGCTCCGTCTCATTCTTTCCACAAGCCGA
TACCTGCAAGGTGCAGTCCAACCGGGTGTTCTGCGACACCATGAATTCTCTGACCCTGCCCTCCGAAGTGTCTCTGTGTAACACCGACATCTTCAAC
TCTAAGTACGACTGCAAGATCATGACCAGCAAGACCGATATCTCCAGCTCTGTGATCACCTCCCTGGGCGCCATCGTGTCCTGCTACGGCAAGACCA
AGTGCACCGCCTCCAACAAGAACCGGGGCATCATCAAGACCTTCTCCAACGGCTGCGACTACGTGTCCAACAAGGGGGTGGACACCGTGTCTGTGGG
CAACACCCTGTACTACGTGAACAAGCTGGAAGGGAAGAATCTGTACGTGAAGGGCGAGCCCATCATCAACTACTACGACCCCCTGGTGTTCCCCAGC
GACGAGTTCGACGCCTCCATCAGCCAAGTGAACGAGAAGATCAACCAGTCCCTGGCCTTCATCCGGAAGTCCGATGAGCTGCTGCACAATGTGAACA
CCGGCAAGTCCACCACAAATATCATGATCACCACCATCATTATCGTGATCATCGTGGTGCTGCTGAGCCTGATCGCCATCGCCCTGCTGCTGTACTG
CAAGGCCAAGAACACCCCCGTGACCCTGAGCAAGGACCAGCTGTCCGGCATCAACAATATCGCCTTCAGCAAGTGA

Fig. 42

>RSV-F_subtypeB_SF9_codonOPTI

ATGGAACTGCTGATCCACCGTTCCTCCGCTATCTTCCTGACCCTGGCTATCAACGCTCTGTACCTGACCTCCTCCCAGAACATCACCGAGGAATTCT
ACCAGTCTACCTGCTCCGCTGTGTCCCGTGGTTACTTCTCCGCTCTGCGTACCGGCTGGTACACCTCCGTGATCACCATCGAGCTGTCCAACATCAC
TGAGACTAAGTGCAACGGCACCGACACCAAAGTGAAGCTGATCAAGCAAGAGCTGGACAAGTACAAGAACGCTGTGACCGAACTGCAGCTGCTGATG
CAGAACACCCCCGCTGCTAACAACCGTGCTCGTCGCGAAGCTCCCCAGCACATGAACTACACCATCAACACCACCAAGAACCTGAACGTGTCCATCT
CCAAGAAGCGCAAGCGCCGTTTCCTGGGTTTCCTGCTGGGTGTCGGTTCCGCTATCGCTTCCGGTATCGCTGTCTCCAAGGTGCTGCACCTCGAGGG
CGAAGTGAACAAGATCAAGAACGCCCTGCTGTCCACCAACAAGGCTGTGGTGTCCCTGTCCAACGGTGTCTCCGTGCTGACCTCCAAGGTCCTCGAC
CTGAAGAACTACATCAACAACCAGCTGCTGCCCATCGTGAACCAGCAGTCCTGCCGTATCTTCAACATCGAGACTGTGATCGAGTTCCAGCAGAAGA
ACTCCCGTCTGCTCGAGATCACCCGCGAGTTCTCCGTGAACGCTGGTGTCACCACCCCCCTGTCCACCTACATGCTGACCAACTCCGAGCTGCTGTC
CCTGATCAACGACATGCCCATCACCAACGACCAAAAGAAGCTGATGTCCTCCAACGTGCAGATCGTGCGTCAGCAGTCTTACTCCATCATGTCCATC
ATCAAGGAAGAGGTGCTGGCTTACGTGGTGCAGCTGCCTATCTACGGTGTCATCCACACCCCCTGCTGGAAGCTGCACACCTCCCCACTGTGCACCA
CCAACATCAAGGAAGGTTCCAACATCTGCCTGACCCGTACCGACCGTGGCTGGTACTGCGACAACGCTGGTTCCGTTTCATTCTTCCCACAAGCCGA
CACTTGCAAGGTGCAGTCCAACCGTGTGTTCTGCGACACCATGAACTCCCTGACTCTGCCCTCCGAGGTGTCCCTCTGCAACACCGACATCTTCAAC
TCTAAGTACGACTGCAAGATCATGACCTCTAAGACTGACATCTCCTCCAGCGTCATCACCTCCCTGGGTGCTATCGTGTCCTGCTACGGCAAGACCA
AGTGCACCGCTTCCAACAAGAACCGCGGTATCATCAAGACCTTCTCCAACGGTTGCGACTACGTGTCCAACAAGGGCGTGGACACCGTGTCCGTGGG
CAACACCCTGTACTACGTGAACAAGCTCGAGGGCAAGAACCTCTACCTGAAGGGCCAGCCTATCATCAACTACTACGACCCCCTGGTGTTCCCATCC
GACGAGTTCGACGCTTCCATCTCCCAAGTGAACGAGAAGATCAACCAGTCCCTGGCTTTCATCCGCAAGTCCGACGAGCTGCTCCACAACGTGAACA
CCGGCAAGTCCACTACTAACATCATGATCACCACTATCATCATCGTGATCATCGTCGTGCTGCTGAGCCTGATCGCTATCGGCCTGCTGCTGTACTG
CAAGGCTAAGAACACTCCCGTGACCCTCTCTAAGGACCAGCTGTCCGGTATCAACAACATCGCCTTCAGCAAGTAA

Fig. 43

>RSV-F_subtypeB_mouse_codonOPTI

ATGGAACTGCTGATCCACAGAAGCAGCGCCATCTTCCTGACCCTGGCCATCAACGCCCTGTACCTGACCAGCAGCCAGAACATCACCGAGGAATTCT
ACCAGAGCACCTGTAGCGCCGTGTCCAGAGGCTACTTCAGCGCCCTGAGAACCGGCTGGTACACCAGCGTGATCACCATCGAGCTGAGCAACATCAC
AGAGACAAAGTGCAACGGCACCGACACCAAAGTGAAGCTGATCAAGCAGGAACTGGACAAGTACAAGAACGCCGTGACCGAACTGCAGCTGCTGATG
CAGAACACCCCTGCCGCCAACAACAGAGCCAGAAGAGAAGCCCCCCAGCACATGAACTACACCATCAACACCACCAAGAACCTGAACGTGTCCATCA
GCAAGAAGAGGAAGAGAAGATTCCTGGGCTTCCTGCTGGGCGTGGGCAGCGCTATCGCTTCTGGAATCGCCGTGTCTAAGGTGCTGCACCTGCAAGG
CGAAGTGAACAAGATCAAGAACGCTCTGCTGAGCACCAACAAGGCCGTGGTGTCCCTGAGCAACGGCGTGTCCGTGCTGACCTCCAAGGTGCTGGAT
CTGAAGAACTACATCAACAACCAGCTGCTGCCCATCGTGAACCAGCAGAGCTGCAGAATCTTCAACATCGAGACAGTGATCGAGTTCCAGCAGAAGA
ACAGCAGGCTGCTGGAAATCACCCGCGAGTTCAGCGTGAACGCTGGCGTGACCACACCCCTGAGCACCTACATGCTGACCAACAGCGAGCTGCTGTC
TCTGATCAACGACATGCCCATCACCAACGACCAGAAAAAGCTGATGAGCAGCAACGTGCAGATCGTGCGGCAGCAGTCCTACAGCATCATGAGCATC
ATCAAACAAGAGGTCCTCGCCTACGTGGTGCAGCTGCCTATCTACGGCGTGATCGACACCCCCTGCTGGAAGCTGCACACCAGCCCTCTGTGCACCA
CCAACATCAAAGAGGGCAGCAACATCTGCCTGACCAGAACCGACAGAGGCTGGTACTGCGACAACGCCGGCTCCGTCTCATTCTTTCCACAAGCCGA
CACATGCAAGGTGCAGAGCAACAGAGTGTTCTGCGACACCATGAACAGCCTGACACTGCCCAGCGAAGTGTCCCTGTGTAACACCGACATCTTCAAC
TCTAAGTACGACTGCAAGATCATGACCAGCAAGACCGACATCAGCTCCTCCGTGATCACAAGCCTCGGCGCCATCGTGTCCTGCTACGGCAAGACCA
AGTGCACCGCCAGCAACAAGAACAGGGGAATCATCAAGACCTTCAGCAACGGCTGCGACTACGTGTCCAACAAGGGGGTGGACACCGTGTCTGTGGG
CAACACCCTGTACTACGTGAACAAGCTGGAAGGGAAGAATCTGTACGTGAAGGGCGAGCCCATCATCAACTACTACGACCCCCTGGTGTTCCCCAGC
GACGAGTTCGACGCCAGCATCAGCCAAGTGAACGAGAAGATCAACCAGAGCCTGGCCTTCATCAGAAAGTCCGATGAGCTGCTGCACAATGTGAACA
CCGGCAAGTCCACAACAAACATCATGATCACCACCATCATTATCGTGATCATCGTGGTGCTGCTGAGCCTGATCGCCATCGGCCTGCTGCTGTACTG
CAAGGCCAAGAACACACCCGTGACCCTGTCCAAGGACCAGCTGAGCGGCATCAACAATATCGCCTTCTCCAAGTGA

Fig. 44

>RSV_F_subtypeA_DS-CAV1_nt_Human_codon_opti

ATGGAACTGCTGATCCTGAAGGCCAACGCCATCACCACCATCCTGACCGCCGTGACCTTCTGCTTCGCCAGCGGCCAGAACATCACCGAGGAATTCT
ACCAGAGCACCTGCAGCGCCGTGAGCAAGGGCTACCTGAGCGCCCTGCGGACCGGCTGGTACACCAGCGTGATCACCATCGAGCTGTCCAACATCAA
AGAAAACAAGTGCAACGGCACCGACGCCAAAGTGAAGCTGATCAAGCAGGAACTGGACAAGTACAAGAACGCCGTGACCGAGCTGCAGCTGCTGATG
CAGAGCACCCCCGCCACCAACAACAGAGCCAGAAGAGAGCTGCCCCGGTTCATGAACTACACCCTGAACAACGCCAAGAAAACCAACGTGACCCTGA
GCAAGAAGAGAAAGAGAAGATTCCTGGGCTTCCTGCTGGGCGTGGGCAGCGCCATTGCCAGCGGCGTGGCCGTGTGCAAAGTGCTGCACCTGGAAGG
CGAAGTGAACAAGATCAAGTCCGCCCTGCTGTCCACCAACAAGGCCGTGGTGTCCCTGAGCAACGGCGTGAGCGTGCTGACCTTCAAGGTGCTGGAT
CTGAAGAACTACATCGACAAGCAGCTGCTGCCCATCCTGAACAAGCAGAGCTGCAGCATCAGCAACATCGAGACAGTGATCGAGTTCCAGCAGAAGA
ACAACCGGCTGCTGGAAATCACCCGGGAGTTCAGCGTGAACGCCGGAGTGACCACCCCCGTGTCCACCTACATGCTGACCAACAGCGAGCTGCTGTC
CCTGATCAATGACATGCCCATCACCAACGACCAGAAAAAGCTGATGAGCAACAACGTGCAGATCGTGCGGCAGCAGAGCTACTCCATCATGTGCATC
ATCAAAGAAGAGGTGCTGGCCTACGTGGTGCAGCTGCCCCTGTACGGCGTGATCGACACCCCCTGCTGGAAGCTGCACACCAGCCCCCTGTGCACAA
CCAACACCAAAGAGGGCAGCAACATCTGCCTGACCCGGACCGACCGGGGCTGGTACTGCGACAACGCCGGCAGCGTGTCCTTCTTTCCACAGGCCGA
GACATGCAAGGTGCAGAGCAACCGGGTGTTCTGCGACACCATGAACAGCCTGACCCTGCCCTCCGAAGTGAACCTGTGCAACGTGGACATCTTCAAC
CCCAAGTACGACTGCAAGATCATGACCTCCAAGACCGACGTGTCCAGCTCCGTGATCACCTCCCTGGGCGCCATCGTGTCCTGCTACGGCAAGACCA
AGTGCACCGCCAGCAACAAGAACAGAGGCATCATCAAGACCTTCAGCAACGGCTGCGACTACGTGTCCAATAAGGGCGTGGACACCGTGTCCGTGGG
CAACACACTGTACTACGTGAATAAGCAGGAAGGCAAGAGCCTGTACGTGAAGGGCGAGCCCATCATCAACTTCTACGACCCCCTGGTGTTCCCCAGC
GACGAGTTCGACGCCAGCATCAGCCAGGTGAACGAGAAGATCAACCAGAGCCTGGCCTTCATCAGAAAGAGCGACGAACTGCTGTCCGCCATCGGCG
GCTACATCCCCGAGGCCCCCAGAGATGGCCAGGCCTACGTGCGGAAGGACGGCGAGTGGGTGCTGCTGTCTACATTTCTGGGCGGCCTGGTGCCTAG
AGGCTCTCACCACCACCATCACCACAGCGCCTGGTCCCACCCCCAGTTCGAGAAGTGA

Fig. 45

>RSV_F_subtypeA_DS_nt_Human_codon_opti

ATGGAACTGCTGATCCTGAAGGCCAACGCCATCACCACCATCCTGACCGCCGTGACCTTCTGCTTCGCCAGCGGCCAGAACATCACCGAGGAATTCT
ACCAGAGCACCTGCAGCGCCGTGAGCAAGGGCTACCTGAGCGCCCTGCGGACCGGCTGGTACACCAGCGTGATCACCATCGAGCTGTCCAACATCAA
AGAAAACAAGTGCAACGGCACCGACGCCAAAGTGAAGCTGATCAAGCAGGAACTGGACAAGTACAAGAACGCCGTGACCGAGCTGCAGCTGCTGATG
CAGAGCACCCCCGCCACCAACAACAGAGCCAGAAGAGAGCTGCCCCGGTTCATGAACTACACCCTGAACAACGCCAAGAAAACCAACGTGACCCTGA
GCAAGAAGAGAAAGAGAAGATTCCTGGGCTTCCTGCTGGGCGTGGGCAGCGCCATTGCCAGCGGCGTGGCCGTGTGCAAAGTGCTGCACCTGGAAGG
CGAAGTGAACAAGATCAAGTCCGCCCTGCTGTCCACCAACAAGGCCGTGGTGTCCCTGAGCAACGGCGTGAGCGTGCTGACCAGCAAGGTGCTGGAT
CTGAAGAACTACATCGACAAGCAGCTGCTGCCCATCGTGAACAAGCAGAGCTGCAGCATCAGCAACATCGAGACAGTGATCGAGTTCCAGCAGAAGA
ACAACCGGCTGCTGGAAATCACCCGGGAGTTCAGCGTGAACGCCGGAGTGACCACCCCCGTGTCCACCTACATGCTGACCAACAGCGAGCTGCTGTC
CCTGATCAATGACATGCCCATCACCAACGACCAGAAAAAGCTGATGAGCAACAACGTGCAGATCGTGCGGCAGCAGAGCTACTCCATCATGTGCATC
ATCAAAGAAGAGGTGCTGGCCTACGTGGTGCAGCTGCCCCTGTACGGCGTGATCGACACCCCCTGCTGGAAGCTGCACACCAGCCCCCTGTGCACAA
CCAACACCAAAGAGGGCAGCAACATCTGCCTGACCCGGACCGACCGGGGCTGGTACTGCGACAACGCCGGCAGCGTGTCCTTCTTTCCACAGGCCGA
GACATGCAAGGTGCAGAGCAACCGGGTGTTCTGCGACACCATGAACAGCCTGACCCTGCCCTCCGAAGTGAACCTGTGCAACGTGGACATCTTCAAC
CCCAAGTACGACTGCAAGATCATGACCTCCAAGACCGACGTGTCCAGCTCCGTGATCACCTCCCTGGGCGCCATCGTGTCCTGCTACGGCAAGACCA
AGTGCACCGCCAGCAACAAGAACAGAGGCATCATCAAGACCTTCAGCAACGGCTGCGACTACGTGTCCAATAAGGGCGTGGACACCGTGTCCGTGGG
CAACACACTGTACTACGTGAATAAGCAGGAAGGCAAGAGCCTGTACGTGAAGGGCGAGCCCATCATCAACTTCTACGACCCCCTGGTGTTCCCCAGC
GACGAGTTCGACGCCAGCATCAGCCAGGTGAACGAGAAGATCAACCAGAGCCTGGCCTTCATCAGAAAGAGCGACGAACTGCTGTCCGCCATCGGCG
GCTACATCCCCGAGGCCCCCAGAGATGGCCAGGCCTACGTGCGGAAGGACGGCGAGTGGGTGCTGCTGTCTACATTTCTGGGCGGCCTGGTGCCTAG
AGGCTCTCACCACCACCATCACCACAGCGCCTGGTCCCACCCCCAGTTCGAGAAGTGA

Fig. 46

>RSV_F_subtypeA_CAV1_nt_Human_codon_opti

ATGGAACTGCTGATCCTGAAGGCCAACGCCATCACCACCATCCTGACCGCCGTGACCTTCTGCTTCGCCAGCGGCCAGAACATCACCGAGGAATTCT
ACCAGAGCACCTGCAGCGCCGTGAGCAAGGGCTACCTGAGCGCCCTGCGGACCGGCTGGTACACCAGCGTGATCACCATCGAGCTGTCCAACATCAA
AGAAAACAAGTGCAACGGCACCGACGCCAAAGTGAAGCTGATCAAGCAGGAACTGGACAAGTACAAGAACGCCGTGACCGAGCTGCAGCTGCTGATG
CAGAGCACCCCCGCCACCAACAACAGAGCCAGAAGAGAGCTGCCCCGGTTCATGAACTACACCCTGAACAACGCCAAGAAAACCAACGTGACCCTGA
GCAAGAAGAGAAAGAGAAGATTCCTGGGCTTCCTGCTGGGCGTGGGCAGCGCCATTGCCAGCGGCGTGGCCGTGTCCAAAGTGCTGCACCTGGAAGG
CGAAGTGAACAAGATCAAGTCCGCCCTGCTGTCCACCAACAAGGCCGTGGTGTCCCTGAGCAACGGCGTGAGCGTGCTGACCTTCAAGGTGCTGGAT
CTGAAGAACTACATCGACAAGCAGCTGCTGCCCATCCTGAACAAGCAGAGCTGCAGCATCAGCAACATCGAGACAGTGATCGAGTTCCAGCAGAAGA
ACAACCGGCTGCTGGAAATCACCCGGGAGTTCAGCGTGAACGCCGGAGTGACCACCCCCGTGTCCACCTACATGCTGACCAACAGCGAGCTGCTGTC
CCTGATCAATGACATGCCCATCACCAACGACCAGAAAAAGCTGATGAGCAACAACGTGCAGATCGTGCGGCAGCAGAGCTACTCCATCATGAGCATC
ATCAAAGAAGAGGTGCTGGCCTACGTGGTGCAGCTGCCCCTGTACGGCGTGATCGACACCCCCTGCTGGAAGCTGCACACCAGCCCCCTGTGCACAA
CCAACACCAAAGAGGGCAGCAACATCTGCCTGACCCGGACCGACCGGGGCTGGTACTGCGACAACGCCGGCAGCGTGTCCTTCTTTCCACAGGCCGA
GACATGCAAGGTGCAGAGCAACCGGGTGTTCTGCGACACCATGAACAGCCTGACCCTGCCCTCCGAAGTGAACCTGTGCAACGTGGACATCTTCAAC
CCCAAGTACGACTGCAAGATCATGACCTCCAAGACCGACGTGTCCAGCTCCGTGATCACCTCCCTGGGCGCCATCGTGTCCTGCTACGGCAAGACCA
AGTGCACCGCCAGCAACAAGAACAGAGGCATCATCAAGACCTTCAGCAACGGCTGCGACTACGTGTCCAATAAGGGCGTGGACACCGTGTCCGTGGG
CAACACACTGTACTACGTGAATAAGCAGGAAGGCAAGAGCCTGTACGTGAAGGGCGAGCCCATCATCAACTTCTACGACCCCCTGGTGTTCCCCAGC
GACGAGTTCGACGCCAGCATCAGCCAGGTGAACGAGAAGATCAACCAGAGCCTGGCCTTCATCAGAAAGAGCGACGAACTGCTGTCCGCCATCGGCG
GCTACATCCCCGAGGCCCCCAGAGATGGCCAGGCCTACGTGCGGAAGGACGGCGAGTGGGTGCTGCTGTCTACATTTCTGGGCGGCCTGGTGCCTAG
AGGCTCTCACCACCACCATCACCACAGCGCCTGGTCCCACCCCCAGTTCGAGAAGTGA

Fig. 47

CONFORMATIONALLY STABILIZED RSV PRE-FUSION F PROTEINS

CROSS-REFERENCE TO RELATED APPLICATIONS

This application claims the benefit of U.S. Provisional Patent Application No. 61/858,533, filed Jul. 25, 2013, the contents of which are hereby incorporated by reference.

STATEMENT REGARDING FEDERALLY SPONSORED RESEARCH

This invention was made with government support under grant number 1R43AI112124-01A1 awarded by the National Institute of Allergy and Infectious Diseases (NIAID). The government has certain rights in the invention.

SEQUENCE LISTING

The instant application contains a Sequence Listing which has been submitted electronically in ASCII format and is hereby incorporated by reference in its entirety. Said ASCII copy, created on Jul. 24, 2014, is named Avatar_007_US2_Sequence_Listing.txt and is 195,572 bytes in size.

COPYRIGHT & INCORPORATION-BY-REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

For the purposes of only those jurisdictions that permit incorporation by reference, the text of all documents cited herein is hereby incorporated by reference in its entirety.

BACKGROUND OF THE INVENTION

Each year, respiratory syncytial virus (RSV) infects 4-5 million children in the US, and is the leading cause of infant hospitalizations (~150,000 hospitalizations). Globally, it accounts for 6.7% of deaths in infants less than 1 year old, second only to malaria. In addition, it poses a serious threat to other high-risk groups, including elderly and immunocompromised subjects, where it results in approximately an additional 180,000 hospitalizations and 12,000 deaths in the US. There are no current frontline treatments for RSV, and the only currently approved prophylactic treatment for RSV is passive administration of the licensed monoclonal antibody Synagis (palivizumab), which recognizes the RSV fusion (F) protein, and reduces incidence of severe disease by only ~50%. The high cost of prophylaxis with Synagis limits its use only to premature infants and infants less than 24 months old with congenital heart disease. For a review see Costello et al., "Targeting RSV with Vaccines and Small Molecule Drugs, Infectious Disorders," Drug Targets, 2012, vol. 12, no. 2. The development of a more effective and, ideally, more cost-effective RSV vaccine would be of enormous value. Clinical evidence that RSV F protein-specific antibodies can protect against disease has prompted a concerted effort to identify additional and better monoclonal antibodies, and to develop a protective vaccine to address this significant unmet medical need.

BRIEF SUMMARY OF THE INVENTION

Some aspects of the present invention are summarized below. Additional aspects are described in the Detailed Description of the Invention, the Examples, the Figures and the claims herein.

The RSV F protein is known to induce potent neutralizing antibodies that correlate with protection against RSV. Recently it has been shown that the pre-fusion conformation of the RSV F protein trimer (which may be referred to as "pre-fusion F" or "pre-F" herein) is the primary determinant of neutralizing activity in human sera. Also, the most potent neutralizing antibodies (nAbs) isolated to date specifically bind only to the pre-fusion conformation. However, soluble pre-F is highly unstable and readily transitions to the post-fusion conformation—limiting its usefulness as a vaccine immunogen. An RSV F protein stabilized in its pre-fusion (pre-F) conformation could be very valuable—providing a candidate RSV vaccine immunogen. Similarly, such a stabilized RSV pre-F protein could also be useful for the generation of antibodies, such as diagnostic and therapeutic antibodies. The crystal structure of the RSV F protein (bound to a potent nAb—D25) in its pre-fusion conformation was recently described. See McLellan et al., 2013, Science, 340, p. 1113-1117, the contents of which are hereby incorporated by reference in their entirety. Building on this work, the present inventors have performed extensive analysis of the structure of the RSV F protein and have developed a variety of novel design strategies and novel constructs to stabilize or "lock" the RSV F protein in its pre-F conformation.

In some embodiments the present invention provides RSV F polypeptides, proteins, and protein complexes, such as those that can be or are stabilized or "locked" in a pre-fusion conformation, for example using targeted cross-links, such as targeted di-tyrosine cross-links. The present invention also provides methods for making and using such RSV F polypeptides, proteins, and protein complexes.

In some embodiments, the present invention provides specific locations within the amino acid sequence of the RSV F protein at which, or between which, cross-links can be made in order to stabilize the RSV F protein in its pre-F conformation. In some embodiments, the cross-links are targeted di-tyrosine cross-links. Where di-tyrosine cross-links are used, the present invention provides specific amino acid residues (or pairs of amino acid residues) that either comprise a pre-existing tyrosine residue or can be or are mutated to a tyrosine residue such that di-tyrosine cross-links can be made.

In some embodiments, the present invention provides an isolated RSV F polypeptide, protein or protein complex comprising at least one di-tyrosine cross-link, wherein at least one tyrosine of the at least one di-tyrosine cross-links originates from a point mutation to tyrosine.

In some embodiments, the invention provides an isolated RSV F polypeptide, protein or protein complex having at least about 75% sequence identity to SEQ ID NO:1, 2, 3, 4, 5, 6, 7, 8, 9 or 10, or amino acid residues 1-513 thereof (comprising the RSV F ectodomain), wherein the protein polypeptide comprises at least one tyrosine residue that originates from a point mutation to tyrosine. In some such embodiments the RSV F polypeptides, proteins or protein complexes contain at least one di-tyrosine cross-link wherein at least one tyrosine residue of the at least one cross-link originates from a point mutation to tyrosine.

In some embodiments, the invention provides an isolated RSV F polypeptide having the amino acid sequence of SEQ ID NO:11, 12, 13, 14, 15, 16, 17, 18, 19, 20, 21, 22, 23, 24, 25, 26, 27, 28, 29, 30, 31 or 32, or amino acid residues 1-513 thereof (comprising the RSV F ectodomain). In some embodiments, the invention provides an isolated RSV F protein or polypeptide having at least about 75% sequence identity to SEQ ID NO:11, 12, 13, 14, 15, 16, 17, 18, 19, 20, 21, 22, 23, 24, 25, 26, 27, 28, 29, 30, 31 or 32, or amino acid residues 1-513 thereof (comprising the RSV F ectodomain). In some such embodiments the RSV F polypeptides, proteins or protein complexes contain at least one di-tyrosine cross-link wherein at least one tyrosine residue of the at least one cross-link originates from a point mutation to tyrosine.

In some embodiments, where di-tyrosine cross-links are present, the di-tyrosine cross-link comprises two pre-existing tyrosine residues. In some embodiments, the di-tyrosine cross-link comprises a pre-existing tyrosine cross-linked to a tyrosine originating from a point mutation to tyrosine. In some embodiments, the di-tyrosine cross-link comprises two tyrosines originating from point mutations to tyrosine. In some embodiments, the di-tyrosine cross-link comprises an intra-protomer bond, an inter-protomer bond, an intra-molecular bond, an inter-molecular bond, or any combination thereof. In some embodiments, the di-tyrosine cross-link comprises a bond within or between a RSV F protein F1 polypeptide and a RSV F protein F2 polypeptide. In some embodiments, the point mutation to tyrosine is located at one or more amino acid positions selected from the group consisting of amino acid positions: 77, 88, 97, 147, 150, 155, 159, 183, 185, 187, 220, 222, 223, 226, 255, 427 or 469 of SEQ ID NO: 1 or SEQ ID NO: 4, or any amino acid position that corresponds to one of such amino acid positions in another RSV F amino acid sequence or ectodomain thereof.

In some embodiments, the invention provides an isolated RSV F polypeptide, protein or protein complex having at least about 75% sequence identity to SEQ ID NO:1, 2, 3, 4, 5, 6, 7, 8, 9 or 10, wherein the polypeptide comprises at least one di-tyrosine cross-link, wherein one or both tyrosines of the cross-link originates from a point mutation to tyrosine, and wherein the cross-links are located between one or more paired tyrosine amino acid residues located at amino acid positions: 147 and 286; 198 and 220; 198 and 222; 198 and 223; 198 and 226; 33 and 469; 77 and 222; 88 and 255; 97 and 159; 183 and 427; 185 and 427; or 187 and 427. In some embodiments, the RSV F polypeptide, protein, or protein complex comprises more than one di-tyrosine cross-link. In some embodiments, the RSV F polypeptide, protein, or protein complex comprises two, three, four, five or more di-tyrosine cross-links. In some embodiments, the RSV F polypeptide, protein, or protein complex comprises di-tyrosine cross-links at paired tyrosine amino acid residues located at amino acid positions 77 and 222, and 33 and 469.

In some embodiments, the RSV F polypeptides, proteins, or protein complexes of the invention further comprise one or more additional cross-links, such as disulfide bonds. In such embodiments, at least one cysteine of the one or more disulfide bonds originates from a point mutation to cysteine. In some embodiments, the RSV F polypeptides, proteins, or protein complexes further comprise cavity-filling hydrophobic amino acid substitutions. In some embodiments, the RSV F polypeptides, proteins, or protein complexes further comprises a trimerization domain. In such embodiments, the trimerization domain is a foldon domain.

In some embodiments, the RSV F polypeptides, proteins, or protein complexes of the invention are capable of eliciting a protective immune response in a subject and/or eliciting production of RSV-specific neutralizing antibodies in a subject. In some embodiments, the RSV F polypeptides, proteins, or protein complexes of the invention comprise at least one antigenic site capable of binding a neutralizing antibody, for example, the antigenic site ø.

In some embodiments, the invention provides compositions (such as pharmaceutical compositions and/or vaccine compositions) comprising one or more RSV F polypeptides, proteins, or protein complexes of the invention. In some embodiments, such compositions comprise an adjuvant, a carrier, an immunostimulatory agent, or any combination thereof. In some embodiments, the composition is, or forms part of, a vaccine for respiratory syncytial virus. In some embodiments, the invention provides a method of vaccinating a subject against RSV, the method comprising administering an effective amount of a composition comprising one or more of the RSV F polypeptides, proteins, or protein complexes of the invention to a subject. In some embodiments, the subject is a human of less than 24 months in age or a human of greater than 50 years in age. In some embodiments, the administering comprises a single immunization. In some embodiments, a method of the invention further comprises administering to a subject a pharmaceutical composition comprising one or more RSV F polypeptides, proteins, or protein complexes of the invention so as to treat or prevent an RSV infection in the subject. In some embodiments, the invention provides a medicament for inducing an immune response in a subject, comprising one or more the RSV F polypeptides, proteins, or protein complexes of the invention. In some embodiments, the medicament is a vaccine.

In some embodiments, the invention provides a method of making a RSV vaccine immunogen, comprising (a) identifying or obtaining a RSV F polypeptide, protein or protein complex in a pre-fusion conformation; (b) selecting one or more regions in the RSV F polypeptide, protein or protein complex where the introduction of one or more cross-links (such as di-tyrosine cross-links) could stabilize the pre-fusion conformation; (c) introducing into the RSV F protein one or more cross-links (such as di-tyrosine cross-links) at one or more of the regions selected in step (b) to form an engineered RSV F polypeptide, protein or protein complex; and (d) determining if the engineered RSV F polypeptide, protein or protein complex has one or more properties selected from the group consisting of: (i) enhanced ability bind to a neutralizing antibody, (ii) enhanced ability bind to a broadly neutralizing, (iii) enhanced ability bind to and activate B cell receptors, (iv) enhanced ability to elicit an antibody response in an animal, (v) enhanced ability to elicit a protective antibody response in an animal, (vi) enhanced ability to elicit production of neutralizing antibodies in an animal, (vii) enhanced ability to elicit production of broadly neutralizing antibodies in an animal, (viii) enhanced ability to elicit a protective immune response in an animal, and (ix) enhanced ability to bind to and elicit production of antibodies that recognize quaternary neutralizing epitopes in an animal, wherein if the engineered RSV F polypeptide, protein or protein complex has one or more properties i. to ix., the engineered RSV F polypeptide, protein or protein complex is a RSV vaccine immunogen candidate. In some such embodiments, step (d) comprises performing one or more assays to assess the ability of the engineered RSV F protein to bind to a neutralizing antibody, bind to a broadly neutralizing antibody, bind to and activate a B cell receptors elicit an antibody response in an animal, elicit a protective antibody response in an animal, elicit production of neutralizing antibodies in an animal, elicit production of broadly neutralizing antibodies in an animal, elicit a protective immune response in an animal, and/or elicit production of antibodies that recognize quaternary neutralizing epitopes in an animal. In some embodiments, where di-tyrosine cross-links are used, at least one tyrosine of the one or more di-tyrosine cross-links introduced in step (c) originates from a point mutation to tyrosine. In some embodiments, the method further comprises, prior to step (c), introducing into the RSV F protein one or more point mutations to tyrosine at one or more of the regions selected in step (b).

These and other embodiments of the present invention are described throughout the present patent specification.

BRIEF DESCRIPTION OF THE DRAWINGS

FIGS. 1A-1B. Amino acid sequences of (A) soluble RSV F protein from RSV subtype A (WT) (SEQ ID NO:1), and (B) full-length RSV F protein from RSV subtype A (SEQ ID NO:2) (Accession No. AHJ60043.1). Amino acid residues 1-513 of both sequences are the core sequences of the RSV F protein that are common to both the soluble and membrane-bound (full-length) forms. The C-terminal sequences from amino acid residue 514 onwards in SEQ ID NO. 1 comprise a foldon trimerization domain followed by a thrombin cleavage site, 6× His-tag (SEQ ID NO: 46), and a strep tag. The C-terminal sequences from amino acid residue 514 onwards in SEQ ID NO. 2 comprise the endogenous RSV F protein sequence containing the transmembrane region and cytoplasmic tail.

FIGS. 2A-2B. Amino acid sequences of (A) soluble RSV F protein from RSV subtype B (SEQ ID NO:3), and (B) full-length RSV F protein from RSV subtype B (SEQ ID NO:4) (Accession No. AHL84194). Amino acid residues 1-513 of both sequences are the core sequences of the RSV F protein that are common to both the soluble and membrane-bound (full-length) forms. The C-terminal sequences from amino acid residue 514 onwards in SEQ ID NO. 3 comprise a foldon trimerization domain followed by a thrombin cleavage site, 6× His-tag (SEQ ID NO: 46), and a strep tag. The C-terminal sequences from amino acid residue 514 onwards in SEQ ID NO. 4 comprise the endogenous RSV F protein sequence containing the transmembrane region and cytoplasmic tail.

FIGS. 3A-3B. Amino acid sequences of (A) soluble DS-Cav1 modified RSV F protein (SEQ ID NO:5), and (B) full-length DS-Cav1 modified RSV F protein (SEQ ID NO:6) (McLellan et al. (2013) Science 342:592-598). Amino acid residues 1-513 of both sequences are the core sequences of the RSV F protein that are common to both the soluble and membrane-bound (full-length) forms. The C-terminal sequences from amino acid residue 514 onwards in SEQ ID NO. 5 comprise a foldon trimerization domain followed by a thrombin cleavage site, 6× His-tag (SEQ ID NO: 46), and a strep tag. The C-terminal sequences from amino acid residue 514 onwards in SEQ ID NO. 6 comprise the endogenous RSV F protein sequence containing the transmembrane region and cytoplasmic tail.

FIGS. 4A-4B. Amino acid sequences of (A) soluble Cav1 modified RSV F protein (SEQ ID NO:7), and (B) full-length Cav1 modified RSV F protein sequence (SEQ ID NO:8) (McLellan et al. (2013) Science 342:592-598).). Amino acid residues 1-513 of both sequences are the core sequences of the RSV F protein that are common to both the soluble and membrane-bound (full-length) forms. The C-terminal sequences from amino acid residue 514 onwards in SEQ ID NO. 7 comprise a foldon trimerization domain followed by a thrombin cleavage site, 6× His-tag (SEQ ID NO: 46), and a strep tag. The C-terminal sequences from amino acid residue 514 onwards in SEQ ID NO. 8 comprise the endogenous RSV F protein sequence containing the transmembrane region and cytoplasmic tail.

FIGS. 5A-5B. Amino acid sequences of (A) soluble DS modified RSV F protein (SEQ ID NO:9), and (B) full-length DS modified RSV F protein sequence (SEQ ID NO:10) (McLellan et al. (2013) Science 342:592-598).). Amino acid residues 1-513 of both sequences are the core sequences of the RSV F protein that are common to both the soluble and membrane-bound (full-length) forms. The C-terminal sequences from amino acid residue 514 onwards in SEQ ID NO. 9 comprise a foldon trimerization domain followed by a thrombin cleavage site, 6× His-tag (SEQ ID NO: 46), and a strep tag. The C-terminal sequences from amino acid residue 514 onwards in SEQ ID NO. 10 comprise the endogenous RSV F protein sequence containing the transmembrane region and cytoplasmic tail.

FIG. 6. Sequence alignment of RSV F proteins from RSV subtype A (SEQ ID NO:1—identified as "RSV_F_WT" in the figure) and subtype B (SEQ ID NO:4). Amino acid residues shown in bold and underlined in the subtype A sequence indicate sites that can be targeted for di-tyrosine cross-linking either as single or double mutants. The equivalent sites in subtype B are also shown in boxes. The designated positions targeted for di-tyrosine cross-linking are 100% conserved between RSV subtypes A and B. Amino acid residues 1-513 of both sequences are the core sequences of the RSV F protein. The C-terminal sequences from amino acid residue 514 onwards in SEQ ID NO. 1 comprise a foldon trimerization domain followed by a thrombin cleavage site, 6× His-tag (SEQ ID NO: 46), and a strep tag. The C-terminal sequences from amino acid residue 514 onwards in SEQ ID NO. 4 comprise the endogenous RSV F protein sequence containing the transmembrane region and cytoplasmic tail.

FIG. 7. Sequence alignment of DS-Cav1 RSV F protein (SEQ ID NO:5), and RSV F proteins from RSV subtype A (SEQ ID NO:1) and subtype B (SEQ ID NO:4). The C-terminal sequences shown in italics in the DS-Cav1 and RSV subtype A sequences (residues 514-568) contain the exogenous Foldon trimerization domain followed by a thrombin cleavage site, 6× His-tag (SEQ ID NO: 46) and a strep tag. The C-terminal sequence shown in bold and underlined in the RSV subtype B sequence (residues 514-574) is the endogenous F protein sequence containing the transmembrane region and cytoplasmic tail.

FIG. 8. Amino acid sequence of a modified soluble RSV F protein (subtype A) comprising a to-tyrosine mutation at position 147 (A147Y) (SEQ ID NO:11). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 9. Amino acid sequence of a modified soluble RSV F protein (subtype A) comprising a to-tyrosine mutation at position 220 (V220Y) (SEQ ID NO:12). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 10. Amino acid sequence of a modified soluble RSV F protein (subtype A) comprising a to-tyrosine mutation at position 222 (E222Y) (SEQ ID NO:13). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 11. Amino acid sequence of a modified soluble RSV F protein (subtype A) comprising a to-tyrosine mutation at position 223 (F223Y) (SEQ ID NO:14). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 12. Amino acid sequence of a modified soluble RSV F protein (subtype A) comprising a to-tyrosine mutation at position 226 (K226Y) (SEQ ID NO:15). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 13. Amino acid sequence of a modified soluble RSV F protein (subtype A) comprising a to-tyrosine mutation at position 469 (V469Y) (SEQ ID NO:16). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 14. Amino acid sequence of a modified soluble RSV F protein (subtype A) comprising to-tyrosine mutations at positions 77 (K77Y) and 222 (E222Y) (SEQ ID NO:17). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 15. Amino acid sequence of a modified soluble RSV F protein (subtype A) comprising to-tyrosine mutations at positions 88 (N88Y) and 255 (S255Y) (SEQ ID NO:18). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 16. Amino acid sequence of a modified soluble RSV F protein (subtype A) comprising to-tyrosine mutations at positions 97 (M97Y) and 159 (H159Y) (SEQ ID NO:19). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 17. Amino acid sequence of a modified soluble RSV F protein (subtype A) comprising to-tyrosine mutations at positions 185 (V185Y) and 427 (K427Y) (SEQ ID NO:20). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 18. Amino acid sequence of a modified soluble RSV F protein (subtype A) comprising to-tyrosine mutations at positions 187 (V187Y) and 427 (K427Y) (SEQ ID NO:21). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 19. Amino acid sequence of a modified soluble RSV F protein (subtype A) comprising to tyrosine mutations at positions 183 (N183Y) and 427 (K427Y) (SEQ ID NO:22). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 20A-20C. Sequence alignment of soluble RSV F protein subtype A (SEQ ID NO:1) and examples of modified RSV F proteins derived therefrom (SEQ ID NOS:11-21) comprising single or double to-tyrosine mutations. Tyrosines in boxes are introduced into the WT subtype A sequence. Where two new tyrosines are introduced into the same sequence, they are typically intended to cross-link with each other. Where only a single tyrosine is introduced, that tyrosine is typically expected to cross-link with an endogenous or pre-existing tyrosine in that sequence which is shown in bold and underlined. Amino acid residues 1-513 of each sequence are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 21. Amino acid sequence of a modified soluble RSV F protein (DS-Cav1) comprising a to-tyrosine mutation at position 147 (A147Y) (SEQ ID NO:23). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 22. Amino acid sequence of a modified soluble RSV F protein (DS-Cav1) comprising a to-tyrosine mutation at position 220 (V220Y) (SEQ ID NO:24). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 23. Amino acid sequence of a modified soluble RSV F protein (DS-Cav1) comprising a to-tyrosine mutation at position 222 (E222Y) (SEQ ID NO:25). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 24. Amino acid sequence of a modified soluble RSV F protein (DS-Cav1) comprising a to-tyrosine mutation at position 223 (F223Y) (SEQ ID NO:26). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 25. Amino acid sequence of a modified soluble RSV F protein (DS-Cav1) comprising a to-tyrosine mutation at position 226 (K226Y) (SEQ ID NO:27). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 26. Amino acid sequence of a modified soluble RSV F protein (DS-Cav1) comprising a to-tyrosine mutation at position 469 (V469Y) (SEQ ID NO:28). Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 27. Amino acid sequence of a modified soluble RSV F protein (subtype A) comprising to-tyrosine mutations at positions 222 (E222Y) and 469 (V469Y) (SEQ ID NO:29) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 28. Amino acid sequence of a modified soluble RSV F protein (subtype A) comprising to-tyrosine mutations at positions 226 (K226Y) and 469 (V469Y) (SEQ ID NO:30) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 29. Amino acid sequence of a modified soluble RSV F protein (DS-Cav1) comprising to-tyrosine mutations at positions 222 (E222Y) and 469 (V469Y) (SEQ ID NO:31) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIG. 30. Amino acid sequence of a modified soluble RSV F protein (DS-Cav1) comprising to-tyrosine mutations at positions 226 (K226Y) and 469 (V469Y) (SEQ ID NO:32) designed to facilitate the formation of multiple di-tyrosine cross-links. Amino acid residues 1-513 are the core sequences of the RSV F protein. The C-terminal sequences from amino acid residue 514 onwards comprise a foldon trimerization domain followed by a thrombin cleavage site, 6× His-tag (SEQ ID NO: 46), and a strep tag.

FIGS. 36A-36B. Sequence alignment of nucleotide sequences encoding the RSV F protein (full-length—with transmembrane and cytoplasmic domains) from RSV subtype A (SEQ ID NO:33—as "RSV_F_WT_Subtype_A" in the figure) and RSV subtype B (SEQ ID NO:34—identified as "RSV_F_WT_Subtype_B" in the figure). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 37. Nucleotide sequences encoding the RSV F protein (full-length—with transmembrane and cytoplasmic domains) from RSV subtype A that has been codon optimized for expression in human cells (SEQ ID NO:35). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 38. Nucleotide sequences encoding the RSV F protein (full-length—with transmembrane and cytoplasmic domains) from RSV subtype A that has been codon optimized for expression in hamster cells (such as CHO cells) (SEQ ID NO:36). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 39. Nucleotide sequences encoding the RSV F protein (full-length—with transmembrane and cytoplasmic domains) from RSV subtype A that has been codon optimized for expression in insect cells (such as SF9 insect cells) (SEQ ID NO:37). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 40. Nucleotide sequences encoding the RSV F protein (full-length—with transmembrane and cytoplasmic domains) from RSV subtype A that has been codon optimized for expression in mouse cells (SEQ ID NO:38). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 41. Nucleotide sequences encoding the RSV F protein (full-length—with transmembrane and cytoplasmic domains) from RSV subtype B that has been codon optimized for expression in human cells (SEQ ID NO:39). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 42. Nucleotide sequences encoding the RSV F protein (full-length—with transmembrane and cytoplasmic domains) from RSV subtype B that has been codon optimized for expression in hamster cells (such as CHO cells) (SEQ ID NO:40). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 43. Nucleotide sequences encoding the RSV F protein (full-length—with transmembrane and cytoplasmic domains) from RSV subtype B that has been codon optimized for expression in insect cells (such as SF9 insect cells) (SEQ ID NO:41). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 44. Nucleotide sequences encoding the RSV F protein (full-length—with transmembrane and cytoplasmic domains) from RSV subtype B that has been codon optimized for expression in mouse cells (SEQ ID NO:42). Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 45. Nucleotide sequences encoding the RSV F protein (full-length—with transmembrane and cytoplasmic domains) from RSV subtype A that has been codon optimized for expression in human cells and also comprises DS-CAV1 mutations (SEQ ID NO:43). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 46. Nucleotide sequences encoding the RSV F protein (full-length—with transmembrane and cytoplasmic domains) from RSV subtype A that has been codon optimized for expression in human cells and also comprises DS mutations (SEQ ID NO:44). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

FIG. 47. Nucleotide sequences encoding the RSV F protein (full-length—with transmembrane and cytoplasmic domains) from RSV subtype A that has been codon optimized for expression in human cells and also comprises CAV1 mutations (SEQ ID NO:45). The mutations are shown in bold and with boxes surrounding the mutated codons. Nucleotides 1-1539 encode amino acid residues 1-513, which are the core ectodomain sequences of the RSV F protein. Nucleotides 1540 onwards comprise sequences that encode the endogenous RSV F transmembrane region and cytoplasmic tail.

DETAILED DESCRIPTION OF THE INVENTION

Figure 31:
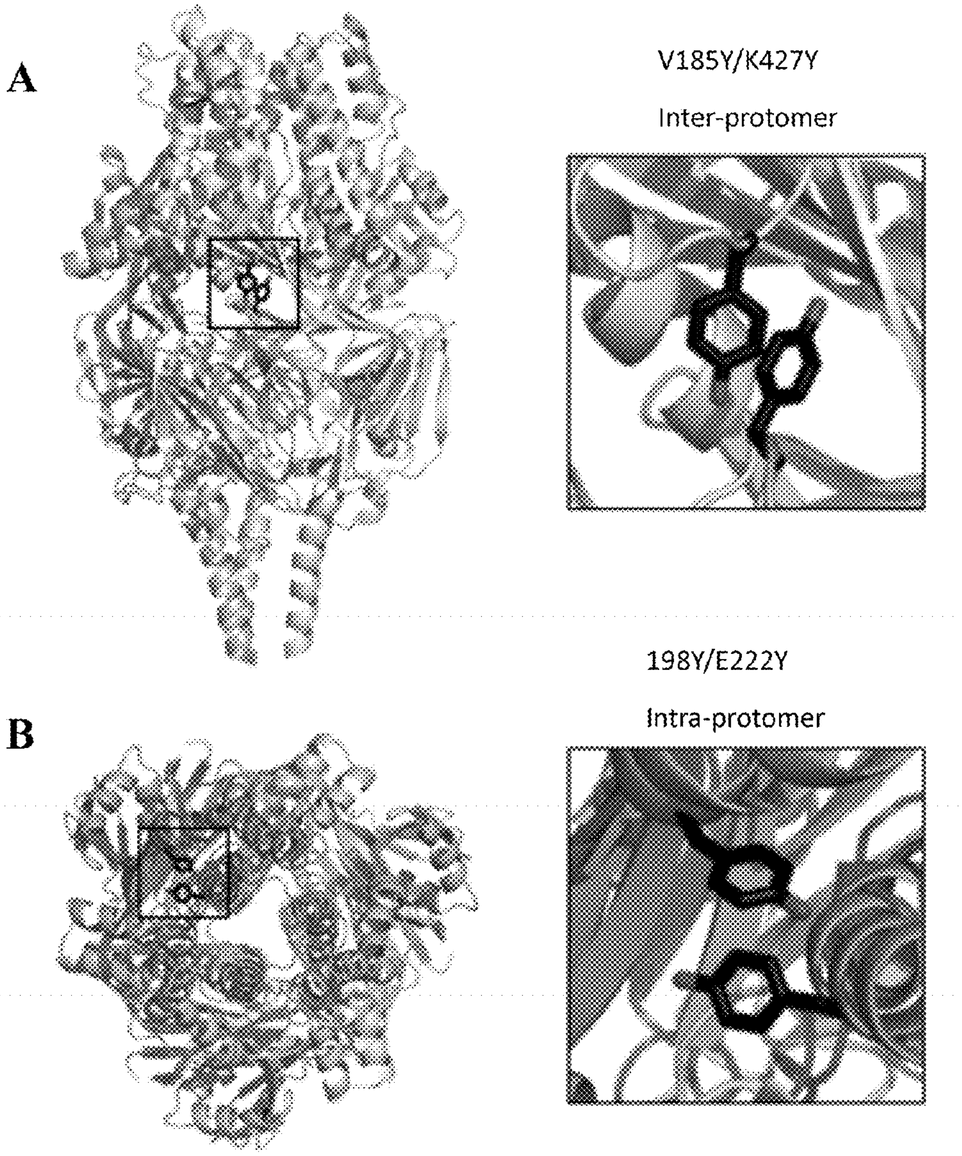
FIGS. 31A-31B. Ribbon diagrams depicting examples of two targeted positions in the RSV prefusion F protein trimer where intra-protomeric and intra-protomeric di-tyrosine cross-links can be introduced. (A) Side-view (and enlargement) of an engineered F1-F1 inter-protomeric di-tyrosine bond between a tyrosine introduced at position 185 (V185Y) and a tyrosine introduced at position 427 (K427Y) (SEQ ID NO:20). (B) Top-down view (and enlargement) of an engineered F1-F1 intra-protomeric di-tyrosine bond between an endogenous tyrosine at position 198 (198Y) and a tyrosine introduced at position 222 (E222Y) (SEQ ID NO:13). Targeted tyrosine residues are depicted in square boxes.

The present invention provides, in part, RSV F polypeptides, proteins and protein complexes, such as those that can be or are stabilized in a pre-fusion conformation, methods of making such polypeptides, proteins and protein complexes, compositions (such as pharmaceutical compositions and vaccine compositions) comprising such polypeptides, proteins and protein complexes, and methods of use of such polypeptides, proteins and protein complexes, for example in vaccination methods, therapeutic methods and other methods. In some embodiments, the RSV polypeptides, proteins and protein complexes may be useful as conformationally-specific immunogens, for example in RSV vaccines.

Definitions and Abbreviations

As used in the present specification the terms “about” and “approximately,” when used in relation to numerical values, mean within + or −20% of the stated value.

As used herein the terms “protein” and “polypeptide” are used interchangeably, unless otherwise stated. As used herein the term “protein complex” refers to an assembly of two or more proteins or protein subunits, such as two or more monomers or protomers. Unless otherwise stated, all description herein that relates to proteins applies equally to protein complexes, and vice versa.

As used herein the terms “stabilized” and “locked” are used interchangeably, for example in relation to the effect of cross-linking in stabilizing or locking the RSV F protein in its pre-fusion conformation. These terms do not require 100% stability. Rather these terms denote a degree of improved or increased stability. For example, in some embodiments, when the term “stabilized” is used in relation to a RSV F protein cross-linked in its pre-fusion conformation, the term denotes that the pre-fusion conformation has greater stability than it would have had prior to or without such cross-linking. Stability, and relative stability, may be measured in various ways as described in other sections of this application, for example based on the half-life of the RSV pre-fusion conformation. The improvement or increase in stability may be to any degree that is useful or significant for the intended application. For example, in some embodiments stability may be increased by about 10%, 25%, 50%, 100%, 200% (i.e. 2-fold), 300% (i.e. 3-fold), 400% (i.e. 4-fold), 500% (i.e. 5-fold), 1000% (i.e. 10-fold), or more.

RSV F Polypeptides, Proteins & Protein Complexes

The RSV Fusion or “F” protein is the envelope glycoprotein of respiratory syncytial viruses. The RSV F protein may be translated as a single polypeptide precursor in either a soluble (without the transmembrane domain) or membrane-bound (with the transmembrane domain) form. This polypeptide forms a trimer, which may, in some situations, be proteolytically cleaved by one or more cellular proteases at conserved furin consensus cleavage sites to yield two disulfide-bonded fragments known as the F1 (C-terminal) and F2 (N-terminal) fragments. The F2 fragment includes approximately the first 83 amimo acids of the RSV F precursor. Either the uncleaved precursor protein, or a heterodimer of the cleaved F2 and F1 fragments, can form an RSV F protomer. Three such protomers assemble to form the final RSV F protein complex, which is a homotrimer of three protomers.

Figure 32:
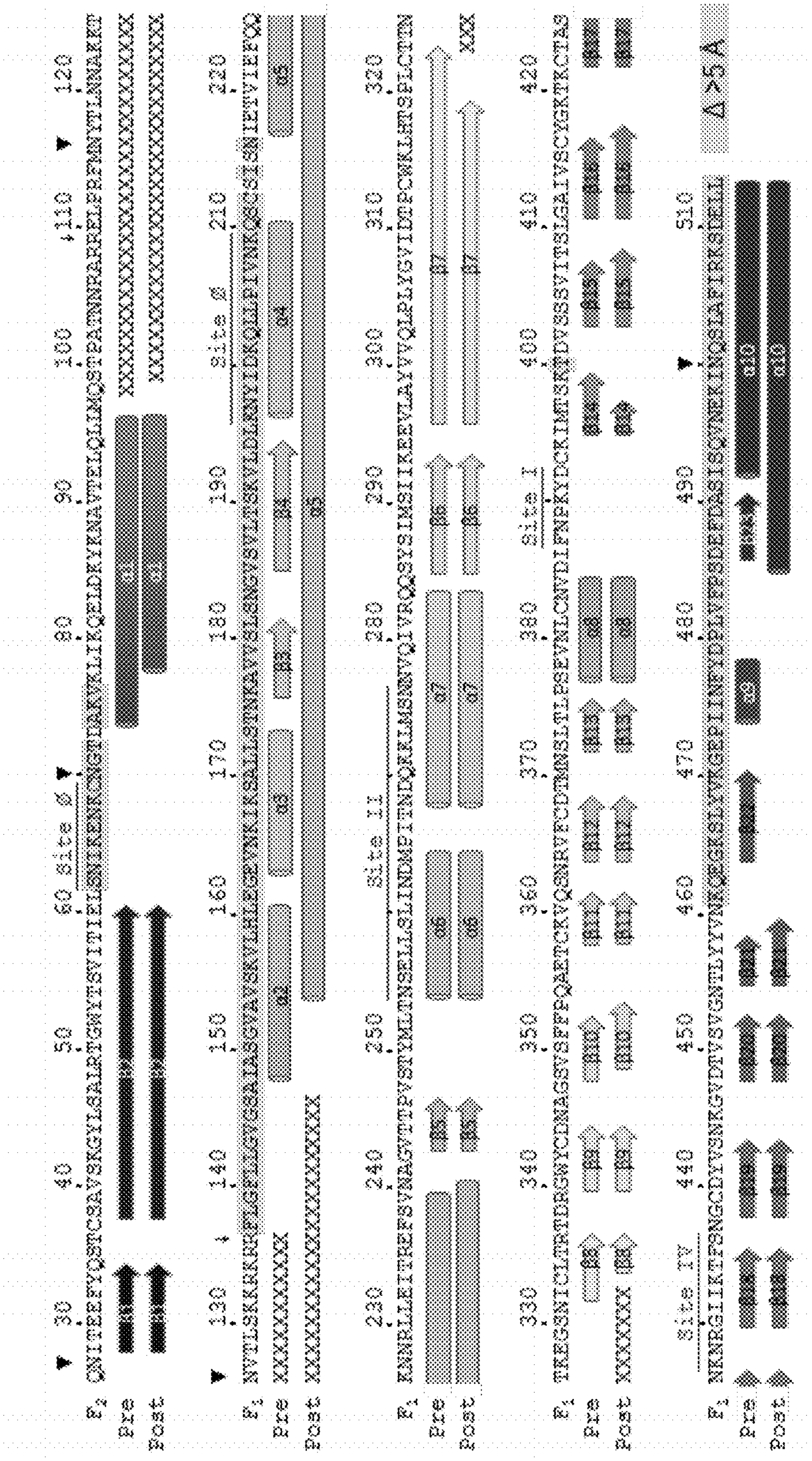
FIG. 32. Alignment of the RSV type A F protein sequence (SEQ ID NO: 47), and of the prefusion and post-fusion secondary structures. Cylinders and arrows below the sequence represent α-helices and β-strands, respectively. An "X" below the amino acid sequence indicates where the structure is disordered or missing. Gray shadowing indicates the position of residues that move more than 5 Å in the transition from the prefusion to postfusion conformation. Black triangles indicate sites of N-linked glycosylation, text and lines above the amino acid sequence indicate the antigenic sites, and arrows indicate the position of the furin cleavage sites. Figure from McLellan et al., 2013, Science 340:1113-1117, supplementary materials.

The RSV F protein trimer mediates fusion of viral and cellular membranes. The pre-fusion conformation of the RSV F protein trimer (which may be referred to herein as "pre-F") is highly unstable (metastable). However, once the RSV virus docks with the cell membrane, the RSV F protein trimer undergoes a series of conformational changes and transitions to a highly stable post-fusion ("post-F") conformation. The RSV F protein is known to induce potent neutralizing antibodies (nAbs) that correlate with RSV protection. For example, immunization with the RSV F protein induces nAbs that are protective in humans (e.g. Synagis). Several neutralizing epitopes (sites I, II and IV) are present on the post-fusion form of RSV F protein. Recently, however, Magro et al. showed that incubation of human sera with the RSV F protein in its post-fusion conformation failed to deplete the majority of neutralizing activity against the F protein, indicating the presence of neutralizing antigenic sites unique to the pre-fusion conformation (Magro et al. 2012, PNAS 109(8): 3089). By x-ray crystallography, the epitopes recognized by palivizumab (Synagis), motavizumab (Numax), and that of the more recently discovered 101F monoclonal antibody (McLellan et al., 2010, J. Virol., 84(23): 12236-441; and McLellan et al., 2010, Nat. Struct. Mol. Biol., February 17(2): 248-50) were mapped. Most recently, McLellan et al. (Science 340:1113-1117 (2013)) solved the structure of the F protein in its pre-fusion conformation, which revealed a novel neutralizing epitope—site ø—that is only displayed in the pre-fusion conformation, and to which a series of antibodies bind, e.g. 5C4, that are up to 50-fold more potently neutralizing than Synagis and Numax. Accordingly, there is mounting evidence that an RSV vaccine immunogen in this pre-fusion conformation and displaying site ø could elicit effective protection. However, to date the highly unstable (metastable) nature of the pre-fusion conformation of the RSV F protein has proved to be a significant barrier to the development of such a vaccine. Based on a comparison of the pre- and post-fusion RSV F structures of McLellan et al. there appear to be two regions of the F protein that undergo large conformational changes (>5 Å). These regions are located at the N- and C-termini of the F1 subunit (residues 137-216 and 461-513, respectively) (see FIG. 32). In the crystal structure of the RSV F protein held in its pre-fusion conformation by the D25-antibody bound to the site ø epitope, the C-terminal F1 residues can be stabilized in the pre-fusion conformation by appending a foldon trimerization domain. To stabilize the N-terminal region of F1, McLellan et al. found that binding of the antibody D25 was sufficient for crystallographic studies. However, for production of a vaccine immunogen alternative stabilization strategies are needed, such as those that do not require the RSV F protein to be bound to a large antibody molecule. One alternative approach that has been attempted involved the introduction of paired cysteine mutations (for disulfide bond formation) and cavity-filling mutations near the F1 N-terminus (see the DS-Cav1 RSV F protein variant described in McLellan et al. (2013) Science 342:592-598, which is hereby incorporated by reference in its entirety). However, crystallographic analysis of such variants revealed that the structure was only partially in the pre-fusion conformation. Accordingly, additional engineering of the RSV F protein is needed in order to achieve an immunogen for clinical vaccine development.

The present invention provides certain alternative approaches for stabilizing the RSV F protein in its pre-fusion conformation, including providing specific locations within the RSV F protein that can be or should be cross-linked, and providing mutant forms of the RSV F protein that can facilitate the formation of such cross-links. Such cross-links and mutations can be used alone (e.g. in the context of a wild type RSV F protein or in the context of a RSV F protein that does not comprise any man made mutations or other man made modifications), or can be used in combination with one or more other man made mutations, modifications, cross-links, or stabilization strategies. Thus, for example, the approaches described herein can be used in conjunction with the use of added foldon trimerization domains, stabilizing antibodies (such as D25), and/or other partially or potentially stabilizing modifications or mutations—such as those in the DS-Cav1 RSV F protein variant described by McLellan et al.

The present inventors have performed extensive analysis of the structure of the RSV F protein and have developed a variety of novel design strategies and novel engineered RSV F polypeptides, proteins and protein complexes. The present invention also provides methods for making and using such RSV F polypeptides, proteins, and protein complexes. In some embodiments, the present invention provides specific locations within the amino acid sequence of the RSV F protein at which, or between which, targeted cross-links can be made in order to "lock" the RSV F protein in its pre-F conformation. In some embodiments, the targeted cross-links are di-tyrosine cross-links. Where di-tyrosine cross-links are used, the present invention provides specific amino acid residues (or pairs of amino acid residues) that either comprise a pre-existing tyrosine residue or can be or are mutated to a tyrosine residue such that di-tyrosine cross-links can be made.

Throughout the present patent specification, when reference is made to specific amino acid residues or specific amino acid regions in the RSV F protein by referring to their amino residue number or numbers (such as amino acid residues 77, 88, 97, or 222, for example), and unless otherwise stated, the numbering is based on the RSV amino acid sequences provided herein in the sequence listing and in the Figures (see, for example, FIG. 6 and SEQ ID NO: 1). However, it should be noted, and one of skill in the art will understand, that different RSV sequences may have different numbering systems, for example, if there are additional amino acid residues added or removed as compared to SEQ ID NO: 1. As such, it is to be understood that when specific amino acid residues are referred to by their number, the description is not limited to only amino acids located at precisely that numbered position when counting from the beginning of a given amino acid sequence, but rather that the equivalent/corresponding amino acid residue in any and all RSV F sequences is intended—even if that residue is not at the same precise numbered position, for example if the RSV sequence is shorter or longer than SEQ ID NO. 1, or has insertions or deletions as compared to SEQ ID NO. 1. One of skill in the art can readily determine what is the corresponding/equivalent amino acid position to any of the specific numbered residues recited herein, for example by aligning a given RSV F sequence to SEQ ID NO. 1 or to any of the other RSV F amino acid sequences provided herein.

The present invention provides RSV F protein and polypeptide amino acid sequences, and compositions and methods comprising such sequences. However, the invention is not limited to the specific RSV F sequences disclosed herein. Rather the present invention contemplates variations, modifications and derivatives of the specific sequences provided herein.

In some embodiments, the RSV F polypeptides, proteins or protein complexes of the present invention can be derived from (or can comprise, consist essentially of, or consist of) the amino acid sequences of any suitable RSV F polypeptide, protein or protein complex sequence known in the art, including, without limitation: the amino acid sequence of RSV subtype A (for example in soluble form (SEQ ID NO:1, or amino acid residues 1-513 thereof) or in a full-length form (SEQ ID NO:2)); the amino acid sequence of RSV subtype B (for example in soluble form (SEQ ID NO:3, or amino acid residues 1-513 thereof) or in full-length form (SEQ ID NO:4)); the amino acid sequence of RSV variant DS-Cav1 (for example in soluble form (SEQ ID NO:5, or amino acid residues 1-513 thereof) or in full-length form (SEQ ID NO:6)); the amino acid sequence of RSV variant Cav1 (for example in soluble form (SEQ ID NO:7, or amino acid residues 1-513 thereof) or in full-length form (SEQ ID NO:8)); or the amino acid sequence of RSV variant DS (for example in soluble form (SEQ ID NO:9, or amino acid residues 1-513 thereof) or in full-length form (SEQ ID NO:10)), or any fragment thereof. In some embodiments, the RSV F proteins and polypeptides of the present invention can be derived from (or can comprise, consist essentially of, or consist of) amino acid sequences that have at least about 60%, 65%, 70%, 75%, 80%, 85%, 90%, 95%, 98%, or 99% sequence identity to any known RSV F sequences or RSV F ectodomain sequences (including but not limited to amino acid residues 1-513 of SEQ ID NOs:1-10, or SEQ ID NOs:1-10), or to RSV F sequences from any known RSV groups, subgroups, families, subfamilies, types, subtypes, genera, species, strains, and/or clades, or any fragment thereof. It should be noted that amino acid residues 1-513 of the various RSV F sequences provided herein are core RSV F ectodomain sequences. Amino acid residues 514 onwards in all such sequences comprise additional domains that may be present in some embodiments but not in others. In some embodiments variants of such additional domains may be present. For example, amino acid residues 514 onwards in all soluble RSV F sequences provided herein comprise an optional foldon trimerization domain, thrombin cleavage site, 6× His-tag (SEQ ID NO: 46), and a strep tag. In some embodiments these additional sequences may be absent, modified, rearranged or replaced. For example, in some embodiments different trimerization domains may be used, or different epitope tags may be used. Similarly, amino acid residues 514 onwards in all "full-length" or membrane-bound RSV F sequences provided herein comprise an optional RSV F protein transmembrane region and cytoplasmic tail. In some embodiments these additional sequences may be absent, modified, rearranged or replaced, for example with different transmembrane or cytoplasmic domains.

In some embodiments the present invention provides RSV F polypeptides, proteins, and/or protein complexes that comprise one or more artificially-introduced cross-links, wherein at least one of the following amino acid residues within the RSV F polypeptides, proteins, and/or protein complexes is artificially cross-linked to another amino acid residue in the RSV F protein: Y33, K77, N88, M97, A147, 5150, 5155, H159, N183, V185, V187, Y198, V220, E222, F223, K226, 5255, Y286, K427 and V469. In some such embodiments the cross-link is a di-tyrosine cross-link.

In some embodiments the present invention provides RSV F polypeptides, proteins, and/or protein complexes that comprise one or more artificially-introduced cross-links, wherein such artificially introduced cross-links connect two of the following amino acid residues: Y33, K77, N88, M97, A147, 5150, 5155, H159, N183, V185, V187, Y198, V220, E222, F223, K226, S255, Y286, K427 and V469. In some such embodiment the cross-link is a di-tyrosine cross-link.

In some embodiments the present invention provides RSV F polypeptides, proteins, and/or protein complexes in which the amino acid residues in one or more of the following pairs of amino residues are cross-linked to each other by an artificially introduced cross-link: 147/286, 198/220, 198/222, 198/223, 198/226, 33/496, 77/222, 88/255, 97/159, 183/427, 185/427, and 187/427. In some such embodiments the cross-link is a di-tyrosine cross-link.

In some embodiments the present invention provides RSV F polypeptides, proteins, and/or protein complexes comprising an artificially introduced cross-link between two of the following regions: the F1 mobile N-terminus (residues 137-216), α2 (residues 148-160), α3 (residues 163-173), β3 (residues 176-182), β4 (residues 186-195), α4 (residues 197-211), the F1 mobile C-terminus (residues 461-513), β22 (residues 464-471), α9 (residues 474-479), β23 (residues 486-491), and α10 (residues 493-514). In some such embodiments the cross-link is a di-tyrosine cross-link.

In some embodiments the present invention provides RSV F polypeptides, proteins, and/or protein complexes comprising an artificially introduced cross-link between two of the following regions: amino acid residues from about position 67 to about position 87, amino acid residues from about position 78 to about position 98, amino acid residues from about position 87 to about position 107, amino acid residues from about position 137 to about position 157, amino acid residues from about position 140 to about position 160, amino acid residues from about position 145 to about position 165, amino acid residues from about position 149 to about position 169, amino acid residues from about position 173 to about position 193, amino acid residues from about position 175 to about position 195, from about position 177 to about position 197, amino acid residues from about position 188 to about position 208, amino acid residues from about position 210 to about position 230, amino acid residues from about position 212 to about position 232, amino acid residues from about position 213 to about position 233, amino acid residues from about position 216 to about position 236, amino acid residues from about position 245 to about position 265, amino acid residues from about position 276 to about position 296, amino acid residues from about position 417 to about position 437, and amino acid residues from about position 459 to about position 479. In some such embodiments the cross-link is a di-tyrosine cross-link.

In embodiments where the RSV F polypeptides, proteins, and/or protein complexes of the invention comprise one or more di-tyrosine cross-links, di-tyrosine cross-links may be introduced between two endogenous tyrosine residues, between two tyrosine residues originating from "to-tyrosine" mutations, or between a tyrosine residue originating from a "to-tyrosine" mutation and an endogenous tyrosine residue. In some embodiments, more than one di-tyrosine cross-link is introduced into a RSV F protein or polypeptide.

In embodiments where the RSV F polypeptides, proteins, and/or protein complexes of the invention comprise one or more di-tyrosine cross-links, non-limiting examples of amino acid positions where a "to-tyrosine" mutation can be introduced include K77, N88, M97, A147, S150, S155, H159, N183, V185, V187, V220, E222, F223, K226, S255, K427 and V469 (see FIG. 6), or any combination thereof.

In embodiments where the RSV F polypeptides, proteins, and/or protein complexes of the invention comprise one or more di-tyrosine cross-links, non-limiting examples of pre-existing or endogenous tyrosine residues that can be used to form a di-tyrosine cross-link include Y33, Y198 and Y286 (see FIG. 6), or any combination thereof.

In embodiments where the RSV F polypeptides, proteins, and/or protein complexes of the invention comprise one or more di-tyrosine cross-links, non-limiting examples of residue pairs between which a di-tyrosine cross-link can be introduced include 147/286, 198/220, 198/222, 198/223, 198/226, 33/496, 77/222, 88/255, 97/159, 183/427, 185/427, and 187/427, or any combination thereof.

In embodiments where the RSV F polypeptides, proteins, and/or protein complexes of the invention comprise one or more di-tyrosine cross-links, non-limiting examples of regions or secondary structures of the RSV F protein from which amino acids may be selected for tyrosine substitution and/or di-tyrosine cross-linking include the F1 mobile N-terminus (residues 137-216), α2 (residues 148-160), α3 (residues 163-173), β3 (residues 176-182), β4 (residues 186-195), α4 (residues 197-211), the F1 mobile C-terminus (residues 461-513), β22 (residues 464-471), α9 (residues 474-479), β23 (residues 486-491), and α10 (residues 493-514). Non-limiting examples of other regions of RSV F protein from which one or more amino acids may be selected for tyrosine substitution and/or cross-linking include residues from about position 67 to about position 87, from about position 78 to about position 98, from about position 87 to about position 107, from about position 137 to about position 157, from about position 140 to about position 160, from about position 145 to about position 165, from about position 149 to about position 169, from about position 173 to about position 193, from about position 175 to about position 195, from about position 177 to about position 197, from about position 188 to about position 208, from about position 210 to about position 230, from about position 212 to about position 232, from about position 213 to about position 233, from about position 216 to about position 236, from about position 245 to about position 265, from about position 276 to about position 296, from about position 417 to about position 437, and from about position 459 to about position 479.

In some embodiments, the present invention provides RSV F polypeptides, proteins, and/or protein complexes that are derived from, comprise, consist essentially of, or consist of, the amino acid sequence of SEQ ID NO:11, 12, 13, 14, 15, 16, 17, 18, 19, 20, 21, 22, 23, 24, 25, 26, 27, 28, 29, 30, 31, or 32, or amino acid residues 1-513 thereof, (each of which are mutants of the RSV F amino acid sequence that comprise one or more "to tyrosine" mutations to facilitate di-tyrosine cross-linking and to facilitate "locking" of the RSV F protein in its pre-F conformation), or any fragment thereof, such as fragments comprising amino acid residues 1-513 thereof, and/or fragments comprising the F1 or F2 fragments of the RSV F protein, or any other fragments of the RSV F protein that may be generated proteolytically and/or that may be assembled into or form part of a functional RSV F protein. In some embodiments, the present invention provides RSV F polypeptides, proteins, and/or protein complexes that are derived from, comprise, consist essentially of, or consist of, an amino acid sequence having at least about 75%, 80%, 85%, 90%, 95%, 98%, or 99% sequence identity to SEQ ID NO: 11, 12, 13, 14, 15, 16, 17, 18, 19, 20, 21, 22, 23, 24, 25, 26, 27, 28, 29, 30, 31, or 32, or amino acid residues 1-513 thereof, or any fragment thereof.

Non-limiting examples of amino acid positions in an RSV F protein or polypeptide to which di-tyrosine cross-links may be targeted include Y33 (pre-existing Tyr residue) and V469Y (to-Tyr substitution), where a F2-F1 intra-protomer bond will form, the positions Y198 (pre-existing Tyr residue) and E222Y (to-Tyr substitution), where an F1-F1 intra-molecular bond would form, the positions K77Y (to-Tyr substitution) and E222Y (to-Tyr substitution), where an $F_2$-$F_1$ inter-protomer bond would form, the positions N88Y (to-Tyr substitution) and S255Y (to-Tyr substitution), where an $F_2$-$F_1$ inter-protomer bond would form, the positions M97Y (to-Tyr substitution) and H159Y (to-Tyr substitution), where an $F_2$-$F_1$ inter-protomer bond would form, the positions V185Y (to-Tyr substitution) and K427Y (to-Tyr substitution), where an $F_1$-$F_1$ inter-protomer bond would form, and the positions N183Y (to-Tyr substitution) and K427Y (to-Tyr substitution), where an $F_1$-$F_1$ inter-protomer bond would form. These positions were initially identified by analysis of the atomic level structure of the RSV prefusion F protein. Further non-limiting examples include positions A147Y (to-Tyr substitution) and Y286 (pre-existing Tyr), Y198 (pre-existing Tyr residue) and V220Y (to-Tyr substitution), Y198 (pre-existing Tyr residue) and F223Y (to-Tyr substitution), Y198 (pre-existing Tyr residue) and K226Y (to-Tyr substitution), V187Y (to-Tyr substitution) and K427Y (to-Tyr substitution) and N88Y (to-Tyr substitution) and S255Y (to-Tyr substitution). In some embodiments, the RSV polypeptides, proteins or protein complexes of the invention comprise one of the above listed di-tyrosine cross-links. In some embodiments, the RSV polypeptides, proteins or protein complexes of the invention comprise two of the above listed di-tyrosine cross-links. In some embodiments, the RSV polypeptides, proteins or protein complexes of the invention comprise three of the above listed di-tyrosine cross-links. In some embodiments, the RSV polypeptides, proteins or protein complexes of the invention comprise four of the above listed di-tyrosine cross-links. In some embodiments, the RSV polypeptides, proteins or protein complexes of the invention comprise five or more of the above listed di-tyrosine cross-links. In some embodiments, the RSV polypeptides, proteins or protein complexes of the invention comprise any combination or one or more of the above listed di-tyrosine cross-links.

Non-limiting examples of RSV F proteins designed to have more than one di-tyrosine cross-link include RSV F proteins with two "to-tyrosine" mutations (E222Y/V469Y), for example, derived from subtype A (SEQ ID NO:29) or DS-Cav1 (SEQ ID NO:31) where the tyrosine substituted at position 222 is designed to pair with the endogenous tyrosine at position 198, and the tyrosine substituted at position 469 is designed to pair with the endogenous tyrosine at position 33, thus stabilizing the RSV F protein by the formation of two di-tyrosine cross-links; and RSV F proteins with two to-tyrosine mutations (K226Y/V469Y), for example, derived from subtype A (SEQ ID NO:30) or DS-Cav1 (SEQ ID NO:32) where the tyrosine substituted at position 226 is designed to pair with the endogenous tyrosine at position 198, and the tyrosine substituted at position 469 is designed to pair with the endogenous tyrosine at position 33, thus stabilizing the F protein by the formation of two di-tyrosine cross-links.

As described above, each protomer of the mature RSV F trimer may be cleaved into two distinct polypeptide chains termed F1 and F2 which associate non-covalently to form a protomer. A bond between a F1 polypeptide and a F2 polypeptide within the same protomer is an example of an inter-molecular bond and an intra-protomer bond. The invention provides exemplary RSV F proteins and polypeptides comprising cross-links designed to stabilize this interaction, including without limitation, SEQ ID NO:16 (V469Y, where the introduced tyrosine at position 469 is designed to pair with endogenous tyrosine 33), SEQ ID NO:17 (K77Y/E222Y, designed to form a di-tyrosine pair between the introduced tyrosines), SEQ ID NO:18 (N88Y/S255Y, designed to form a di-tyrosine pair between the introduced tyrosines), and SEQ ID NO:19 (M97Y/H159Y, designed to form a di-tyrosine pair between the introduced tyrosines), as well as RSV F polypeptides, proteins or protein complexes derived from such sequences and including the specific "to tyrosine" mutations present in such sequences. The invention also provides exemplary RSV F proteins and polypeptides comprising cross-links designed to hold two protomers of the trimer together (inter-molecular, inter-protomer bond), including without limitation, SEQ ID NO:20 (V185Y/K427Y), SEQ ID NO:21 (V187Y/K427Y) SEQ ID NO:22 (N183Y/K427Y), as well as RSV F polypeptides, proteins or protein complexes derived from such sequences and including the specific "to tyrosine" mutations present in such sequences. In each of these proteins, one introduced tyrosine in one protomer is designed to pair with the other introduced tyrosine on the adjacent protomer. For example, in SEQ ID NO:20 (V185Y/K427Y), the tyrosine at position 185 on "protomer A" would form a di-tyrosine bond with the tyrosine at position 427 on "protomer B" (see FIG. 31A).

In some embodiments, the F1 polypeptide of a RSV F protein is cross-linked with the F2 polypeptide of the same protomer (inter-molecular/intra-protomer bond). In some embodiments, the F1 polypeptide is intra-molecularly cross-linked (e.g., both tyrosines of the cross-link are located within the same F1 polypeptide). In some embodiments, the F2 polypeptide is intra-molecularly cross-linked (e.g., both tyrosines of the cross-link are located within the same F1 polypeptide). In some embodiments, the F1 polypeptide of the RSV prefusion F protein is cross-linked with the F1 polypeptide of an adjacent protomer (inter-protomer bond). In some embodiments, the F1 polypeptide of the RSV prefusion F protein is cross-linked with the F2 polypeptide of an adjacent protomer (inter-protomer bond).

The transition from the pre-F to the post-F structures involves very significant rearrangement of parts of the RSV protein, in particular the C- and N-termini of $F_1$, while the rest of the protein moves significantly less. In order to stabilize the preF conformation by the methods of this invention, parts of the protein that move significantly (e.g. more than 5 Å) can be attached to parts of the protein that move less significantly (e.g. less than 5 Å), either between two residues of the $F_1$ chain of a single protomer, between two residues of the $F_2$ chain of single protomer, between one residue of the $F_1$ chain and one residue of the $F_2$ chain within the same protomer, or between $F_1$ and/or $F_2$ residues of two adjacent protomers. Alternatively, parts of the protein that move significantly (e.g. more than 5 Å) can be attached to other parts of the protein that also move significantly (e.g. more than 5 Å), also either between two residues of the $F_1$ chain, between two residues of the $F_2$ chain, between one residue of the $F_1$ chain and one residue of the $F_2$ chain of within the same protomer, or between $F_1$ and/or $F_2$ residues of two adjacent protomers. Covalent attachment of moving parts to either moving or non-moving parts prevents the transition from the prefusion structure to either intermediate structures or to the postfusion structure.

Positions in F2 that move more than 5 Å in the pre-fusion to post-fusion transition include the positions 62 through 76, whereas positions 26 through 61 and 77 through 97 move less than 5 Å (and positions 98-109 have yet to be determined in the pre-fusion structure). Positions in F1 that move more than 5 Å in the pre-F to post-F transition include the positions 137 through 216 (F1 mobile N-terminus) and 461 through 513 (F1 mobile C-terminus). The F1 mobile N-terminus of the preF structure further comprises the 2 (positions 148 through 173), 3 (positions 176 through 182), and 4 (positions 197 through 211) secondary structures that can each either be attached to one another, or to other moving or non-moving parts within the same protomer or between protomers of the F protein trimer (complex consisting of three protomers). The F1 mobile C-terminus of the preF structure further comprises the 22 (positions 464 479), 3 (positions 486 t structures that can each either be attached to one another, or to other moving or non-moving parts within the same protomer or between protomers of the F protein trimer. (See FIG. 32.)

In some embodiments (including all of those described above, and those involving RSV F polypeptides, proteins, and/or protein complexes having any of the specific amino acid sequences recited herein, and those involving variants or fragments of such RSV F polypeptides, proteins, and/or protein complexes having less than 100% identity to the specific amino acid sequence provided herein), the RSV F polypeptides, proteins, and/or protein complexes of the invention should have one or more desired properties such as being capable of (1) forming the pre-F conformation, (2) being "locked" in the pre-F conformation by cross-linking, (3) binding to a pre-F specific antibody, (4) binding to an antibody that binds to site ø, (5) binding to a neutralizing antibody, (6) binding to a broadly neutralizing antibody, (7) binding to an antibody selected from the group consisting of D25, AM22, 5C4, 101F (8) binding to palivizumab (Synagis), (9) binding to and/or activating a B cell receptor, (10) eliciting an antibody response in an animal, (11) eliciting a protective antibody response in an animal, (12) eliciting production of neutralizing antibodies in an animal, (13) eliciting production of broadly neutralizing antibodies in an animal, (14) eliciting production of antibodies that recognize quaternary neutralizing epitopes (QNEs) in an animal, and/or (15) eliciting a protective immune response in an animal.

Unless otherwise stated, all description herein that relates to specific RSV F polypeptides, proteins, and protein complexes, relates equally to all homologs, orthologs, analogs, derivatives, mutant forms, fragments, chimeras, fusion proteins etc. thereof, such as those that have certain desired properties or features (for example those that are in the pre-F conformation, or that are capable of forming part of a complex having the desired pre-F conformation, or that have desired functional properties, including, but not limited to, being capable of binding to, or eliciting the production of, one or more anti-RSV antibodies, such as antibodies that are specific to the RSV pre-F conformation and/or that bind to the ø site).

Similarly, all description herein that relates to specific polypeptides, proteins, and/or protein complexes polypeptides, proteins, and/or protein complexes (e.g. those having specific amino acid sequences or those from a specific RSV type, subtype, or strain) relates equally to other related forms of such polypeptides, proteins, and/or protein complexes that may exist in nature (for example in different RSV types, subtypes or strains) or that are related to the specific sequences provides herein but have been altered artificially in some way, such as by recombinant means, chemical means, or any other means. The polypeptides, proteins, and/or protein complexes described herein can have, or can be derived from, the nucleotide and/or amino acid sequences of any suitable RSV polypeptides, proteins, and/or protein complexes known in the art. In some embodiments, the RSV F polypeptides, proteins, and/or protein complexes of the invention may be, or may be derived from, derivatives and/or analogs of specific RSV F polypeptides, proteins, and/or protein complexes described herein or known in the art, including proteins that are substantially homologous to any such proteins, or fragments thereof (e.g., in various embodiments, those having at least about 40% or 50% or 60% or 70% or 75% or 80% or 85% or 90% or 95% or 98% or 99% identity with an amino acid or nucleic acid sequence of any specific RSV F polypeptides, proteins, and/or protein complexes described herein or known in the art, when aligned using any suitable method known to one of ordinary skill in the art, such as, for example, using a computer homology program known in the art) or whose encoding nucleic acid is capable of hybridizing to a coding nucleic acid sequence of a protein of the invention, under high stringency, moderate stringency, or low stringency conditions.

In some embodiments, the invention provides fragments of the specific RSV F polypeptides, proteins, and protein complexes described herein, such as those comprising, consisting essentially of, or consisting of, at least about 10 amino acids, 20 amino acids, 50 amino acids, 100 amino acids, 200 amino acids, or 500 amino acids.

In some embodiments one or more amino acid residues within a specific RSV F polypeptide, protein, and/or protein complex as described herein, or as known in the art, can be deleted, added, or substituted with another amino acid. In embodiments where such mutations are introduced, the RSV F polypeptides, proteins, or protein complexes can be microsequenced to determine a partial amino acid sequence. In other embodiments the nucleic acid molecules encoding the RSV F polypeptides, proteins, and/or protein complexes can be sequenced to identify and/or confirm the introduction of mutations.

In some embodiments, one or more amino acid residues can be substituted by another amino acid having a similar polarity and that may acts as a functional equivalent, resulting in a silent alteration. In some embodiments substitutions for an amino acid within the sequence may be selected from other members of the class to which the amino acid belongs e.g. to create a conservative substitution. For example, the nonpolar (hydrophobic) amino acids include alanine, leucine, isoleucine, valine, proline, phenylalanine, tryptophane and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In some embodiments artificial, synthetic, or non-classical amino acids or chemical amino acid analogs can be used to make the RSV F polypeptides, proteins, and/or protein complexes of the invention. Non-classical amino acids include, but are not limited to, the D-isomers of the common amino acids, fluoro-amino acids, and "designer" amino acids such as β-methyl amino acids, Cγ-methyl amino acids, Nγ-methyl amino acids, and amino acid analogs in general. Additional non-limiting examples of non-classical amino acids include, but are not limited to: α-aminocaprylic acid, Acpa; (S)-2-aminoethyl-L-cysteine/HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cysteic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-flurophenylalanine, Fphe; D-glucoseaminic acid, Gaa; homoarginine, Hag; δ-hydroxylysine/HCl, Hlys; DL-β-hydroxynorvaline, Hnvl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl) alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3-trifluroalanine, Tfa; 6-hydroxydopa, Thphe; L-vinylglycine, Vig; (−)-(2R)-2-amino-3-(2-aminoethylsulfonyl) propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (−)-(2R)-2-amino-3-(2-hydroxyethylsulfonyl) propanoic acid, Ahsopa; (−)-(2R)-2-amino-3-(2-hydroxyethylsulfanyl) propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (S)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al., 1998 (Sandberg et al., 1998. New chemical descriptors relevant for the design of biologically active peptides. A multivariate characterization of 87 amino acids. J Med Chem 41(14): pp. 2481-91).

Nucleic Acids

In addition to providing certain RSV F polypeptides, proteins, and/or protein complexes, as described herein, the present invention also provides nucleic acids encoding such RSV F polypeptides, proteins, and/or protein complexes, and compositions and vectors comprising such nucleic acids. Such nucleic acids can be obtained or made using any suitable method known in the art. For example, nucleic acid molecules encoding RSV F polypeptides, proteins, and/or protein complexes may be obtained from cloned DNA or made by chemical synthesis. In some embodiments the nucleic acids may be obtained by reverse transcribing RNA prepared by any of the methods known to one of ordinary skill in the art, such as random- or poly A-primed reverse transcription. Whatever the source, a nucleic acid molecule encoding a RSV F polypeptide, protein, and/or protein complex of the present invention can be cloned into any suitable vector, such as those to be used for propagation of the nucleic acid molecule or those to be used for expression of the nucleic acid molecule. The nucleic acid may be cleaved at specific sites using various restriction enzymes, if needed. In embodiments requiring expression, the nucleic acid can be operatively linked to a promoter suitable for directing expression in the desired cell type, such as a mammalian cell or an insect cell, and may be incorporated into any suitable expression vector, such as a mammalian or insect expression vector.

In some embodiments, the RSV F polypeptides, proteins or protein complexes of the present invention can derived from nucleic sequences that encode (or that comprise, consist essentially of, or consist of nucleotide sequences that encode) any suitable RSV F polypeptide, protein or protein complex sequence known in the art, or any fragment thereof, including, without limitation: a nucleotide sequence that encodes the wild-type (WT) full length F protein from RSV subtype A (for example, SEQ ID NO:33), or a nucleotide sequence that encodes the wild-type (WT) full length F protein from RSV subtype B (for example, SEQ ID NO:34), or variants of such sequences that have been codon optimized for expression in cells of any particular species of interest, or that contain any mutations of interest. For example, in some embodiments, the RSV F polypeptides, proteins or protein complexes of the present invention can derived from nucleotide sequences that encode the F protein of RSV F type A, but that have been codon optimized for expression in human (e.g. SEQ ID NO:35), hamster (e.g. SEQ ID NO:36), insect (e.g. SEQ ID NO:37), or mouse cells (e.g. SEQ ID NO:38), or optimized for expression in any other cell type. Similarly, in some embodiments, the RSV F polypeptides, proteins or protein complexes of the present invention can derived from nucleotide sequences that encode the F protein of RSV F type B, but that have been codon optimized for expression in human (e.g. SEQ ID NO:39), hamster (e.g. SEQ ID NO:40), insect (e.g. SEQ ID NO:41), or mouse cells (e.g. SEQ ID NO:42), or optimized for expression in any other cell type. Similarly, in some embodiments, the RSV F polypeptides, proteins or protein complexes of the present invention can derived from nucleotide sequences that encode the F protein of RSV F type A or B, and which may or may not have been codon optimized for expression cells of any given species of interest, and which also comprise one or more other mutations of interest. For example, in some embodiments, the RSV F polypeptides, proteins or protein complexes of the present invention can be derived from nucleotide sequences that comprise DS-CAV1 (SEQ ID NO:43), DS (SEQ ID NO: 44), and/or CAV1 (SEQ ID NO:45) mutant sequences. Although the three specific sequences provided in SEQ ID NO:s 43, 44, and 45 comprise the DS, CAV1, and DS-CAV1 mutations in the context of a human codon optimized full-length RSV type A sequence, such mutations, or indeed any other mutations of interest (including all of the "to-tyrosine" mutations of the invention), could equally be present in a backbone of any other suitable RSV type A or type B sequence, including, but not limited to, those sequences that have been optimized for expression in any species of interest, or that include any mutations of interest, or that include only certain portions of the RSV type A or B sequences, such as, for example, only nucleotides 1-1539 that encode only the RSV F ectodomain (without the transmembrane and/or cytoplasmic domains). One of skill in the art will recognize that there are a variety of nucleotide sequences that can encode the various RSV F polypeptides and proteins described herein, and all such nucleotide sequences are intended to fall within the scope of the present invention. For example, in some embodiments, the RSV F proteins and polypeptides of the present invention can be derived from nucleotide sequences that have at least about 60%, 65%, 70%, 75%, 80%, 85%, 90%, 95%, 98%, or 99% sequence identity to any known nucleotide sequences that encode an RSV F protein, including, but not limited to, any of those illustrated herein (including SEQ ID NOs: 33, 34, 35, 36, 37, 38, 39, 40, 41, 42, 43, 44, and 45), or that have at least about 60%, 65%, 70%, 75%, 80%, 85%, 90%, 95%, 98%, or 99% sequence identity to nucleotides 1-1539 thereof (which encode the ectodomain sequences), or that have at least about 60%, 65%, 70%, 75%, 80%, 85%, 90%, 95%, 98%, or 99% sequence identity to nucleotide sequences that encode RSV F proteins from any known RSV groups, subgroups, families, subfamilies, types, subtypes, genera, species, strains, and/or clades, or any fragment thereof.

Furthermore, one or skill in the art can readily visualize, or make, nucleic acid molecules that comprise any one or more of the specific "to-tyrosine" mutations described herein, for example, by locating the nucleotide codon that encodes the specific amino acid residue to be mutated, and mutating the nucleotides at that codon as necessary to result in a tyrosine-encoding codon.

Cross-Linking

In some embodiments the RSV F polypeptides and/or proteins of the invention are assembled into protein complexes having a desired conformational structure, such as the pre-F conformation, and are cross-linked in order to stabilize that conformation. Details of particular regions of the RSV F protein that can be cross-linked, as well as particular RSV mutants designed to facilitate such cross-linking, are described in other sections of this application. In some embodiments the cross-links may be used to stabilize the tertiary and/or quarternary structures of the RSV prefusion F protein. In some embodiments, the cross-linking may be intra- and/or intermolecular cross-linking. In some embodiments, the cross-links that are used are targeted cross-links. In some embodiments, the cross-links that are used are stable under physiological conditions. In some embodiments, the cross-links that are used do not lead to aggregate formation of the RSV prefusion F protein, for example during expression and/or during storage (such as storage of compositions comprising high concentrations of the RSV prefusion F protein). In some embodiments the introduction of such cross-links may enhance the effectiveness of the RSV polypeptides, proteins and proteins of the invention as immunogens, such as vaccine immunogens. In some embodiments the introduction of such cross-links may stabilize epitopes (such as the ϕ epitope) within the RSV F protein such that the epitopes can be recognized by particular antibodies, elicit production of antibodies, and/or activate B cell receptors upon antibody binding.

In some embodiments targeted cross-linking can be used. A targeted cross-link is one that can be made to form at a particular position or positions within the RSV F protein or protein complex. Several strategies may be used to target cross-links to specific locations in an RSV F protein or polypeptide, such as the specific locations described herein. The present invention provides residue pairs within the RSV F protein that, when cross-linked, can or may stabilize a RSV F polypeptide, protein, or protein complex in its pre-F conformation, and/or in a conformation that is capable of binding to, or eliciting the production of, neutralizing antibodies, and/or that is capable of generating a neutralizing antibody response in an animal. A targeted cross-link may be introduced at one or more of the locations or positions specified herein by exploiting the physical and/or chemical properties of certain amino acid side chains, for example by making use of enzymatic reactions that recognize specific amino acid sequences or three-dimensional structures, or by incorporating non-natural amino acids that have the ability to form cross-links in a folded protein or protein complex.

Cross-links or modifications may be targeted to specific sites in the structure of the RSV F protein or polypeptide in order to achieve the desired outcome, e.g. stabilization or the pre-F conformation. The present invention contemplates the targeted introduction of one or more cross-links and/or other stabilizing modifications at any suitable position(s) in a RSV F protein or polypeptide, preferably where the cross-link or modification stabilizes the RSV F protein or polypeptide in a pre-fusion conformation, or provides enhanced stabilization of the pre-fusion conformation. The invention contemplates that any RSV F protein amino acid residue, residue pair, secondary structure or other region described herein for di-tyrosine cross-linking may also be used in the formation of other targeted cross-links or bonds or other modifications, including but not limited to amino acid positions Y33, K77, N88, M97, A147, S150, S155, H159, N183, V185, V187, Y198, V220, E222, F223, K226, S255, Y286, K427 and V469, or any combination thereof; residue pairs 147/286, 198/220, 198/222, 198/223, 198/226, 33/496, 77/222, 88/255, 97/159, 183/427, 185/427, and 187/427, or any combination thereof; regions or secondary structures including the F1 mobile N-terminus (residues 137-216), α2 (residues 148-160), α3 (residues 163-173), β3 (residues 176-182), β4 (residues 186-195), α4 (residues 197-211), the F1 mobile C-terminus (residues 461-513), β22 (residues 464-471), α9 (residues 474-479), β23 (residues 486-491), and α10 (493-514); and other regions of RSV F protein including residues from about position 67 to about position 87, from about position 78 to about position 98, from about position 87 to about position 107, from about position 137 to about position 157, from about position 140 to about position 160, from about position 145 to about position 165, from about position 149 to about position 169, from about position 173 to about position 193, from about position 175 to about position 195, from about position 177 to about position 197, from about position 188 to about position 208, from about position 210 to about position 230, from about position 212 to about position 232, from about position 213 to about position 233, from about position 216 to about position 236, from about position 245 to about position 265, from about position 276 to about position 296, from about position 417 to about position 437, and from about position 459 to about position 479.

A wide variety of methods of cross-linking proteins intra- and inter-molecularly are known in the art, including those having cross-links with varying lengths of spacer arms, and those with and without fluorescent and functional groups for purification. Such methods include, but are not limited to, the use of heterobifunctional cross-linkers (e.g. succinimidyl acetylthioacetate (SATA), trans-4-(maleimidylmethyl) cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross-linkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides). Because thiol groups are highly reactive and relatively rare in most proteins by comparison to amine groups, thiol-reactive cross-linking may be used in some embodiments. In cases where thiol groups are missing or not present at appropriate sites in the structures of RSV prefusion F protein, they can be introduced using one of several thiolation methods. For example, Succinimidyl trans-4-(maleimidylmethyl)cyclohexane-1-carboxylate can be used to introduce thiol-reactive groups at amine sites.

Several oxidative cross-links are known, such as disulfide bonds (which form spontaneously and are pH and redox sensitive), and di-tyrosine bonds (which are highly stable, and irreversible under physiological conditions).

In some embodiments the cross-links stabilize the tertiary structure of a RSV pre-fusion F protein. In some embodiments the cross-links stabilize the quaternary structure of a RSV pre-fusion F protein. In some embodiments the cross-links stabilize both the tertiary and quaternary structure of a RSV pre-fusion F protein.

In some embodiments a RSV F protein or polypeptide of the invention has cross-links that are thermostable. In some embodiments a RSV F protein or polypeptide of the invention has cross-links that are not toxic. In some embodiments a RSV F protein or polypeptide of the invention has cross-links that are targeted cross-links, or non-targeted cross-links, or reversible cross-links, or irreversible cross-links, or cross-links formed by use of homo-bifunctional cross-linking agents, or cross-links formed by use of hetero-bifunctional cross-linking agents, or cross-links formed by use of reagents that react with amine groups, or cross-links formed by use of reagents that react with thiol groups, or cross-links formed by use of reagents that are photoreactive, or cross-links formed between amino acid residues, or cross-links formed between mutated amino acid residues incorporated into the structure of the proteins or protein complexes, or oxidative cross-links, or di-tyrosine bonds, or glutaraldehyde cross-links, or any combination thereof. In some embodiments the RSV F protein or polypeptide of the invention does not have glutaraldehyde cross-links.

In some embodiments the RSV F protein or polypeptide of the invention does not have any artificially-introduced disulfide bonds, or if it does have such disulfide bonds, also has additional artificially-introduced cross-links. In some embodiments the RSV F protein or polypeptide of the invention does not have any artificially introduced disulfide bonds, but may have naturally occurring disulfide bonds. Disulfide bonds can be introduced artificially when cysteine side-chains are engineered by point mutation. Disulfide bonds are, however, known to be pH sensitive and to be dissolved under certain redox conditions, and the preventative and/or therapeutic utility of proteins and/or protein complexes engineered with disulfide cross-links, for example to be used as immunogens in vivo, may therefore be compromised. Furthermore, undesired disulfide bonds often form between proteins with free sulfhydryl groups that mediate aggregate formation (see, for example, Harris R J et al. 2004, Commercial manufacturing scale formulation and analytical characterization of therapeutic recombinant antibodies. Drug Dev Res 61 (3): 137-154; Costantino & Pikal (Eds.), 2004. Lyophilization of Biopharmaceuticals, editors Costantino & Pekal. Lyophilization of Biopharmaceuticals. Series: Biotechnology: Pharmaceutical Aspects II, see pages 453-454; Tracy et al., 2002, U.S. Pat. No. 6,465,425), which has also been reported as a problem with HIV gp120 and gp41 (Jeffs et al. 2004. Expression and characterization of recombinant oligomeric envelope glycoproteins derived from primary isolates of HIV-1. Vaccine 22:1032-1046; Schulke et al., 2002. Oligomeric and conformational properties of a proteolytically mature, disulfide-stabilized human immunodeficiency virus type 1 gp140 envelope glycoprotein. J Virol 76:7760-7776). Thus, in many embodiments it is preferred that disulfide bonding is not used, or is not used as the sole method of cross-linking.

If the structure and/or immunogenicity of the RSV prefusion F protein is compromised or altered by a cross-link, maintaining its overall structure and function can be achieved by controlling the availability of amino acid side-chains for the cross-linking reaction or by introducing additional cross-links or other stabilizing modifications. For example, in the case of DT cross-linking, tyrosyl side-chains that are available for reaction, but that lead to the distortion of the structure of the complex, and that compromise the immunogenicity/antigenicity of the RSV F protein, can be removed by mutating such residues to another amino acid such as, for example, phenylalanine. Furthermore, point mutations may be introduced at positions where the amino acid side-chains will react with cross-linking agents or each other, such that the formation of the bond(s) causes the most beneficial outcome. These positions may also be identified as described herein.

When at a selected residue a reactive side-chain is not already present, a point mutation may be introduced, for example using molecular biological methods to introduce such a point mutation into the cDNA of a nucleic acid directing its expression, such that a reactive side-chain is present and available for the reaction.

Cross-links that may be used include, but are not limited to, reversible cross-links resulting from the use of homo- and hetero-bifunctional cross-linking agents that react with amine and/or thiol groups, photoreactive cross-link reagents, any cross-links that may form between non-classical amino acids incorporated into the structure of a protein or protein complex, any oxidative cross-links, such as, but not limited to, di-tyrosine cross-links/bonds, heterobifunctional cross-linkers (e.g. succinimidyl acetylthioacetate (SATA), trans-4-(maleimidylmethyl) cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross-linkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides).

The present invention also contemplates the introduction of targeted non-covalent tyrosine-stacking interactions as "cross-links" to stabilize protein-protein interactions and/or desired protein or peptide conformations, such as the pre-fusion conformation of RSV F protein. The cross-link comprises a targeted pi stacking interaction including but not limited to a T-shaped, sandwich, or parallel displaced pi stacking interaction between the aromatic side chains of an introduced/engineered tyrosine and an endogenous tyrosine, phenylalanine, histidine, or tryptophan within the protein or protein complex, or between the aromatic side chain of an introduced/engineered tyrosine and a second introduced/engineered tyrosine within the protein or protein complex.

Irreversible cross-links, as used in the context of this application, include those that are not significantly dissolved under physiologically relevant conditions. It is preferred that the type of cross-links used should not lead to aggregate formation during expression or when the RSV F polypeptides, proteins and/or protein complexes of the invention are stored at high concentrations. Disulfide bonds are not irreversible cross-links. Rather they are reversible cross-links and may dissolve under physiologically relevant conditions and/or lead to aggregate formation during protein expression and/or production or when stored in high concentrations.

In some embodiments cross-links may be targeted to the specific regions of RSV F polypeptides, proteins and/or protein complexes described herein in order to achieve the desired conformational stabilization and/or the desired immunogenic properties (e.g. the ability to maintain the pre-F conformation and/or to bind to broadly neutralizing antibodies). Alternatively, proteins with the cross-links at the locations specified herein may be isolated from a mixture of cross-linked and un-cross-linked proteins with and without desired modifications, for example based on chemical, physical, and/or functional characteristics. Such characteristics may include, for example, trimerization, the presence of the pre-F conformation, and/or any desired antigenic, immunogenic, or biochemical characteristics.

Alternatively, in some embodiments, cross-links may not be targeted, and proteins with the desired cross-links or properties may be isolated from a mixture of modified and unmodified proteins made using a non-targeted cross-linking system.

In embodiments where RSV F polypeptides, proteins or protein complexes with the desired cross-links are to be isolated from a mixture of cross-linked and un-cross-linked proteins, such isolation or separation may be performed on the basis of one or more characteristics including, but not limited to, molecular weight, molecular volume, chromatographic properties, mobility in electrophoresis, antigenic and biochemical characteristics, fluorescence characteristics, solubility, binding to antibodies, structural characteristics, immunological characteristics, or any other suitable characteristics.

In addition to the specific cross-linking positions described herein, additional positions within RSV F polypeptides, proteins or protein complexes can be identified at which further cross-links can be made, for example where a reactive side-chain would be able to form a bond with a reactive side-chain elsewhere on the RSV F protein/complex. In some embodiments, such additional positions can be selected, for example, to maintain or improve the immunogenicity/antigenicity of the protein, polypeptide or protein complex. In some embodiments, such additional positions to be cross-linked can be selected in pairs.

Di-Tyrosine (DT) Cross-Linking

In some embodiments the present invention provides RSV F polypeptides, proteins and/or protein complexes that comprise di-tyrosine (DT) cross-links, and methods of making such DT-cross-linked RSV F polypeptides, proteins and/or protein complexes.

Di-tyrosine cross-linking introduces one or more covalent carbon-carbon bonds into proteins or protein complexes. This provides a method for stabilizing proteins, protein complexes, and conformations, by introduction of intra- and/or inter-polypeptide di-tyrosine bonds while maintaining their structural and functional integrity (See Marshall et al., U.S. Pat. Nos. 7,037,894 & 7,445,912, the contents of which are hereby incorporated by reference). The minimally altering, and zero-length DT cross-link is not hydrolyzed under physiological conditions, and has been demonstrated to maintain proteins' structural integrity by liquid chromatography/mass spectrometry (LC/MS). Di-tyrosine cross-links are known to be safe, as they form naturally in vivo, both in the context of proteins evolved to utililze their specific characteristics (e.g. Elvin C M et al. 2005, Nature 437:999-1002; Tenovuo J & Paunio K 1979, Arch Oral Biol.; 24(8):591-4), and as a consequence of non-specific protein oxidation (Giulivi et al. 2003, Amino Acids 25(3-4):227-32), and as they are present in large quantities in some of our most common foods: DT bonds form the structure of wheat gluten—the quarternary protein structure comprising the glutenin subunits—e.g. in bread dough during mixing and baking (Tilley et al. 2001, Agric. Food Chem 49, 2627). Di-tyrosine bonds do not form spontaneously in vitro. Rather, the enzymatic cross-link reaction is carried out under optimized conditions to preserve protein structure and function. Therefore, non-specific bonding/aggregation does not occur (unlike with disulfide bonding), and therefore large-scale manufacturing of a DT stabilized immunogen may be economically more feasible.

Tyrosyl side-chains are present in many redox enzymes, and catalysis of the enzyme-specific reactions often involves tyrosyl radicals that are long-lived and have comparatively low reactivity. Under optimized conditions radical formation is specific to tyrosyl side-chains. In close proximity, tyrosyl side chains undergo radical coupling and form a covalent, carbon-carbon bond. Tyrosyl radicals that do not react revert to non-radicalized tyrosyl side-chains (Malencik & Anderson, 2003. Di-tyrosine as a product of oxidative stress and fluorescent probe. Amino Acids 25: 233-247). Therefore, tyrosyl side-chains must be situated in close proximity to form DT bonds, either within a single folded polypeptide chain, or on closely interacting protein domains within a complex. Because a Cα-Cα separation of approximately 5-8 Å is a prerequisite to bond formation (Brown et al., 1998. Determining protein-protein interactions by oxidative cross-linking of a glycine-glycine-histidine fusion protein. Biochemistry 37, 4397-4406; Marshall et al. 2006, U.S. Pat. No. 7,037,894), and because no atom is added in the formation of these bonds, the resulting "staple" is "zero length" and non-disruptive to the protein structure.

Tyrosines residues to be cross-linked may be naturally present in the primary structure of the protein to be cross-linked or may be added by controlled point mutation. To form DT bonds, proteins with tyrosyl side chains can be subjected to reaction conditions that lead to the formation of DT bonds. Such conditions are, or become, oxidative reaction conditions, as the DT bond formation reaction is an oxidative cross-linking reaction. In some embodiments the DT cross-linking reaction conditions yield proteins that are otherwise not, or not detectably, modified. Such conditions may be obtained by use of enzymes that catalyze the formation of $H_2O_2$, such as peroxidases. DT bond formation may be monitored by spectrophotometry with an excitation wavelength of around 320 nm, and fluorescence measured at a wavelength of around 400 nm (see, for example, FIG. 34), while loss of tyrosyl fluorescence is monitored also monitored by standard procedures. When loss of tyrosyl florescence is no longer stoichiometric with DT bond formation, the reaction may be stopped by any methods known to one skilled in the art, such as, for example, by the addition of a reducing agent and subsequent cooling (on ice) or freezing of the sample. Further details of how to peform DT cross-linking are known in the art and are described in, for example, Marshall et al. 2006, U.S. Pat. No. 7,037,894, the contents of which are hereby incorporated by reference.

The major advantages of di-tyrosine cross-linking in protein engineering include (i) the ability to target specific residues for cross-linking (based on the primary, secondary, tertiary, and/or quaternary structures of proteins and complexes), (ii) minimal structural modification, (iii) specificity of the reaction (tyrosine is the only amino acid known to form cross-links under specific cross-linking conditions); (iv) stability of the linkage, (v) zero length of the cross-link (no atom is added), and (vi) the scalability of the cross-linking chemistry.

In some embodiments, targeted DT cross-links may be introduced at one or more of the specific locations in the RSV F protein that are recited herein. In other embodiments, additional positions within RSV F polypeptides, proteins or protein complexes can be identified at which DT cross-links can be made. In some embodiments, di-tyrosine bonds or cross-links are targeted to specific residue pairs within the structure of a RSV F protein or polypeptide where DT bonds will, or are expected to, form due to, for example, their close proximity. In some embodiments tyrosyl side chains are already present at amino acid residues to be cross-linked. In some cases naturally occurring tyrosine residues may constitute either one or both of the paired tyrosine residues necessary for di-tyrosine bond formation. However, in other cases the RSV F polypeptides, proteins and/or protein complexes of the invention are mutated or engineered to add one or more tyrosine residues, or to substitute one or more non-tyrosine residues for tyrosine residues. Such mutations are referred to herein as "to-tyrosine" mutations, and can be introduced at locations where it is desirable to form di-tyrosine cross-links/bonds. In some embodiments, the present invention provides mutant RSV F polypeptides, proteins, and/or protein complexes in which tyrosyl side chains are introduced at desired cross-linking positions by introducing point mutations to tyrosine in a nucleic acid sequence encoding the RSV F polypeptide, protein, or protein complex. Alternatively, in some embodiments RSV proteins, polypeptides or protein complexes, or portions thereof, may be synthesized to include tyrosine residues or amino acids having tyrosyl side chains at desired cross-linking positions. Conversely, in some embodiments the present invention provides mutant RSV F polypeptides, proteins, and/or protein complexes in which tyrosyl side chains are removed at undesirable cross-linking positions by introducing point mutations from tyrosine in a nucleic acid sequence encoding the RSV F polypeptide, protein, or protein complex, or RSV F polypeptides, proteins, or protein complexes may be synthesized to exclude tyrosine residues or amino acids having tyrosyl side chains at positions where cross-linking is not desired. For example, at least one of the tyrosyl side chains can be replaced with another side chain, such as a phenylalanine side chain (see, for example, Marshall C P et al., U.S. patent application Ser. No. 09/837,235, the contents of which are hereby incorporated by reference). Accordingly, the RSV F polypeptides, proteins and protein complexes of the invention may comprise point mutations "to tyrosine" or "from tyrosine." Such mutations can be made by altering the nucleic acid sequences that encode the RSV F polypeptides, proteins and/or protein complexes of the invention using any suitable mutagenesis methods known in the art. Alternatively, mutant RSV F polypeptides, proteins and/or protein complexes may be synthesized, purified, and/or produced by any other suitable methods known in the art.

In some embodiments, the present invention contemplates the targeted introduction of one or more di-tyrosine cross-link at any suitable position(s) in a RSV F polypeptide, protein or protein complex where the cross-link will or may stabilize the RSV F polypeptide, protein or protein complex in its pre-fusion conformation. Such stabilization may be achieved, for example, by introducing cross-links that stabilize interactions between or within RSV F protein F1 and F2 polypeptides and/or by introducing cross-links that stabilize the interactions between or within RSV F protein protomers. In some embodiments, the F1 polypeptide of a RSV F protein is cross-linked with the F2 polypeptide of the same protomer (inter-molecular/intra-protomer bond). In some embodiments, the F1 polypeptide is intra-molecularly cross-linked (e.g., both tyrosines of the cross-link are located within the same F1 polypeptide). In some embodiments, the F2 polypeptide is intra-molecularly cross-linked (e.g., both tyrosines of the cross-link are located within the same F1 polypeptide). In some embodiments, the F1 polypeptide of the RSV prefusion F protein is cross-linked with the F1 polypeptide of an adjacent protomer (inter-protomer bond). In some embodiments, the F1 polypeptide of the RSV prefusion F protein is cross-linked with the F2 polypeptide of an adjacent protomer (inter-protomer bond).

Making and Analyzing RSV F Polypeptides, Proteins, and Protein Complexes

In some embodiments the present invention provides methods for making the RSV F polypeptides, proteins, and protein complexes of the invention. The RSV F polypeptides, proteins, and protein complexes of the invention can be made by any suitable means known in the art. In some embodiments the RSV F polypeptides, proteins, and/or protein complexes of the invention can be made by recombinant means. In some embodiments, the RSV F polypeptides, proteins, and/or protein complexes of the invention, or any portion thereof, can be made by chemical synthesis means. For example, a peptide corresponding to a portion of a protein or protein complex as described herein can be synthesized by use of a peptide synthesizer.

Recombinant Production Methods

In embodiments where the RSV F polypeptides, proteins and protein complexes of the invention are made by recombinant means, nucleic acids encoding the RSV F polypeptides, proteins and protein complexes of the invention can be expressed in any suitable cell type, including, but not limited to mammalian cells and insect cells (such as SF9 or Hi5 cells, using a baculovirus expression system). Methods for expressing polypeptides and proteins from nucleic acid molecules are routine and well known in the art, and any suitable methods, vectors, systems, and cell types known in the art can be used. For example, typically nucleic acid sequences encoding the RSV F polypeptides, proteins and/or protein complexes of the invention will be placed into a suitable expression construct containing a suitable promoter, which will then be delivered to cells for expression.

Chimeric/Fusion Proteins & Oligomerization Domains

In some embodiments it may be desirable to add chimeric domains to the RSV F polypeptides, proteins and/or protein complexes described herein, to produce chimeric proteins/fusion proteins, for example to facilitate the analysis and/or isolation and/or purification of the RSV F polypeptides, proteins and/or protein complexes described herein. In some embodiments, the RSV F polypeptides, proteins and protein complexes of the invention may comprise leader sequences, precursor polypeptide sequences, secretion signals, localization signals, epitope tags, and the like. Epitope tags that can be used include, but are not limited to, FLAG tags, glutathione S-transferase (GST) tags, green fluorescent protein (GFP) tags, hemagglutinin A (HA) tags, histidine (His) tags, luciferase tags, maltose-binding protein (MBP) tags, c-Myc tags, protein A tags, protein G tags, streptavidin (strep) tags, and the like.

In some embodiments it may be desirable to add oligomerization domains to facilitate the assembly of RSV F polypeptides, proteins and/or protein complexes as described herein, and/or to facilitate stabilization of the pre-F conformation, and/or to stabilize other structural features of the RSV F polypeptides, proteins and/or protein complexes. In some embodiments the oligomerization domains are trimerization motifs, including, but not limited to, the T4 foldon motif. There are a wide variety of trimerization domains in natural proteins that can be used for these purposes including, but not limited to, those described in Habazettl et al., 2009 (Habazettl et al., 2009. NMR Structure of a Monomeric Intermediate on the Evolutionarily Optimized Assembly Pathway of a Small Trimerization Domain. J. Mol. Biol. pp. null), Kammerer et al., 2005. (Kammerer et al., 2005. A conserved trimerization motif controls the topology of short coiled coils. Proc Natl Acad Sci USA 102 (39): 13891-13896), Innamorati et al., 2006. (Innamorati et al., 2006. An intracellular role for the C1q-globular domain. Cell signal 18(6): 761-770), and Schelling et al., 2007 (Schelling et al., 2007. The reovirus σ-1 aspartic acid sandwich: A trimerization motif poised for conformational change. Biol Chem 282(15): 11582-11589). Stabilizing trimeric protein complexes can also be accomplished using the GCN4 and T4 fibrinitin motifs (Pancera et al., 2005. Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79(15): 9954-9969; Guthe et al., 2004. Very fast folding and association of a trimerization domain from bacteriophage T4 fibritin. J. Mol. Biol. v337 pp. 905-15; Papanikolopoulou et al., 2008. Creation of hybrid nanorods from sequences of natural trimeric fibrous proteins using the fibritin trimerization motif. Methods Mol Biol 474:15-33). Heterologous oligomerization motifs may be introduced by any recombinant methods known to one of ordinary skill in the art in order to stabilize the protein-protein interactions of the proteins of the present invention.

Chimeric RSV F polypeptides, proteins and/or protein complexes can be made by any method known to one of ordinary skill in the art, and may comprise, for example, one or several RSV F polypeptides, proteins and/or protein complexes of the invention, and/or any fragment, derivative, or analog thereof (for example, consisting of at least a domain of a polypeptide, protein, or protein complex of the invention, or at least 6, and preferably at least 10 amino acids of thereof) joined at its amino- or carboxy-terminus via a peptide bond to an amino acid sequence of another protein or other protein domain or motif. In some embodiments such chimeric proteins can be produced by any method known to one of ordinary skill in the art, including, but not limited to, recombinant expression of a nucleic acid encoding a chimeric protein (e.g. comprising a first coding sequence joined in-frame to a second coding sequence); ligating the appropriate nucleic acid sequences encoding the desired amino acid sequences to each other in the proper coding frame, and expressing the chimeric product.

Post Translational Modifications

In some embodiments, the RSV F polypeptides, proteins and protein complexes described herein may be altered by adding or removing post-translational modifications, by adding or removing chemical modifications or appendices, and/or by introducing any other modifications known to those of ordinary skill in the art. Included within the scope of the invention are RSV F polypeptides, proteins and protein complexes that are modified during or after translation or synthesis, for example, by glycosylation (or deglycosylation), acetylation (or deacetylation), phosphorylation (or dephosphorylation), amidation (or deamidization), pegylation, derivatization by known protecting/blocking groups, proteolytic cleavage, or buy any other means known in the art. For example, in some embodiments the RSV F polypeptides, proteins and/or protein complexes may be subjected to chemical cleavage by cyanogen bromide, trypsin, chymotrypsin, papain, V8 protease, NaBH4, acetylation, formylation, oxidation, reduction, metabolic synthesis in the presence of tunicamycin, etc. In some embodiments such posttranslational modifications can be used to render the RSV F polypeptides, proteins, and/or protein complexes of the present invention more immunogenic, more stable, and/or more capable of binding to, or eliciting the production of, neutralizing and broadly neutralizing antibodies.

Obtaining RSV F in its Pre-F Conformation

In some embodiments the RSV F polypeptides and/or proteins of the invention are assembled into protein complexes having a desired conformational structure, such as the pre-F conformation, and are cross-linked in order to stabilize that conformation. As described elsewhere in the present application, the pre-F conformation of the RSV F protein comprises a trimer formed from three protomers. In some embodiments, prior to and/or during the enzymatic cross-linking reaction, the RSV F protein may be obtained in (and/or maintained in) the pre-F conformation, for example while cross-linking is performed. In some embodiments the RSV F protein may be produced and/or isolated in such a way that most, or substantially all, of the RSV F molecules are present in the pre-F conformation. In some embodiments RSV F molecules in the pre-F conformation may be separated from a mixed population of RSV F protein molecules comprising some that are in the pre-F conformation and some that are in other conformations. In some embodiments, the RSV F protein is expressed in cells (for example as its membrane bound or soluble form) and spontaneously assembles into its normal pre-F conformation. In some embodiments no additional stabilization may be necessary to retain the RSV F protein in its pre-F form. In some embodiments the expressed and assembled/folded RSV F protein may be kept under particular conditions, or in particular compositions, that favor formation and/or maintenance of the pre-F conformation. For example, in some embodiments the RSV prefusion F protein may be maintained in the absence of cells—contact with which might otherwise trigger a switch to the post-F conformation. The RSV prefusion F protein may be obtained and/or isolated and/or maintained in the pre-F conformation using any suitable method known in the art, including, but not limited to, standard protein purification methods, such as ion exchange chromatography, size exclusion chromatography, and/or affinity chromatography methods. In some embodiments the RSV prefusion F protein may be expressed in the presence of, co-expressed with, or contacted with, molecules that bind to the RSV F protein and stabilize it in its pre-F conformation, including, but not limited to, antibodies, small molecules, peptides, and/or peptidomimetics. Non-limiting examples of antibodies that bind to the pre-fusion RSV F protein include the 5C4, AM22, and D25 antibodies (see McLellan et al. (2013) Science 342:592-598, which is hereby incorporated by reference in its entirety). In some embodiments, the RSV F protein may be obtained, isolated, or maintained in its pre-F conformation by controlling the ionic strength of the media/buffer in which the protein is present (such as by using high or low ionic strength media). In some embodiments the RSV F protein may be obtained, isolated, or maintained at one or more temperatures that favor preservation of the pre-F conformation. In some embodiments the RSV F protein may be obtained, isolated, or maintained over a period of time that diminishes the degree to which the pre-F conformation lost.

In some embodiments analysis may be performed to confirm that the desired conformation, such as the pre-F conformation, has been formed and/or maintained in the RSV F protein. Such analysis may be performed prior to cross-linking, during the cross-linking process, after the cross-linking process, or at any combination of such stages. Such analysis may comprise any suitable methods known in the art for assessing the 3-dimensional structure of a protein or protein complex, including functional analysis, crystallographic analysis, and the like. In some embodiments such analysis may include assessing binding of the RSV protein to certain antibodies, such as those that are specific to the pre-F conformation and/or those that are known to bind to the ø site, as described elsewhere herein, including, but not limited to the 5C4, AM22, and D25 antibodies.

Protein Purification

In some embodiments the methods for making RSV F polypeptides, proteins, and protein complexes of the invention may comprise purifying the RSV F polypeptides, proteins, or protein complexes before, during, or after, one or more steps in the manufacturing process. For example, in some embodiments the RSV F polypeptides, proteins, and/or protein complexes of the invention may be purified after completion of all of the manufacturing steps. In some embodiments the RSV F polypeptides, proteins, and/or protein complexes of the invention may be purified before commencing the cross-linking process or after one or more of the intermediate method steps in the process, for example, after expression of an RSV F polypeptide or protein, after assembly of a protein complex, after obtaining the RSV F protein in its pre-F conformation, or during or after performing a cross-linking reaction. The RSV F polypeptides, proteins, and/or protein complexes of the invention may be isolated or purified using any suitable method known in the art. Such methods include, but are not limited to, chromatography (e.g. ion exchange, affinity, and/or sizing column chromatography), ammonium sulfate precipitation, centrifugation, differential solubility, or by any other technique for the purification of proteins known to one of ordinary skill in the art. In specific embodiments it may be necessary to separate the desirable influenza RSV F polypeptides, proteins, and/or protein complexes of the invention from those that were not sufficiently cross-linked, or those in which the pre-F conformation was not sufficiently stabilized. This can be done using any suitable system known in the art. For example, RSV proteins in the pre-F conformation can be separated from those that are not in the pre-F conformation using antibody-based separation methods using pre-F or post-F specific antibodies. The RSV F polypeptides, proteins, and/or protein complexes of the invention may be purified from any source used to produce them. For example, the RSV F polypeptides, proteins, and/or protein complexes of the invention may be purified from sources including insect, prokaryotic, eukaryotic, mono-cellular, multi-cellular, animal, plant, fungus, vertebrate, mammalian, human, porcine, bovine, feline, equine, canine, avian, or tissue culture cells, or any other source. The degree of purity may vary, but in various embodiments, the purified RSV F polypeptides, proteins, and/or protein complexes of the invention are provided in a form in which is they comprise more than about 10%, 20%, 50%, 70%, 75%, 80%, 85%, 90%, 95%, 98%, 99%, or 99.9% of the total protein in the final composition. In some embodiments the RSV F polypeptides, proteins, and/or protein complexes of the invention may be isolated and purified from other proteins, or any other undesirable products (such as non-cross-linked or non-pre-F RSV F), by standard methods including, but not limited to, chromatography, glycerol gradients, affinity chromatography, centrifugation, ion exchange chromatography, size exclusion chromatography, and affinity chromatography, or by any other standard technique for the purification of proteins known in the art. The RSV F polypeptides, proteins, and/or protein complexes to be isolated may be expressed in high or low ionic media, or isolated in high or low ionic buffers or solutions. The RSV F polypeptides, proteins, and/or protein complexes of the invention may also be isolated at one or more temperatures that favor preservation of the desired conformation. They may also be isolated over a period of time that diminishes the degree to which a preparation would have lost the desired conformation. The degree to which a preparation of proteins retains one or more desired conformations (such as the pre-F conformation and/or conformations that favor binding to neutralizing antibodies, or ther desired properties) may be assayed by any suitable method known in the art, including, for example, but not limited to, biochemical, biophysical, immunologic, and virologic analyses. Such assays include, for example, but are not limited to, immunoprecipation, enzyme-linked immunosorbent assays (ELISAs), or enzyme-linked immunosorbent spot (ELISPOT) assays, crystallographic analysis (including co-crystallization with antibodies), sedimentation, analytical ultracentrifugation, dynamic light scattering (DLS), electron microscopy (EM), cryo-EM tomography, calorimetry, surface plasmon resonance (SPR), fluorescence resonance energy transfer (FRET), circular dichroism analysis, and small angle x-ray scattering, neutralization assays, antibody-dependent cellular cytotoxicity assays, and/or virologic challenge studies in vivo.

The yield of the RSV F polypeptides, proteins, and/or protein complexes of the invention can be determined by any means known in the art, for example, by comparing the amount of the final engineered proteins (such as cross-linked pre-F RSV) as compared to the amount of the starting material, or as compared to the amount of the materials present in any preceding step of the production methods. Protein concentrations can determined by standard procedures, such as, for example, Bradford or Lowrie protein assays. The Bradford assay is compatible with reducing agents and denaturing agents (Bradford, M, 1976. Anal. Biochem. 72: 248). The Lowry assay has better compatibility with detergents and the reaction is more linear with respect to protein concentrations and read-out (Lowry, O J, 1951. Biol. Chem. 193: 265).

Exemplary Production Methods

In some embodiments the present invention provides a method for producing a RSV F protein stabilized in its pre-fusion conformation, the method comprising: (a) obtaining an RSV F protein in its pre-F conformation, (b) identifying one or more regions in the tertiary and/or quaternary structure of the RSV prefusion F protein in which the introduction of one or more cross-links could stabilize the pre-F conformation, and (c) introducing into the RSV pre-fusion F protein one or more cross-links at one or more of the regions identified in step (b) to form an engineered RSV F protein locked in its pre-fusion conformation. In some embodiments, the regions identified in step (b) comprise one or more of the specific regions or specific amino acid residues described herein. In some embodiments the cross-links are targeted cross-links. In some embodiments the cross-links are targeted DT cross-links. In some embodiments the cross-links are stable under physiological conditions. In some embodiments, the engineered RSV F protein stabilized in its pre-fusion conformation is useful as a vaccine immunogen. In some embodiments, the engineered RSV F protein locked in its pre-fusion conformation has one or more of the following properties: (i) enhanced ability bind to a neutralizing antibody as compared to the RSV F protein not so engineered (i.e. as compared to the RSV F protein without or before introduction of the cross-links), (ii) enhanced ability bind to a broadly neutralizing antibody as compared to the RSV F protein not so engineered, (iii) enhanced ability bind to and activate B cell receptors as compared to the RSV F protein not so engineered, (iv) enhanced ability to elicit an antibody response in an animal as compared to the RSV F protein not so engineered, (v) enhanced ability to elicit a protective antibody response in an animal as compared to the RSV F protein not so engineered, (vi) enhanced ability to elicit production of neutralizing antibodies in an animal as compared to the RSV F protein not so engineered, (vii) enhanced ability to elicit production of broadly neutralizing antibodies in an animal as compared to the RSV F protein not so engineered, (viii) enhanced ability to elicit a protective immune response in an animal as compared to the RSV F protein not so engineered, and (ix) enhanced ability to bind to and elicit production of antibodies that recognize quaternary neutralizing epitopes in an animal as compared to the RSV F protein not so engineered. In some embodiments the methods for producing an RSV F protein stabilized in its pre-fusion conformation described herein also comprise performing an assay to determine if the engineered RSV F protein stabilized in its pre-fusion conformation and/or has one or more of the properties listed above.

Properties of RSV F Polypeptides, Proteins and/or Protein Complexes

In some embodiments, the RSV F polypeptides, proteins and/or protein complexes of the invention, including in particular those that are cross-linked as described herein, have certain structural, physical, functional, and/or biological properties. Such properties may include one or more of the following, or any combination of the following: existence of the pre-F conformation, stability of the RSV pre-F conformation; Improved stability of the RSV pre-F conformation (as compared to non-cross-linked RSV F proteins); Improved half-life of the RSV pre-F conformation (as compared to non-cross-linked RSV F proteins); Improved thermostability (as compared to non-cross-linked RSV F proteins); Prolonged shelf-life (as compared to non-cross-linked RSV F proteins); Prolonged half-life inside the body of a subject (as compared to non-cross-linked RSV F proteins); Ability to be stored in solution without forming aggregates (including when present at a high concentration in solution); Reduced aggregation in solution (as compared to non-cross-linked RSV F proteins); Binding to an antibody; Binding to a neutralizing antibody; Binding to a broadly neutralizing antibody; Binding to a pre-F-specific antibody; Binding to an antibody that recognizes site ø; Binding to a conformationally-specific antibody; Binding to an antibody that recognizes a metastable epitope; Binding to an antibody selected from the group consisting of D25, AM22 and 5C4 (which antibodies are described in McLellan et al., 2013, Science, 340, p. 1113; Kwakkenbos et al., 2010, Nature Medicine, 16, p. 123; Spits & Beaumont, U.S. patent application Ser. No. 12/600,950; Beaumont, Bakker & Yasuda, U.S. patent application Ser. No. 12/898,325, the contents of each of which are hereby incorporated by reference in their entireties); Binding to palivizumab (Synagis); Binding to the neutralizing antibody 101F; Binding to a B cell receptor; Activation of a B Cell receptor; Eliciting an antibody response in an animal; Eliciting a protective antibody response in an animal; Eliciting production of neutralizing antibodies in an animal; Eliciting production of broadly neutralizing antibodies in an animal; Eliciting production of antibodies that recognize quaternary neutralizing epitopes (QNEs) in an animal; Eliciting a protective immune response in an animal; and/or Eliciting a humoral immune response in an animal. In the case of binding to antibody molecules, in some embodiments the RSV F polypeptides, proteins, and/or protein complexes of the invention bind to the antibodies (such as pre-F-specific antibodies, antibodies that bind to site ø, and/or D25, AM22 or 5C4) with high specificity and/or with high affinity.

Assays for Properties

In some embodiments the RSV F polypeptides, proteins, and/or protein complexes of the invention, or any intermediates in their manufacture, may be analyzed to confirm that they have desired properties, such as the desired structural, physical, functional, and/or biological properties—such as those properties listed above or identified elsewhere in this patent specification. For example, in some embodiments in vitro or in vivo assays can be performed to assess the RSV F protein's conformational structure, stability (e.g. thermostability), half-life (e.g. inside the body of a subject), aggregation in solution, binding to an antibody (such as a neutralizing antibody, broadly neutralizing antibody; pre-F-specific antibody; antibody that recognizes site ø, conformationally-specific antibody, antibody that recognizes a metastable epitope, D25, AM22, 5C4, 101F or palivizumab), binding to a B cell receptor, activation of a B Cell receptor, antigenicity, immunogenicity, ability to elicit an antibody response, ability to elicit a protective antibody/immune response, ability to elicit production of neutralizing antibodies, or ability to elicit a production of broadly neutralizing antibodies. In embodiments where the RSV F polypeptides, proteins, and/or protein complexes of the invention are tested in an animal in vivo, the animal may be any suitable animal species, including, but not limited to a mammal (such as a rodent species (e.g. a mouse or rat), a rabbit, a ferret, a porcine species, a bovine species, an equine species, an ovine species, or a primate species (e.g. a human or a non-human primate), or an avian species (such as a chicken).

Assays for assessing a protein's conformational structure are well known in the art and any suitable assay can be used, including, but not limited to, crystallographic analysis (e.g. X-ray crystallography or electron crystallography), sedimentation analysis, analytical ultracentrifugation, electron microscopy (EM), cryo-electron microscopy (cryo-EM), cryo-EM tomography, nuclear magnetic resonance (NMR), small angle x-ray scattering, fluorescence resonance energy transfer (FRET) assays, and the like.

Assays for assessing a protein's stability are well known in the art and any suitable assay can be used, including, but not limited to, denaturing and non-denaturing electrophoresis, isothermal titration calorimetry, and time-course experiments in which proteins are incubated and analyzed over time at varying protein concentrations, temperatures, pHs or redox conditions. Proteins may also be analyzed for susceptibility to proteolytic degradation.

Assays for assessing binding of proteins to antibodies are well known in the art, and any suitable assay can be used, including, but not limited to, immunoprecipitation assays, enzyme-linked immunosorbent assays (ELISAs), enzyme-linked immunosorbent spot assays (ELISPOTs), crystallographic assays (including co-crystallization with antibodies), surface plasmon resonance (SPR) assays, fluorescence resonance energy transfer (FRET) assays, and the like.

Assays for assessing neutralization activity are well known in the art, and any suitable assay can be used. For example, assays can be performed to determine the neutralizing activity of antibodies or antisera generated by vaccination/immunization of animals with the RSV F polypeptides, proteins, and/or protein complexes of the invention. Neutralization assays known in the art include, but are not limited to, those described by Dey et al. 2007 (Dey et al., 2007, Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593) and Beddows et al., 2006 (Beddows et al., 2007, A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360: 329-340).

Assays for assessing whether a vaccine immunogen is capable of eliciting an immune response and/or proving protective immunity are well known in the art, and any suitable assay can be used. For example, assays can be performed to determine whether vaccination/immunization of animals with the RSV F polypeptides, proteins, and/or protein complexes of the invention provide an immune response and/or protective immunity against infection with RSV. In some embodiments comparisons may be made between placebo and test vaccinated groups with regard to their rates of infection or sero-conversion or viral loads.

Assays for assessing a protein's pharmacokinetics and bio-distribution are also well known in the art, and any suitable assay can be used to assess these properties of the RSV F polypeptides, proteins, and/or protein complexes of the invention.

Compositions

In some embodiments the present invention provides compositions comprising any of the RSV F polypeptides, proteins, and/or protein complexes described herein. In some embodiments such compositions may be immunogenic compositions, vaccine compositions and/or therapeutic compositions. In some embodiments, such compositions may be administered to subjects.

In some embodiments the RSV F polypeptides, proteins, and/or protein complexes of the invention may be provided in a composition that comprises one or more additional active components, such as one or more additional vaccine immunogens or therapeutic agents. In some embodiments the RSV F polypeptides, proteins, and/or protein complexes of the invention may be provided in a composition that comprises one or more other components, including, but not limited to, pharmaceutically acceptable carriers, adjuvants, wetting or emulsifying agents, pH buffering agents, preservatives, and/or any other components suitable for the intended use of the compositions. Such compositions can take the form of solutions, suspensions, emulsions and the like. The term "pharmaceutically acceptable carrier" includes various diluents, excipients and/or vehicles in which, or with which, the RSV F polypeptides, proteins, and/or protein complexes of the invention can be provided. The term "pharmaceutically acceptable carrier" includes, but is not limited to, carriers known to be safe for delivery to human and/or other animal subjects, and/or approved by a regulatory agency of the Federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil), and the like. In some embodiments the compositions of the invention also comprise one or more adjuvants. Exemplary adjuvants include, but are not limited to, inorganic or organic adjuvants, oil-based adjuvants, virosomes, liposomes, lipopolysaccharide (LPS), molecular cages for antigens (such as immune-stimulating complexes ("ISCOMS")), Ag-modified saponin/cholesterol micelles that form stable cage-like structures that are transported to the draining lymph nodes), components of bacterial cell walls, endocytosed nucleic acids (such as double-stranded RNA (dsRNA), single-stranded DNA (ssDNA), and unmethylated CpG dinucleotide-containing DNA), AUM, aluminum phosphate, aluminum hydroxide, and Squalene. In some embodiments virosomes are used as the adjuvant. Additional commercially available adjuvants that can be used in accordance with the present invention include, but are not limited to, the Ribi Adjuvant System (RAS, an oil-in-water emulsion containing detoxified endotoxin (MPL) and mycobacterial cell wall components in 2% squalene (Sigma M6536)), TiterMax (a stable, metabolizable water-in-oil adjuvant (CytRx Corporation 150 Technology Parkway Technology Park/Atlanta Norcross, Ga. 30092)), Syntex Adjuvant Formulation (SAF, an oil-in-water emulsion stabilized by Tween 80 and pluronic polyoxyethlene/polyoxypropylene block copolymer L121 (Chiron Corporation, Emeryville, Calif.)), Freund's Complete Adjuvant, Freund's Incomplete Adjuvant, ALUM—aluminum hydroxide, Al(OH)3 (available as Alhydrogel, Accurate Chemical & Scientific Co, Westbury, N.Y.), SuperCarrier (Syntex Research 3401 Hillview Ave. P.O. Box 10850 Palo Alto, Calif. 94303), Elvax 40W1,2 (an ethylene-vinyl acetate copolymer (DuPont Chemical Co. Wilmington, Del.)), L-tyrosine co-precipitated with the antigen (available from numerous chemical companies); Montanide (a manide-oleate, ISA Seppic Fairfield, N.J.)), AdjuPrime (a carbohydrate polymer), Nitrocellulose-absorbed protein, Gerbu adjuvant (C-C Biotech, Poway, Calif.), and the like.

In some embodiments the compositions of the invention comprise an "effective amount" of a RSV F polypeptide, protein, and/or protein complex of the invention. An "effective amount" is an amount required to achieve a desired end result. Examples of desired end results include, but are not limited to, the generation of a humoral immune response, the generation of a neutralizing antibody response, the generation of a broadly neutralizing antibody response, and the generation of protective immunity. The amount of a RSV F polypeptide, protein, and/or protein complex of the invention that is effective to achieve the desired end result will depend on variety of factors including, but not limited to, the type, subtype, and strain of the RSV virus against which protection or some other therapeutic effect is sought, the species of the intended subject (e.g. whether a human or some other animal species), the age and/or sex of the intended subject, the planned route of administration, the planned dosing regimen, the seriousness of any ongoing influenza infection (e.g. in the case of therapeutic uses), and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

Uses of the RSV F Polypeptides, Proteins & Protein Complexes of the Invention

In some embodiments, the RSV F polypeptides, proteins, and protein complexes of the invention may be useful as research tools, as diagnostic tools, as therapeutic agents, as targets for the production of antibody reagents or therapeutic antibodies, and/or as vaccines or components of vaccine compositions. For example, in some embodiments the RSV F polypeptides, proteins, and protein complexes of the invention are useful as a vaccine immunogens in animal subjects, such as mammalian subject, including humans. These and other uses of the RSV F polypeptides, proteins, and protein complexes of the invention are described more fully below. Those of skill in the art will appreciate that the RSV F polypeptides, proteins, and protein complexes of the invention may be useful for a variety of other applications also, and all such applications and uses are intended to fall within the scope of this invention.

Tools for Studying RSV F Antibodies

In one embodiment, the RSV F polypeptides, proteins, and protein complexes of the invention may be useful as analytes for assaying and/or measuring binding of, and/or titers of, anti-RSV F antibodies, for example in ELISA assays, Biacore/SPR binding assays, and/or any other assays for antibody binding known in the art. For example, the RSV F polypeptides, proteins, and protein complexes of the invention could be used to analyze, and/or compare the efficacy of anti-RSV F antibodies.

Tools for Generation of Antibodies

The RSV F polypeptides, proteins, and protein complexes of the invention may also be useful for the generation of therapeutic antibodies and/or antibodies that can be used as research tools or for any other desired use. For example, the RSV F polypeptides, proteins, and protein complexes of the invention can be used for immunizations to obtain antibodies to the RSV F protein for use as research tools and/or as therapeutics. In some embodiments the RSV F polypeptides, proteins, and protein complexes of the invention can be used to immunize a non-human animal, such as a vertebrate, including, but not limited to, a mouse, rat, guinea pig, rabbit, goat, non-human primate, etc. in order to generate antibodies. Such antibodies, which may be monoclonal or polyclonal, and/or cells that produce such antibodies, can then be obtained from the animal. For example, in some embodiments RSV F polypeptides, proteins, and protein complexes of the invention may be used to immunize a mouse and to produce and obtain monoclonal antibodies, and/or hybridomas that produce such monoclonal antibodies. Such methods can be carried out using standard methods known in the art for the production of mouse monoclonal antibodies, including standard methods for hybridoma production. In some embodiments RSV F polypeptides, proteins, and protein complexes of the invention may be used for the production of a chimeric (e.g. part-human), humanized, or fully-human antibody, for example using any of the methods currently known in the art for production of chimeric, humanized and fully human antibodies, including, but not limited to, CDR grafting methods, phage-display methods, transgenic mouse methods (e.g. using a mouse that has been genetically altered to allow for the production of fully human antibodies, such as the Xenomouse) and/or any other suitable method known in the art. Antibodies to the RSV F polypeptides, proteins, and protein complexes of the invention made using such systems can be characterized antigenically using one or a set of several antigens, preferably including the RSV F polypeptides, proteins, and protein complexes of the invention themselves. Additional characterization of such antibodies may be carried out by any standard methods known to one of ordinary skill in the art, including, but not limited to, ELISA-based methods, SPR-based methods, biochemical methods (such as, but not limited to, iso-electric point determination), and methods known in the art for studying biodistribution, safety, and efficacy of antibodies—for example in preclinical and clinical studies.

Administration to Subjects

In some embodiments, the present invention provides methods that comprise administering the RSV F polypeptides, proteins and/or protein complexes of the invention (or compositions comprising such RSV F polypeptides, proteins and/or protein complexes) to subjects. Such methods may comprise methods for treating individuals having RSV (i.e. therapeutic methods) and/or methods for protecting individuals against future RSV infection (i.e. prophylactic methods).

Subjects to which the RSV F polypeptides, proteins and/or protein complexes of the invention, or compositions comprising such RSV F polypeptides, proteins and/or protein complexes, can be administered (for example in the course of a method of treatment or a method of vaccination) include any and all animal species, including, in particular, those that are susceptible to RSV infection or that can provide model animal systems for the study of RSV infection. In some embodiments, the subjects are mammalian species. In some embodiments, the subjects are avian species. Mammalian subjects include, but are not limited to, humans, non-human primates, rodents, rabbits, and ferrets. Avian subjects include, but are not limited to chickens, such as those on poultry farms. In some embodiments the subjects to which the RSV F polypeptides, proteins and/or protein complexes of the invention, or compositions comprising such RSV F polypeptides, proteins and/or protein complexes are administered, either have RSV, or are at risk of RSV infection. In some embodiments, the subjects are immunocompromised. In some embodiments, the subjects have a heart disease or disorder. In some embodiments, the subject is a human of greater than about 50 years in age, greater than about 55 years in age, greater than about 60 years in age, greater than about 65 years in age, greater than about 70 years in age, greater than about 75 years in age, greater than about 80 years in age, greater than about 85 years in age, or greater than about 90 years in age. In some embodiments, the subject is a human of less than about 1 month in age, less than about 2 months in age, less than about 3 months in age, less than about 4 months in age, less than about 5 months in age, less than about 6 months in age, less than about 7 months in age, less than about 8 months in age, less than about 9 months in age, less than about 10 months in age, less than about 11 months in age, less than about 12 months in age, less than about 13 months in age, less than about 14 months in age, less than about 15 months in age, less than about 16 months in age, less than about 17 months in age, less than about 18 months in age, less than about 19 months in age, less than about 20 months in age, less than about 21 months in age, less than about 22 months in age, less than about 23 months in age, or less than about 24 months in age.

Various delivery systems are known in the art and any suitable delivery systems can be used to administer the compositions of the present invention to subjects. Such delivery systems include, but are not limited to, intradermal, intramuscular, intraperitoneal, intravenous, subcutaneous, intranasal, epidural, and oral delivery systems. The compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In some embodiments it may be desirable to administer the pharmaceutical compositions of the invention locally to a tissue in which the RSV F protein or polypeptide may be most effective in generating a desirable outcome. This may be achieved by, for example, local infusion, injection, delivery using a catheter, or by means of an implant, such as a porous, non-porous, or gelatinous implant or an implant comprising one or more membranes (such as sialastic membranes) or fibers from or through which the protein or protein complexes may be released locally. In some embodiments a controlled release system may be used. In some embodiments a pump may be used (see Langer, supra; Sefton, 1987. CRC Crit. Ref. Biomed. Eng. 14: 201; Buchwald et al., 1980. Surgery 88: 507; Saudek et al., 1989. N. Engl. J. Med. 321: 574). In some embodiments polymeric materials may be used to facilitate and/or control release of the RSV prefusion F protein of the invention (see Medical Applications of Controlled Release, Langer and Wise (eds.), 1974. CRC Pres., Boca Raton, Fla.; Controlled Drug Bioavailability, 1984. Drug Product Design and Performance, Smolen and Ball (eds.), Wiley, New York; Ranger & Peppas, 1983 Macromol. Sci. Rev. Macromol. Chem. 23: 61; see also Levy et al., 1985. Science 228:190; During et al, 1989. Ann. Neurol. 25: 351; Howard et al., 1989. J. Neurosurg 71:105). In some embodiments a controlled release system can be placed in proximity to the tissue/organ to which the RSV prefusion F protein or polypeptide is to be delivered (see, e.g., Goodson, 1984. Medical Applications of Controlled Release, supra, vol. 2: 115-138). Some suitable controlled release systems that may be used in conjunction with the present invention are described Langer, 1990, Science; vol. 249: pp. 527-1533.

In some embodiments, administration of the compositions of the invention can be performed in conjunction with administration of one or more immunostimulatory agents. Non-limiting examples of such immunostimulatory agents include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory agents, such as macrophage inflammatory factor, Flt3 ligand, B7.1; B7.2. The immunostimulatory agents can be administered in the same formulation as the RSV F protein or polypeptide, or can be administered separately.

In some embodiments, the RSV F polypeptides, proteins, and/or protein complexes of the invention, or compositions comprising them, can be administered to subjects in a variety of different RSV vaccination methods or regimens. In some such embodiments, administration of a single dose is preferred. However, in other embodiments, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against RSV infection. Similarly, adults who are particularly susceptible to RSV infection, such as, for example, the elderly and immunocompromised individuals, may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

In some embodiments, dosing regimens may comprise a single administration/immunization. In other embodiments, dosing regimens may comprise multiple administrations/immunizations. For example, vaccines may be given as a primary immunization followed by one or more boosters. In some embodiments of the present invention such a "prime-boost" vaccination regimen may be used. For example, in some such prime-boost regimens a composition comprising a RSV F polypeptide, protein or protein complex as described herein may be administered to an individual on multiple occasions (such as two, three, or even more occasions) separated in time, with the first administration being the "priming" administration and subsequent administrations being "booster" administrations. In other such prime-boost regimens a composition comprising a RSV F polypeptide, protein or protein complex as described herein may be administered to an individual after first administering to the individual a composition comprising a viral or DNA vector encoding an RSV polypeptide, protein or protein complex as a "priming" administration, with one or more subsequent "booster" administrations of a composition comprising a RSV F polypeptide, protein or protein complex as described herein. Boosters may be delivered via the same and/or different route as the primary immunization. Boosters are generally administered after a time period after the primary immunization or the previously administered booster. For example, a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

Preferred unit dosage formulations are those containing a dose or unit (e.g. an effective amount), or an appropriate fraction thereof, of the RSV F polypeptides, proteins, and/or protein complexes of the invention. In addition to such ingredients, formulations of the present invention may include other agents commonly used by one of ordinary skill in the art. Pharmaceutical compositions provided by the invention may be conveniently presented in preferred unit dosage formulations prepared using conventional pharmaceutical techniques. Such techniques include the step of bringing into association the active ingredient and the pharmaceutical carrier(s) or excipient(s) or other ingredients. In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Kits

The present invention further provides kits comprising RSV polypeptides, proteins or protein complexes of the invention, or compositions containing such polypeptides, proteins or protein complexes. To facilitate use of the methods and compositions of the invention, any of the components and/or compositions described herein, and additional components useful for experimental or therapeutic or vaccine purposes, can be packaged in the form of a kit. Typically, the kit contains, in addition to the above components, additional materials which can include, e.g., instructions for using the components, packaging material, a container, and/or a delivery device.

Various embodiments of the present invention may also be further described by the following non-limiting examples:

Example

RSV F protein variants E222Y (SEQ ID NO:13), K226Y (SEQ ID NO:15), V469Y (SEQ ID NO:16), N88Y/S255Y (SEQ ID NO:18), V185Y/K427Y (SEQ ID NO:20) were expressed in human cells as modified by the introduction of di-tyrosine bonds as described below.

Figure 33:
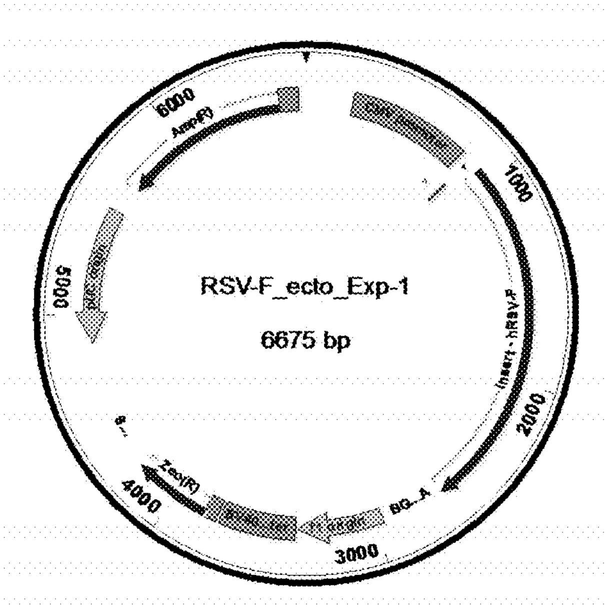
FIG. 33. Illustrative nucleic acid construct for expression of RSV F protein in mammalian cells.

Expression Plasmids. cDNA encoding a C-terminal fusion of the WT human RSV-F ectodomain or DS-Cav1 protein ectodomain to the T4 fibritin foldon trimerization motif, thrombin cleavage-site, 6×HIS-tag (SEQ ID NO: 46), and strep-tag were codon-optimized for human expression and synthesized (Geneart). cDNA encoding RSV F protein variants E222Y (SEQ ID NO:13), K226Y (SEQ ID NO:15), V469Y (SEQ ID NO:16), N88Y/S255Y (SEQ ID NO:18), V185Y/K427Y (SEQ ID NO:20) were also synthesized. These DNA sequences were cloned into the pCDNA3.1/zeo+ expression vector (Invitrogen) via 5' BamHI and 3'XhoI restriction endonuclease sites using standard methods (FIG. 33).

Cells and Transfections. HEK 293 cells (ATCC) were grown in Dulbecco's Modification of Eagle's Medium (DMEM, Invitrogen) supplemented with 10% Fetal Bovine Serum and 50 μg/ml gentamycin. Cells were seeded into 6-well tissue culture plates (Corning) and grown till 80% confluent (~24 h). Cells were transfected with 2 μg of each RSV-F expression plasmid per well using a 1:4 ratio (MN) of DNA to polyethylenimine (25 kDa, linear). 16 h post-transfection, media was removed and replaced with 2 ml/well of serum-free Freestyle-293 expression media (Invitrogen). Cells were cultured at 37 degrees C. for an additional 48 h-72 h in 5% $CO_2$ prior to collection and analysis.

Figures 35A, 35B:
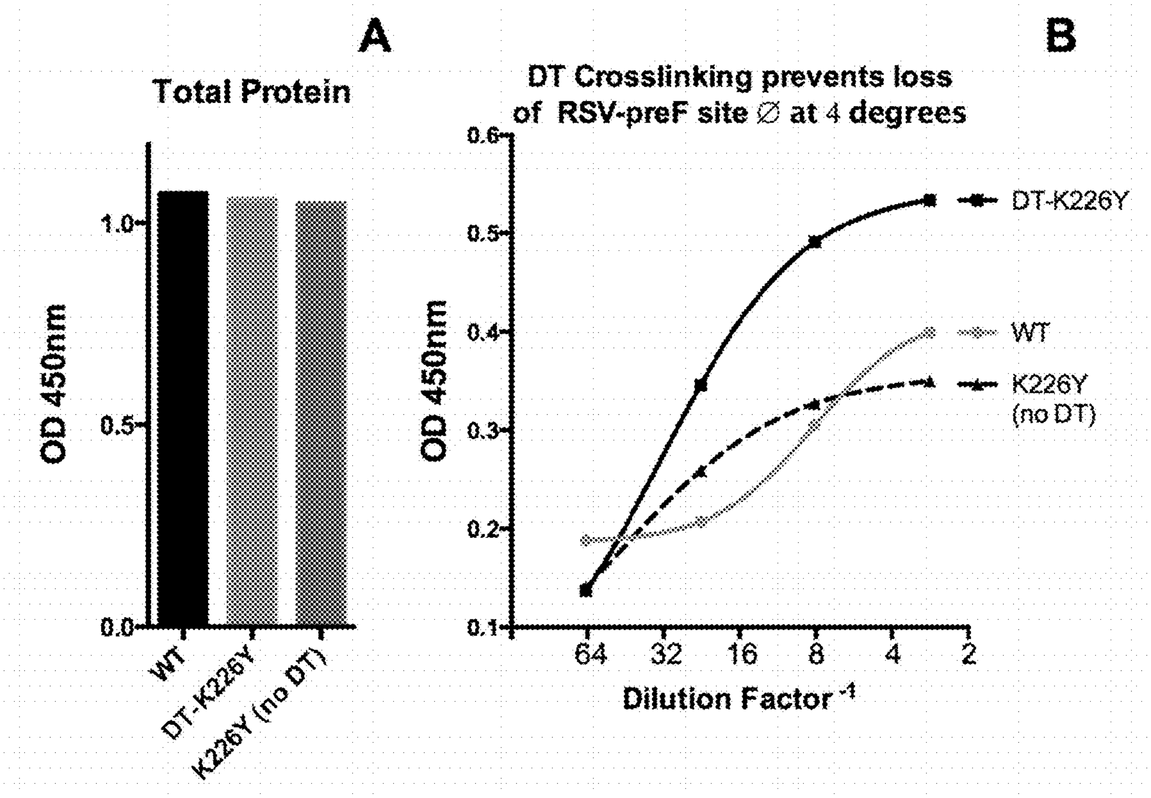
FIGS. 35A-35B. Di-tyrosine cross-linking stabilizes key epitope on RSV prefusion F protein. HEK 293 cells were transfected with constructs expressing the wild-type (WT) RSV-F or a variant containing the K226Y substitution. (A) 72 h post transfection, supernatents were cross-linked (DT) or left uncross-linked and total protein was measured by ELISA using a high-affinity human anti-hRSV antibody (100 ng/ml in PBS) that recognizes both pre- and post-fusion forms of RSV-F. (B) Following storage at 4 degrees C. for 16 days presentation of site ø was measured by ELISA using a preF specific human monoclonal antibody (2 μg/ml in PBS) that recognizes site ø.

Detection of RSV-F in Cell Supernatants by ELISA. After collection, total RSV-F protein was directly captured from cell supernatants for 1 h at room temperature in EIA/RIA high-bind 96-well plates (Corning). Protein-containing and control wells were subsequently blocked with 4% nonfat milk in PBS-tween20 (0.05%) for 1 h at room temperature. Plates were washed 3× with PBS-T (400 μl/well). Total RSV-F was detected for 1 h using a high-affinity human anti-hRSV antibody (100 ng/ml in PBS) that recognizes both pre- and post-fusion forms of RSV-F. Prefusion F was detected using a pre-F specific human monoclonal antibody (2 μg/ml in PBS) that recognizes site ø. Wells were again washed 3× in PBS-T followed by a 1 h room temperature incubation with an HRP-conjugated goat anti-human $F(ab)_2$ (Jackson Immunoresearch) at a 1:5000 dilution in PBS. Wells were washed 6× with PBS-T and total RSV-F was detected and quantified using 100 μl 3,3',5,5'-tetramethylbenzidine (TMB) to produce a colorimetric signal. The colorimetric reaction was stopped by the addition of equal volume 4N sulfuric acid. Final Optical Density readings were taking at 450 nm using a BioRad Benchmark Plus microplate absorbance spectrophotometer. A 2× serial dilution series for each supernatant was used to determine the linear range of detectable signal for each sample allowing accurate comparison of the relative amount of RSV-F between samples (FIG. 35).

Figure 34:
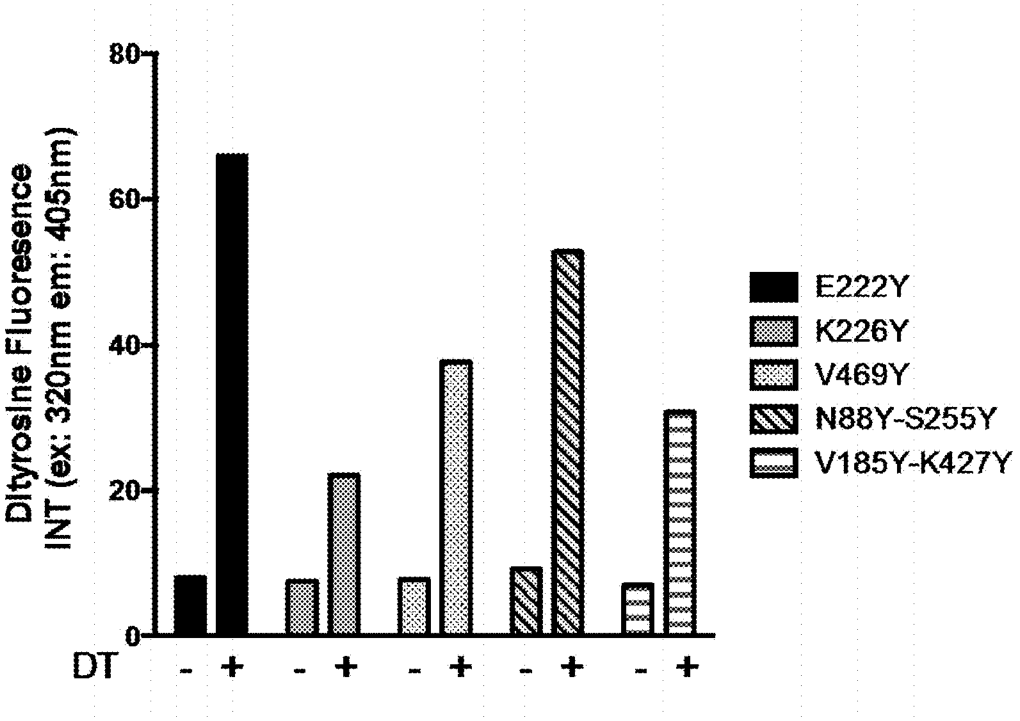
FIG. 34. Targeted di-tyrosine cross-linking of RSV F protein. HEK 293 cells were transfected with vectors expressing RSV-F variants that enabling $F_1$-$F_1$ intra-protomer DT-cross-links (E222Y (SEQ ID NO: 13) and K226Y (SEQ ID NO:15)), $F_1$-$F_2$ intra-protomer DT-cross-links (V469Y (SEQ ID NO:16) and N88Y-S255Y (SEQ ID NO:18)), or $F_1$-$F_1$ intermolecular DT-cross-links (V185Y-K427Y (SEQ ID NO:20)). Background-subtracted fluorescence intensity values are shown. (INT) intensity, (DT) di-tyrosine, (−) and (+) indicate before and after application of the di-tyrosine cross-linking technology, respectively.

Di-tyrosine-Cross-linking in Cell Supernatants. Immediately following collection, 100 μl of transfected and control cell supernatants were transferred to wells of black, flat-bottom, non-binding 96-well FIA plates (Greiner bio-one). 300 ng of *Arthromyces ramosus* peroxidase was added to each sample to be cross-linked. 1 μl of 1.2 mM $H_2O_2$ was then added to both control and DT reactions for a final reaction concentration of 120 μM $H_2O_2$. Reactions were allowed to proceed for 20 minutes at room temperature followed by alkalization of the reactions by addition of equal volume sodium phosphate buffer at pH 10. Di-tyrosine specific fluorescence was read at an excitation wavelength of 320 nm and emission wavelength of 405 nm using a Thermo Scientific Fluoroskan Ascent FL (FIG. 34).

72 h post transfection, supernatents were cross-linked (DT) or left uncross-linked and total protein was measured by ELISA using a high-affinity human anti-hRSV antibody (100 ng/ml in PBS) that recognizes both pre- and post-fusion forms of RSV-F. See FIG. 35A. Following storage at 4 degrees C. for 16 days presentation of site ø was measured by ELISA using a preF specific human monoclonal antibody (2 μg/ml in PBS) that recognizes site ø. Di-tyrosine cross-links were found to stabilize key epitope on RSV prefusion F protein. See FIG. 35B.

While the foregoing invention has been described in some detail for purposes of clarity and understanding, it will be clear to one skilled in the art from a reading of this disclosure that various changes in form and detail can be made without departing from the true scope of the invention. The invention may also be further defined in terms of the following claims.

The invention claimed is:

1. A RSV F polypeptide, protein or protein complex comprising a point mutation to tyrosine at amino acid position 226, or an acid position equivalent to position 226 as determined by alignment to, and/or using the amino acid numbering of, SEQ ID NO.1.

2. A RSV F polypeptide, protein or protein complex according to claim 1, wherein the polypeptide, protein or protein complex is stabilized in a prefusion conformation by one or more di-tyrosine cross-links.

3. A RSV F polypeptide, protein or protein complex according to claim 2, wherein the polypeptide, protein or protein complex polypeptide comprises a di-tyrosine cross-link between the tyrosine at amino acid position 226 and a tyrosine at amino acid position 198, or an amino acid position equivalent to position 198 as determined by alignment to, and/or using the amino acid numbering of, SEQ ID NO.1.

4. A RSV F polypeptide, protein or protein complex according to claim 1, wherein the RSV F polypeptide, protein or protein complex is derived from RSV type A or RSV type B.

5. A RSV F polypeptide, protein or protein complex according to claim 2, wherein the RSV F polypeptide, protein or protein complex is capable of binding to an antibody that recognizes antigenic site 0.

6. A RSV F polypeptide, protein or protein complex comprising amino acid residues 1-513 of either SEQ ID NO. 15, SEQ ID NO. 27, SEQ ID NO. 28, or SEQ ID NO. 32.

7. A RSV F polypeptide, protein or protein complex according to claim 1, comprising SEQ ID NO. 15, SEQ ID NO. 27, SEQ ID NO. 28, or SEQ ID NO. 32.

8. A RSV F polypeptide, protein or protein complex according to claim 2, wherein the polypeptide, protein or protein complex further comprises one or more additional artificially introduced cross-links.

9. A RSV F polypeptide, protein or protein complex according to claim 8, wherein the additional artificially introduced cross links are di-sulfide bonds.

10. A RSV F polypeptide, protein or protein complex according to claim 1, wherein the polypeptide, protein or protein complex further comprises one or more point mutations to cysteine.

11. A RSV F polypeptide, protein or protein complex according to claim 1, wherein the polypeptide, protein or protein complex further comprises one or more cavity-filling hydrophobic amino acid substitutions.

12. A RSV F polypeptide, protein or protein complex according to claim 1, wherein the polypeptide, protein or protein complex further comprises a trimerization domain.

13. A RSV F polypeptide, protein or protein complex according to claim 12, wherein the trimerization domain is a foldon domain.

14. A nucleic acid molecule encoding a RSV F polypeptide, protein or protein complex according to claim 1.

15. A composition comprising a RSV F polypeptide, protein or protein complex according to claim 1.

* * * * *

UNITED STATES PATENT AND TRADEMARK OFFICE

CERTIFICATE OF CORRECTION

PATENT NO. : 10,125,172 B2
APPLICATION NO. : 14/340519
DATED : November 13, 2018
INVENTOR(S) : Marshall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 191 days.

Signed and Sealed this
Eighteenth Day of June, 2019

Andrei Iancu
*Director of the United States Patent and Trademark Office*

SEQUENCE LISTING

```
<160> NUMBER OF SEQ ID NOS: 47

<210> SEQ ID NO 1
<211> LENGTH: 568
<212> TYPE: PRT
<213> ORGANISM: Human respiratory syncytial virus

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
```

-continued

```
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 2
<211> LENGTH: 574
<212> TYPE: PRT
<213> ORGANISM: Human respiratory syncytial virus

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
```

-continued

```
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 3
<211> LENGTH: 568
<212> TYPE: PRT
<213> ORGANISM: Human respiratory syncytial virus

<400> SEQUENCE: 3

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln His Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Phe Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 4
<211> LENGTH: 574
<212> TYPE: PRT

-continued

<213> ORGANISM: Human respiratory syncytial virus

<400> SEQUENCE: 4

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln His Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Phe Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400
```

-continued

```
Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 5
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190
```

```
Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 6
<211> LENGTH: 574
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 6

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Cys Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Phe Lys Val
180 185 190

Leu Asp Leu Lys Asn Tyr Ile Asp Lys Gln Leu Leu Pro Ile Leu Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Cys Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

-continued

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Thr Gly Lys Ser Thr Thr Asn Ile Met Ile Thr
515 520 525

Thr Ile Ile Ile Val Ile Ile Val Val Leu Leu Ser Leu Ile Ala Ile
530 535 540

Gly Leu Leu Leu Tyr Cys Lys Ala Lys Asn Thr Pro Val Thr Leu Ser
545 550 555 560

Lys Asp Gln Leu Ser Gly Ile Asn Asn Ile Ala Phe Ser Lys
565 570

<210> SEQ ID NO 7
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Phe Lys Val

```
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 8
<211> LENGTH: 574
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
```

385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu His Asn Val Asn Thr Gly Lys Ser Thr Thr Asn Ile Met Ile Thr
515 520 525

Thr Ile Ile Ile Val Ile Ile Val Val Leu Leu Ser Leu Ile Ala Ile
530 535 540

Gly Leu Leu Leu Tyr Cys Lys Ala Lys Asn Thr Pro Val Thr Leu Ser
545 550 555 560

Lys Asp Gln Leu Ser Gly Ile Asn Asn Ile Ala Phe Ser Lys
565 570

<210> SEQ ID NO 9
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Cys Lys Val Leu His Leu
145 150 155 160

Glu Gly Glu Val Asn Lys Ile Lys Ser Ala Leu Leu Ser Thr Asn Lys
165 170 175

-continued

```
Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 10
<211> LENGTH: 574
<212> TYPE: PRT

-continued

<213> ORGANISM: Artificial Sequence
<220> FEATURE:
<223> OTHER INFORMATION: Description of Artificial Sequence: Synthetic
polypeptide

<400> SEQUENCE: 10

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380
```

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 11
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Tyr Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 12
<211> LENGTH: 568

-continued

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 12

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Tyr Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380
```

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu Ser Ala Ile Gly Gly Tyr Ile Pro Glu Ala Pro Arg Asp Gly Gln
515 520 525

Ala Tyr Val Arg Lys Asp Gly Glu Trp Val Leu Leu Ser Thr Phe Leu
530 535 540

Gly Gly Leu Val Pro Arg Gly Ser His His His His His His Ser Ala
545 550 555 560

Trp Ser His Pro Gln Phe Glu Lys
565

<210> SEQ ID NO 13
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys

-continued

```
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 14

<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Tyr Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
```

370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu Ser Ala Ile Gly Gly Tyr Ile Pro Glu Ala Pro Arg Asp Gly Gln
515 520 525

Ala Tyr Val Arg Lys Asp Gly Glu Trp Val Leu Leu Ser Thr Phe Leu
530 535 540

Gly Gly Leu Val Pro Arg Gly Ser His His His His His His Ser Ala
545 550 555 560

Trp Ser His Pro Gln Phe Glu Lys
565

<210> SEQ ID NO 15
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

-continued

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

-continued

<210> SEQ ID NO 16
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 17
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Tyr Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160
```

-continued

```
Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 18
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Tyr Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Tyr Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365
```

```
Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 19
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Tyr Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu Tyr Leu
```

-continued

```
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 20
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 20

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Tyr Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp

```
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Tyr Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565


<210> SEQ ID NO 21
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140
```

-continued

```
Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Tyr Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Tyr Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
```

565

<210> SEQ ID NO 22
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Tyr Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Ser Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

-continued

```
Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Tyr Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 23
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140
```

```
Gly Ser Tyr Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560
```

```
Trp Ser His Pro Gln Phe Glu Lys
                565


<210> SEQ ID NO 24
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Tyr Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu Ser Ala Ile Gly Gly Tyr Ile Pro Glu Ala Pro Arg Asp Gly Gln
515 520 525

Ala Tyr Val Arg Lys Asp Gly Glu Trp Val Leu Leu Ser Thr Phe Leu
530 535 540

Gly Gly Leu Val Pro Arg Gly Ser His His His His His His Ser Ala
545 550 555 560

Trp Ser His Pro Gln Phe Glu Lys
565

<210> SEQ ID NO 25
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val

-continued

```
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560
```

Trp Ser His Pro Gln Phe Glu Lys
                565

<210> SEQ ID NO 26
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Tyr Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
```

340 345 350

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Val Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu Ser Ala Ile Gly Gly Tyr Ile Pro Glu Ala Pro Arg Asp Gly Gln
515 520 525

Ala Tyr Val Arg Lys Asp Gly Glu Trp Val Leu Leu Ser Thr Phe Leu
530 535 540

Gly Gly Leu Val Pro Arg Gly Ser His His His His His His Ser Ala
545 550 555 560

Trp Ser His Pro Gln Phe Glu Lys
565

<210> SEQ ID NO 27
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

-continued

```
Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
```

545 550 555 560

Trp Ser His Pro Gln Phe Glu Lys
565

<210> SEQ ID NO 28
<211> LENGTH: 568
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Cys Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Phe Lys Val
180 185 190

Leu Asp Leu Lys Asn Tyr Ile Asp Lys Gln Leu Leu Pro Ile Leu Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Cys Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565


<210> SEQ ID NO 29
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125
```

```
Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540
```

Gly Gly Leu Val Pro Arg Gly Ser His His His His His His Ser Ala
545 550 555 560

Trp Ser His Pro Gln Phe Glu Lys
565

<210> SEQ ID NO 30
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Ser Ile Ser Asn Ile Glu Thr Val Ile Glu Phe Gln
210 215 220

Gln Tyr Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Asn Asn Val Gln Ile Val Arg Gln Gln Ser Tyr Ser Ile
275 280 285

Met Ser Ile Ile Lys Glu Glu Val Leu Ala Tyr Val Val Gln Leu Pro
290 295 300

Leu Tyr Gly Val Ile Asp Thr Pro Cys Trp Lys Leu His Thr Ser Pro
305 310 315 320

Leu Cys Thr Thr Asn Thr Lys Glu Gly Ser Asn Ile Cys Leu Thr Arg
325 330 335

Thr Asp Arg Gly Trp Tyr Cys Asp Asn Ala Gly Ser Val Ser Phe Phe
340 345 350

Pro Gln Ala Glu Thr Cys Lys Val Gln Ser Asn Arg Val Phe Cys Asp
355 360 365

Thr Met Asn Ser Leu Thr Leu Pro Ser Glu Val Asn Leu Cys Asn Val
370 375 380

Asp Ile Phe Asn Pro Lys Tyr Asp Cys Lys Ile Met Thr Ser Lys Thr
385 390 395 400

Asp Val Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Gln Glu Gly
450 455 460

Lys Ser Leu Tyr Tyr Lys Gly Glu Pro Ile Ile Asn Phe Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Lys Ser Asp Glu Leu
500 505 510

Leu Ser Ala Ile Gly Gly Tyr Ile Pro Glu Ala Pro Arg Asp Gly Gln
515 520 525

Ala Tyr Val Arg Lys Asp Gly Glu Trp Val Leu Leu Ser Thr Phe Leu
530 535 540

Gly Gly Leu Val Pro Arg Gly Ser His His His His His His Ser Ala
545 550 555 560

Trp Ser His Pro Gln Phe Glu Lys
565

<210> SEQ ID NO 31
<211> LENGTH: 568
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Asn Asn Arg Ala Arg Arg Glu Leu Pro
100 105 110

Arg Phe Met Asn Tyr Thr Leu Asn Asn Ala Lys Lys Thr Asn Val Thr

-continued

```
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Tyr Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540
```

```
Gly Gly Leu Val Pro Arg Gly Ser His His His His His His Ser Ala
545                 550                 555                 560

Trp Ser His Pro Gln Phe Glu Lys
                565


<210> SEQ ID NO 32
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
```

```
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Tyr Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565
```

<210> SEQ ID NO 33
<211> LENGTH: 1725
<212> TYPE: DNA
<213> ORGANISM: Human respiratory syncytial virus

<400> SEQUENCE: 33

```
atggagttgc taatcctcaa agcaaatgca attaccacaa tcctcactgc agtcacattt     60

tgttttgctt ctggtcaaaa catcactgaa gaattttatc aatcaacatg cagtgcagtt    120

agcaaaggct atcttagtgc tctgagaact ggttggtata ccagtgttat aactatagaa    180

ttaagtaata tcaagaaaaa taagtgtaat ggaacagatg ctaaggtaaa attgataaaa    240

caagaattag ataaatataa aaatgctgta acagaattgc agttgctcat gcaaagcaca    300

ccagcaacaa acaatcgagc cagaagagaa ctaccaaggt ttatgaatta tacactcaac    360

aatgccaaaa aaaccaatgt aacattaagc aagaaaagga aaagaagatt tcttggtttt    420

ttgttaggtg ttggatctgc aatcgccagt ggcgttgctg tatctaaggt cctgcaccta    480

gaaggggaag tgaacaagat caaaagtgct ctactatcca caaacaaggc tgtagtcagc    540

ttatcaaatg gagtcagtgt cttaaccagc aaagtgttag acctcaaaaa ctatatagat    600

aaacaattgt tacctattgt gaacaagcaa agctgcagca tatcaaatat agaaactgtg    660

atagagttcc aacaaaagaa caacagacta ctagagatta ccagggaatt tagtgttaat    720
```

-continued

```
gcaggtgtaa ctacacctgt aagcacttac atgttaacta atagtgaatt attgtcatta    780

atcaatgata tgcctataac aaatgatcag aaaaagttaa tgtccaacaa tgttcaaata    840

gttagacagc aaagttactc tatcatgtcc ataataaaag aggaagtctt agcatatgta    900

gtacaattac cactatatgg tgttatagat acaccctgtt ggaaactaca cacatcccct    960

ctatgtacaa ccaacacaaa agaagggtcc aacatctgtt taacaagaac tgacagagga   1020

tggtactgtg acaatgcagg atcagtatct ttcttcccac aagctgaaac atgtaaagtt   1080

caatcaaatc gagtattttg tgacacaatg aacagtttaa cattaccaag tgaagtaaat   1140

ctctgcaatg ttgacatatt caaccccaaa tatgattgta aaattatgac ttcaaaaaca   1200

gatgtaagca gctccgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggta acacattata ttatgtaaat   1380

aagcaagaag gtaaaagtct ctatgtaaaa ggtgaaccaa taataaattt ctatgaccca   1440

ttagtattcc cctctgatga atttgatgca tcaatatctc aagtcaacga gaagattaac   1500

cagagcctag catttattcg taaatccgat gaattattac ataatgtaaa tgccggtaaa   1560

tccaccacaa atatcatgat aactactata attatagtga ttatagtaat attgttatca   1620

ttaattgctg ttggactgct cttatactgt aaggccagaa gcacaccagt cacactaagc   1680

aaagatcaac tgagtggtat aaataatatt gcatttagta actaa                   1725
```

<210> SEQ ID NO 34
<211> LENGTH: 1725
<212> TYPE: DNA
<213> ORGANISM: Human respiratory syncytial virus

<400> SEQUENCE: 34

```
atggagttgc tgatccacag gtcaagtgca atcttcctaa ctcttgctat taatgcattg     60

tacctcacct caagtcagaa cataactgag gagttttacc aatcgacatg tagtgcagtt    120

agcagaggtt attttagtgc tttaagaaca ggttggtata ccagtgtcat aacaatagaa    180

ttaagtaata taacagaaac caaatgcaat ggaactgaca ctaaagtaaa acttataaaa    240

caagaattag ataagtataa gaatgcagta acagaattac agctacttat gcaaaacacg    300

ccagctgcca acaaccgggc cagaagagaa gcaccacagc acatgaacta cacaatcaat    360

accactaaaa acctaaatgt atcaataagc aagaagagga aacgaagatt tctgggcttc    420

ttgttaggtg taggatctgc aatagcaagt ggtatagctg tatccaaagt tctacacctt    480

gaaggagaag tgaacaaaat caaaaatgct ttgttgtcta caaacaaagc tgtagtcagt    540

ctatcaaatg ggtcagtgt tttaaccagc aaagtgttag atctcaagaa ttacataaat    600

aaccaattat tacccatagt aaatcaacag agctgtcgca tcttcaacat tgaaacagtt    660

atagaattcc aacagaagaa tagcagattg ttggaaatca ccagagaatt tagtgtcaat    720

gcaggtgtaa caacaccttt aagcacttac atgttaacaa acagtgagtt actatcattg    780

atcaatgata tgcctataac aaatgatcag aaaaaattaa tgtcaagcaa tgttcagata    840

gtaaggcaac aaagttattc tatcatgtct ataataaagg aagaagtcct tgcatatgtt    900

gtacagctac ctatctatgg tgtaatagat acaccttgct ggaaattaca cacatcacct    960

ctatgcacca ccaacatcaa agaaggatca aatatttgtt taacaaggac tgatagagga   1020

tggtattgtg ataatgcagg atcagtatcc ttcttcccac aggctgacac ttgcaaagta   1080

cagtccaatc gagtattttg tgacactatg aacagtttga cattaccaag tgaagtcagc   1140
```

ctttgtaaca ctgacatatt caattccaag tatgactgca aaattatgac atcaaaaaca 1200
gacataagca gctcagtaat tacttctctt ggagctatag tgtcatgtta tggtaaaact 1260
aaatgcactg catccaataa aaatcgtggg attataaaga cattttctaa tggttgtgac 1320
tatgtgtcaa acaaaggagt agatactgtg tcagtgggca acactttata ctatgtaaac 1380
aagctggaag gcaagaacct ttatgtaaaa ggggaaccta taataaatta ctatgatcct 1440
ctagtgtttc cttctgatga gtttgatgca tcaatatctc aagtcaatga aaaaatcaat 1500
caaagtttag cttttattcg taaatctgat gaattactac ataatgtaaa tactggcaaa 1560
tctactacaa atattatgat aactacaatt attatagtaa tcattgtagt attgttatca 1620
ttaatagcta ttggtttact gttgtattgc aaagccaaaa acacaccagt tacactaagc 1680
aaagaccaac taagtggaat caataatatt gcattcagca aatag 1725

<210> SEQ ID NO 35
<211> LENGTH: 1725
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
atggagctgc tcatcctgaa ggccaacgcc atcaccacca tcctcaccgc cgtgaccttc 60
tgcttcgcca gcggccagaa tatcaccgag gagttctacc agagcacctg cagcgccgtg 120
agcaagggct acctgagcgc cctgagaacc ggctggtaca ccagcgtgat caccatcgag 180
ctgagcaaca tcaagaagaa caagtgcaac ggcaccgacg ccaaggtgaa gctcatcaag 240
caggagctgg acaagtacaa gaacgccgtg accgagctgc agctgctcat gcagagcacc 300
caggccacca acaacagggc cagaagggag ctgccccggt tcatgaacta caccctgaac 360
aacgccaaga aaaccaacgt gaccctgagc aagaagcgga agcggagatt cctgggcttc 420
ctgctgggcg tgggcagcgc catcgccagc ggagtggccg tgtccaaggt gctgcacctg 480
gagggcgagg tgaacaagat caagagcgcc ctgctgagca ccaacaaggc cgtggtgagc 540
ctgagcaacg gcgtgagcgt gctcaccagc aaggtgctgg atctgaagaa ctacatcgac 600
aagcagctgc tgcccatcgt gaacaagcag agctgcagca tcagcaacat cgagaccgtg 660
atcgagttcc agcagaagaa caaccggctg ctggagatca ccagggagtt cagcgtgaac 720
gccggcgtga ccacccccgt gagcacctac atgctcacca acagcgagct gctgagcctc 780
atcaacgaca tgcccatcac caacgaccag aagaagctca tgagcaacaa cgtgcagatc 840
gtgcggcagc agagctactc catcatgagc atcatcaagg aggaggtgct ggcctacgtg 900
gtgcagctgc ccctgtacgg cgtgatcgat accccttgct ggaagctgca caccagcccc 960
ctgtgcacca ccaacaccaa ggagggcagc aacatctgcc tcaccaggac cgatagaggc 1020
tggtactgcg acaacgccgg cagcgtgtca ttctttccac aggccgagac ctgcaaggtg 1080
cagagcaacc gggtgttctg cgacaccatg aacagcctca ccctgcccag cgaagtgaac 1140
ctgtgcaacg tggacatctt caaccccaag tacgactgca agatcatgac cagcaagacc 1200
gacgtgagca gcagcgtgat taccagcctg ggcgccatcg tgagctgcta cggcaagacc 1260
aagtgcaccg ccagcaacaa gaaccggggg atcatcaaga ccttcagcaa cggctgcgac 1320
tacgtgagca acaagggcgt ggataccgtg agcgtgggca acaccctgta ctacgtgaat 1380
aagcaggagg gcaagagcct gtacgtgaag ggcgagccca tcatcaactt ctacgacccc 1440

```
ctggtgttcc ctagcgacga gttcgatgcc agcatcagcc aggtgaacga gaagatcaac   1500

cagagcctgg ccttcatcag gaagagcgac gagctgctgc acaatgtgaa tgccggcaag   1560

agcaccacca atatcatgat caccacaatc atcatcgtga tcattgtgat cctgctgtcc   1620

ctcatcgccg tgggcctgct gctgtactgc aaggccagaa gcacccctgt gaccctgtcc   1680

aaggatcagc tgagcggcat caacaatatc gccttctcca actga                   1725
```

```
<210> SEQ ID NO 36
<211> LENGTH: 1725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

atggaactgc tgatcctgaa ggccaacgcc atcaccacca tcctgaccgc cgtgaccttc     60

tgcttcgcct ccggccagaa catcaccgag gaattctacc agtctacctg ctccgccgtg    120

tccaagggct acctgtctgc tctgagaacc ggctggtaca cctccgtgat caccatcgag    180

ctgtccaaca tcaagaaaaa caagtgcaac ggcaccgacg ccaaagtgaa gctgatcaag    240

caggaactgg acaagtacaa gaatgccgtg accgaactgc agctgctgat gcagtctacc    300

caggccacca acaaccgggc cagacgcgag ctgcccagat tcatgaacta caccctgaac    360

aacgccaaaa agaccaacgt gaccctgtcc aagaagcgga agcggcggtt cctgggcttt    420

ctgctgggag tgggctccgc tatcgcttct ggcgtggccg tgtctaaggt gctgcacctg    480

gaaggcgaag tgaacaagat caagtccgcc ctgctgagca ccaacaaggc cgtggtgtcc    540

ctgagcaacg gcgtgtccgt gctgacctcc aaggtgctgg atctgaagaa ctacatcgac    600

aaacagctgc tgcccatcgt gaacaagcag tcctgctcca tctccaacat cgagacagtg    660

atcgagttcc agcagaagaa caaccggctg ctggaaatca cccgcgagtt ctccgtgaat    720

gccggcgtga ccacccccgt gtccacctac atgctgacca actccgagct gctgtctctg    780

atcaacgaca tgcccatcac caacgaccag aaaaagctga tgtccaacaa cgtgcagatc    840

gtgcggcagc agtcctacag catcatgtcc atcatcaaag aagaggtgct ggcctacgtg    900

gtgcagctgc ctctgtacgg cgtgatcgac acccccctgct ggaagctgca caccagccct    960

ctgtgcacca ccaacaccaa agagggcagc aacatctgcc tgacccggac cgacagaggc   1020

tggtactgtg acaacgctgg ctccgtctca ttctttccac aagccgagac atgcaaggtg   1080

cagtccaacc gggtgttctg cgacaccatg aactccctga ccctgccctc tgaagtgaac   1140

ctgtgcaacg tggacatctt caaccctaag tacgactgca agatcatgac cagcaagacc   1200

gacgtgtcca gctctgtgat cacctccctg ggcgccatcg tgtcctgcta cggcaagacc   1260

aagtgcaccg cctccaacaa gaaccggggc atcatcaaga ccttctccaa cggctgcgac   1320

tatgtgtcta acaagggcgt ggacaccgtg tctgtgggca acaccctgta ctacgtgaac   1380

aaacaggaag gcaagtccct gtacgtgaag ggcgagccta tcatcaactt ctacgacccc   1440

ctggtgttcc ccagcgacga gttcgacgcc tccatcagcc aagtgaacga gaagatcaac   1500

cagtccctgg ccttcatccg gaagtccgat gagctgctgc acaatgtgaa cgccggcaag   1560

tccaccacca atatcatgat caccacaatc atcatcgtga ttatcgtgat cctgctgagc   1620

ctgatcgccg tgggcctgct gctgtactgc aaggccagat ccacccctgt gacactgagc   1680

aaggaccagc tgtccggcat caacaatatc gccttcagca actga                   1725
```

<210> SEQ ID NO 37
<211> LENGTH: 1725
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
atggaactgc tgatcctgaa ggctaacgct atcaccacca tcctgaccgc tgtgaccttc 60
tgcttcgctt ccggccagaa catcaccgag gaattctacc agtctacctg ctccgctgtg 120
tccaagggtt acctgtccgc tctgcgtacc ggctggtaca cctccgtgat caccatcgag 180
ctgtccaaca tcaagaagaa caagtgcaac ggcaccgacg ctaaagtgaa gctgatcaag 240
caagagctgg acaagtacaa gaacgctgtc accgaactgc agctgctgat gcagtccacc 300
caggctacca acaaccgtgc tcgtcgcgag ctgccccgtt tcatgaacta caccctgaac 360
aacgccaaga agaccaacgt caccctgtcc aagaagcgca agcgccgttt cctgggtttc 420
ctgctgggtg tcggttccgc tatcgcctcc ggtgtcgctg tctctaaggt gctgcacctc 480
gagggcgaag tgaacaagat caagtccgcc ctgctgtcca ccaacaaggc tgtggtgtcc 540
ctgtctaacg gtgtctccgt gctgacctcc aaggtcctgg acctgaagaa ctacatcgac 600
aagcaactgc tgcccatcgt gaacaagcag tcctgctcca tctccaacat cgagactgtg 660
atcgagttcc agcaaaagaa caaccgcctg ctcgagatca cccgcgagtt ctccgtgaac 720
gctggtgtca ccacccccgt gtccacctac atgctgacca actccgagct gctgtccctg 780
atcaacgaca tgcccatcac caacgaccaa aagaagctga tgtccaacaa cgtgcagatc 840
gtgcgtcagc agtcctactc tatcatgagc atcatcaagg aagaggtgct ggcttacgtg 900
gtgcagctgc ccctgtacgg tgtcatcgac accccctgct ggaagctgca cacctcccca 960
ctgtgcacca ccaacaccaa ggaaggttcc aacatctgcc tgacccgtac cgaccgtggc 1020
tggtactgcg acaacgctgg ttccgtttca ttcttcccac aagccgagac ttgcaaggtg 1080
cagtccaacc gtgtgttctg cgacaccatg aactccctga ccctgccctc cgaagtcaac 1140
ctgtgcaacg tggacatctt caaccctaag tacgactgca agatcatgac cagcaagacc 1200
gacgtgtcct cctctgtcat cacctccctg ggtgctatcg tgtcctgcta cggcaagacc 1260
aagtgcaccg cttccaacaa gaaccgcggt atcatcaaga ccttctccaa cggttgcgac 1320
tacgtcagca acaagggcgt ggacaccgtg tccgtgggca acaccctgta ctacgtcaac 1380
aagcaagagg gcaagtccct gtacgtgaag ggcgagccca tcatcaactt ctacgacccc 1440
ctggtgttcc catccgacga gttcgacgct tccatctccc aagtgaacga gaagatcaac 1500
cagtccctgg ctttcatccg caagtccgac gagctgctcc acaacgtcaa cgctggcaag 1560
tccaccacta acatcatgat cactaccatc atcatcgtga tcatcgtcat cctgctgagc 1620
ctgatcgctg tgggcctgct gctgtactgc aaggctcgtt ccacccctgt gactctgtcc 1680
aaggaccagc tgtccggtat caacaacatc gccttcagca actaa 1725

<210> SEQ ID NO 38
<211> LENGTH: 1725
<212> TYPE: DNA
<213> ORGANISM: Artificial Sequence
<220> FEATURE:
<223> OTHER INFORMATION: Description of Artificial Sequence: Synthetic
polynucleotide -continued

<400> SEQUENCE: 38
atggaactgc tgatcctgaa ggccaacgcc atcaccacca tcctgaccgc cgtgaccttc 60
tgcttcgcca gcggccagaa catcaccgag gaattctacc agagcacctg tagcgccgtg 120
tccaagggct acctgagcgc cctgagaacc ggctggtaca ccagcgtgat caccatcgag 180
ctgagcaaca tcaagaaaaa caagtgcaac ggcaccgacg ccaaagtgaa gctgatcaag 240
caggaactgg acaagtacaa gaacgccgtg acagaactgc agctgctgat gcagagcacc 300
caggccacca acaacagagc cagacgcgag ctgcccagat tcatgaacta caccctgaac 360
aacgccaaaa agaccaacgt gaccctgagc aagaagagga agcgcagatt cctgggcttc 420
ctgctgggcg tgggcagcgc tattgcttct ggcgtggccg tgtctaaggt gctgcacctg 480
gaaggcgaag tgaacaagat caagtccgcc ctgctgagca ccaacaaggc cgtggtgtct 540
ctgagcaacg gcgtgtccgt gctgaccagc aaggtgctgg atctgaagaa ctacatcgac 600
aaacagctgc tgcccatcgt gaacaagcag agctgcagca tcagcaacat cgagacagtg 660
atcgagttcc agcagaagaa caaccggctg ctggaaatca cccgcgagtt cagcgtgaac 720
gctggcgtga ccaccccccgt gtccacctac atgctgacca acagcgagct gctgagcctg 780
atcaacgaca tgcccatcac caacgaccag aaaaagctga tgagcaacaa cgtgcagatc 840
gtgcggcagc agagctactc catcatgagc atcatcaaag aagaggtgct ggcctacgtg 900
gtgcagctgc ctctgtacgg cgtgatcgac accccctgct ggaagctgca caccagccct 960
ctgtgcacca ccaacaccaa agagggctcc aacatctgcc tgaccagaac cgacagaggc 1020
tggtactgcg acaacgccgg ctccgtctca ttctttccac aagccgagac atgcaaggtg 1080
cagagcaaca gagtgttctg cgacaccatg aacagcctga ccctgccctc tgaagtgaac 1140
ctgtgcaacg tggacatctt caaccctaag tacgactgca agatcatgac ctccaagacc 1200
gacgtgtcca gctccgtgat cacaagcctg ggcgccatcg tgtcctgcta cggcaagacc 1260
aagtgcaccg ccagcaacaa gaacagggga atcatcaaga ccttcagcaa cggctgcgac 1320
tacgtgtcca acaagggggt ggacaccgtg tctgtgggca acaccctgta ctacgtgaac 1380
aaacaggaag gcaagagcct gtacgtgaag ggcgagccca tcatcaactt ctacgacccc 1440
ctggtgttcc ccagcgacga gttcgacgcc agcatctccc aagtgaacga gaagatcaac 1500
cagagcctgg ccttcatcag aaagtccgat gagctgctgc acaatgtgaa cgccggcaag 1560
agcaccacaa acatcatgat caccactatc atcatcgtga tcattgtgat cctgctgtcc 1620
ctgatcgccg tgggcctgct gctgtactgc aaggccagat ccaccccctgt gaccctgtcc 1680 aaggaccagc tgagcggcat caacaatatc gccttctcca actga 1725

<210> SEQ ID NO 39
<211> LENGTH: 1725
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
atggaactgc tgatccacag aagcagcgcc atcttcctga ccctggccat caacgccctg 60
tacctgacca gcagccagaa catcaccgag gaattctacc agagcacctg tagcgccgtg 120
tcccggggct actttagcgc cctgagaacc ggctggtaca ccagcgtgat caccatcgag 180
ctgagcaata tcaccgagac aaagtgcaac ggcaccgaca ccaaagtgaa gctgatcaag 240

-continued

```
caggaactgg acaagtacaa gaacgccgtg accgaactgc agctgctgat gcagaatacc    300

cctgccgcca acaaccgggc cagaagagaa gccccccagc acatgaacta caccatcaac    360

accaccaaga acctgaacgt gtccatcagc aagaagcgga agcggcggtt cctgggcttt    420

ctgctgggag tgggaagcgc cattgccagc ggaatcgccg tgtctaaggt gctgcacctg    480

gaaggcgaag tgaacaagat caagaatgcc ctgctgagca ccaacaaggc cgtggtgtcc    540

ctgagcaacg gcgtgtccgt gctgacctcc aaggtgctgg atctgaagaa ctacatcaac    600

aaccagctgc tgcccatcgt gaaccagcag agctgccgga tcttcaacat cgagacagtg    660

atcgagttcc agcagaagaa cagcaggctg ctggaaatca cccgcgagtt cagcgtgaac    720

gctggcgtga ccacacccct gagcacctac atgctgacca acagcgagct gctgtccctg    780

atcaatgaca tgcccatcac caacgaccag aaaaagctga tgagcagcaa cgtgcagatc    840

gtgcggcagc agtcctacag catcatgagc atcatcaaag aagaggtgct ggcctacgtg    900

gtgcagctgc ctatctacgg cgtgatcgac acccccctgct ggaagctgca caccagccct    960

ctgtgcacca ccaacatcaa agagggcagc aacatctgcc tgaccagaac cgaccggggc   1020

tggtactgcg ataatgccgg ctccgtctca ttctttccac aagccgatac ctgcaaggtg   1080

cagagcaacc gggtgttctg cgacaccatg aacagcctga cactgcccag cgaagtgtcc   1140

ctgtgtaaca ccgacatctt caactctaag tacgactgca agatcatgac cagcaagacc   1200

gacatcagct cctccgtgat cacaagcctg ggcgccatcg tgtcctgcta cggcaagacc   1260

aagtgcaccg ccagcaacaa gaaccgggga atcatcaaga ccttcagcaa cggctgcgac   1320

tacgtgtcca acaagggggt ggacaccgtg tctgtgggca acaccctgta ctacgtgaac   1380

aagctggaag ggaagaatct gtacgtgaag ggcgagccca tcatcaacta ctacgacccc   1440

ctggtgttcc ccagcgacga gttcgatgcc agcatcagcc aagtgaacga gaagatcaac   1500

cagagcctgg ccttcatcag aaagtccgat gagctgctgc acaatgtgaa caccggcaag   1560

tccaccacaa atatcatgat caccaccatc attatcgtga tcatcgtggt gctgctgagc   1620

ctgatcgcca tcggcctgct gctgtactgc aaggccaaga acacccccgt gaccctgtcc   1680

aaggatcagc tgagcggcat caacaatatc gccttctcca agtga                   1725
```

<210> SEQ ID NO 40
<211> LENGTH: 1725
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40

```
atggaactgc tgatccaccg gtcctccgcc atcttcctga ccctggccat caacgccctg     60

tacctgacct cctcccagaa catcaccgag gaattctacc agtctacctg ctccgccgtg    120

tcccggggct acttctctgc tctgagaacc ggctggtaca cctccgtgat caccatcgag    180

ctgtccaata tcaccgagac aaagtgcaac ggcaccgaca ccaaagtgaa gctgatcaag    240

caggaactgg acaagtacaa gaacgccgtg accgaactgc agctgctgat gcagaatacc    300

cctgccgcca acaaccgggc cagaagagaa gccccccagc acatgaacta caccatcaac    360

accaccaaga acctgaacgt gtccatctcc aagaagcgga agcggcggtt cctgggcttt    420

ctgctgggag tgggctccgc tatcgcctcc ggaatcgccg tgtctaaggt gctgcacctg    480

gaaggcgaag tgaacaagat caagaatgcc ctgctgtcca ccaacaaggc cgtggtgtcc    540
```

```
ctgtccaacg gcgtgtccgt gctgacctcc aaggtgctgg atctgaagaa ctacatcaac    600

aaccagctgc tgcccatcgt gaaccagcag tcctgccgga tcttcaacat cgagacagtg    660

atcgagttcc agcagaagaa ctcccggctg ctggaaatca cccgcgagtt ctctgtgaat    720

gccggcgtga ccaccccct gtccacctac atgctgacca actccgagct gctgtccctg    780

atcaacgaca tgcccatcac caacgaccag aaaaagctga tgtcctccaa cgtgcagatc    840

gtgcggcagc agagctactc catcatgtcc attatcaaag aagaggtgct ggcctacgtg    900

gtgcagctgc ctatctacgg cgtgatcgac accccctgct ggaagctgca caccagccct    960

ctgtgcacca ccaacatcaa agagggctcc aacatctgcc tgaccagaac cgaccggggc   1020

tggtactgtg acaacgctgg ctccgtctca ttctttccac aagccgatac ctgcaaggtg   1080

cagtccaacc gggtgttctg cgacaccatg aattctctga ccctgccctc cgaagtgtct   1140

ctgtgtaaca ccgacatctt caactctaag tacgactgca agatcatgac cagcaagacc   1200

gatatctcca gctctgtgat cacctccctg ggcgccatcg tgtcctgcta cggcaagacc   1260

aagtgcaccg cctccaacaa gaaccggggc atcatcaaga ccttctccaa cggctgcgac   1320

tacgtgtcca acaagggggt ggacaccgtg tctgtgggca acaccctgta ctacgtgaac   1380

aagctggaag ggaagaatct gtacgtgaag ggcgagccca tcatcaacta ctacgacccc   1440

ctggtgttcc ccagcgacga gttcgacgcc tccatcagcc aagtgaacga gaagatcaac   1500

cagtccctgg ccttcatccg gaagtccgat gagctgctgc acaatgtgaa caccggcaag   1560

tccaccacaa atatcatgat caccaccatc attatcgtga tcatcgtggt gctgctgagc   1620

ctgatcgcca tcggcctgct gctgtactgc aaggccaaga acacccccgt gaccctgagc   1680

aaggaccagc tgtccggcat caacaatatc gccttcagca agtga                   1725
```

<210> SEQ ID NO 41
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
atggaactgc tgatccaccg ttcctccgct atcttcctga ccctggctat caacgctctg     60

tacctgacct cctcccagaa catcaccgag gaattctacc agtctacctg ctccgctgtg    120

tcccgtggtt acttctccgc tctgcgtacc ggctggtaca cctccgtgat caccatcgag    180

ctgtccaaca tcactgagac taagtgcaac ggcaccgaca ccaaagtgaa gctgatcaag    240

caagagctgg acaagtacaa gaacgctgtg accgaactgc agctgctgat gcagaacacc    300

cccgctgcta acaaccgtgc tcgtcgcgaa gctccccagc acatgaacta caccatcaac    360

accaccaaga acctgaacgt gtccatctcc aagaagcgca agcgccgttt cctgggtttc    420

ctgctgggtg tcggttccgc tatcgcttcc ggtatcgctg tctccaaggt gctgcacctc    480

gagggcgaag tgaacaagat caagaacgcc ctgctgtcca ccaacaaggc tgtggtgtcc    540

ctgtccaacg gtgtctccgt gctgacctcc aaggtcctcg acctgaagaa ctacatcaac    600

aaccagctgc tgcccatcgt gaaccagcag tcctgccgta tcttcaacat cgagactgtg    660

atcgagttcc agcagaagaa ctcccgtctg ctcgagatca cccgcgagtt ctccgtgaac    720

gctggtgtca ccaccccct gtccacctac atgctgacca actccgagct gctgtccctg    780

atcaacgaca tgcccatcac caacgaccaa aagaagctga tgtcctccaa cgtgcagatc    840
```

gtgcgtcagc agtcttactc catcatgtcc atcatcaagg aagaggtgct ggcttacgtg 900
gtgcagctgc ctatctacgg tgtcatcgac accccctgct ggaagctgca cacctcccca 960
ctgtgcacca ccaacatcaa ggaaggttcc aacatctgcc tgacccgtac cgaccgtggc 1020
tggtactgcg acaacgctgg ttccgtttca ttcttcccac aagccgacac ttgcaaggtg 1080
cagtccaacc gtgtgttctg cgacaccatg aactccctga ctctgccctc cgaggtgtcc 1140
ctctgcaaca ccgacatctt caactctaag tacgactgca agatcatgac ctctaagact 1200
gacatctcct ccagcgtcat cacctccctg ggtgctatcg tgtcctgcta cggcaagacc 1260
aagtgcaccg cttccaacaa gaaccgcggt atcatcaaga ccttctccaa cggttgcgac 1320
tacgtgtcca acaagggcgt ggacaccgtg tccgtgggca acaccctgta ctacgtgaac 1380
aagctcgagg gcaagaacct ctacgtgaag ggcgagccta tcatcaacta ctacgacccc 1440
ctggtgttcc catccgacga gttcgacgct tccatctccc aagtgaacga gaagatcaac 1500
cagtccctgg ctttcatccg caagtccgac gagctgctcc acaacgtgaa caccggcaag 1560
tccactacta acatcatgat caccactatc atcatcgtga tcatcgtcgt gctgctgagc 1620
ctgatcgcta tcggcctgct gctgtactgc aaggctaaga acactcccgt gaccctgtct 1680
aaggaccagc tgtccggtat caacaacatc gccttcagca agtaa 1725

<210> SEQ ID NO 42
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
atggaactgc tgatccacag aagcagcgcc atcttcctga ccctggccat caacgccctg 60
tacctgacca gcagccagaa catcaccgag gaattctacc agagcacctg tagcgccgtg 120
tccagaggct acttcagcgc cctgagaacc ggctggtaca ccagcgtgat caccatcgag 180
ctgagcaaca tcacagagac aaagtgcaac ggcaccgaca ccaaagtgaa gctgatcaag 240
caggaactgg acaagtacaa gaacgccgtg accgaactgc agctgctgat gcagaacacc 300
cctgccgcca acaacagagc cagaagagaa gccccccagc acatgaacta caccatcaac 360
accaccaaga acctgaacgt gtccatcagc aagaagagga agagaagatt cctgggcttc 420
ctgctgggcg tgggcagcgc tatcgcttct ggaatcgccg tgtctaaggt gctgcacctg 480
gaaggcgaag tgaacaagat caagaacgct ctgctgagca ccaacaaggc cgtggtgtcc 540
ctgagcaacg gcgtgtccgt gctgacctcc aaggtgctgg atctgaagaa ctacatcaac 600
aaccagctgc tgcccatcgt gaaccagcag agctgcagaa tcttcaacat cgagacagtg 660
atcgagttcc agcagaagaa cagcaggctg ctggaaatca cccgcgagtt cagcgtgaac 720
gctggcgtga ccacacccct gagcacctac atgctgacca acagcgagct gctgtctctg 780
atcaacgaca tgcccatcac caacgaccag aaaaagctga tgagcagcaa cgtgcagatc 840
gtgcggcagc agtcctacag catcatgagc atcatcaaag aagaggtgct ggcctacgtg 900
gtgcagctgc ctatctacgg cgtgatcgac accccctgct ggaagctgca caccagccct 960
ctgtgcacca ccaacatcaa agagggcagc aacatctgcc tgaccagaac cgacagaggc 1020
tggtactgcg acaacgccgg ctccgtctca ttctttccac aagccgacac atgcaaggtg 1080
cagagcaaca gagtgttctg cgacaccatg aacagcctga cactgcccag cgaagtgtcc 1140

```
ctgtgtaaca ccgacatctt caactctaag tacgactgca agatcatgac cagcaagacc   1200

gacatcagct cctccgtgat cacaagcctg ggcgccatcg tgtcctgcta cggcaagacc   1260

aagtgcaccg ccagcaacaa gaacagggga atcatcaaga ccttcagcaa cggctgcgac   1320

tacgtgtcca acaagggggt ggacaccgtg tctgtgggca acaccctgta ctacgtgaac   1380

aagctggaag ggaagaatct gtacgtgaag ggcgagccca tcatcaacta ctacgacccc   1440

ctggtgttcc ccagcgacga gttcgacgcc agcatcagcc aagtgaacga gaagatcaac   1500

cagagcctgg ccttcatcag aaagtccgat gagctgctgc acaatgtgaa caccggcaag   1560

tccacaacaa acatcatgat caccaccatc attatcgtga tcatcgtggt gctgctgagc   1620

ctgatcgcca tcggcctgct gctgtactgc aaggccaaga acacacccgt gaccctgtcc   1680

aaggaccagc tgagcggcat caacaatatc gccttctcca agtga                   1725
```

<210> SEQ ID NO 43
<211> LENGTH: 1707
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
atggaactgc tgatcctgaa ggccaacgcc atcaccacca tcctgaccgc cgtgaccttc     60

tgcttcgcca gcggccagaa catcaccgag gaattctacc agagcacctg cagcgccgtg    120

agcaagggct acctgagcgc cctgcggacc ggctggtaca ccagcgtgat caccatcgag    180

ctgtccaaca tcaaagaaaa caagtgcaac ggcaccgacg ccaaagtgaa gctgatcaag    240

caggaactgg acaagtacaa gaacgccgtg accgagctgc agctgctgat gcagagcacc    300

cccgccacca acaacagagc cagaagagag ctgccccggt tcatgaacta caccctgaac    360

aacgccaaga aaaccaacgt gaccctgagc aagaagagaa agagaagatt cctgggcttc    420

ctgctgggcg tgggcagcgc cattgccagc ggcgtggccg tgtgcaaagt gctgcacctg    480

gaaggcgaag tgaacaagat caagtccgcc ctgctgtcca ccaacaaggc cgtggtgtcc    540

ctgagcaacg gcgtgagcgt gctgaccttc aaggtgctgg atctgaagaa ctacatcgac    600

aagcagctgc tgcccatcct gaacaagcag agctgcagca tcagcaacat cgagacagtg    660

atcgagttcc agcagaagaa caaccggctg ctggaaatca cccgggagtt cagcgtgaac    720

gccggagtga ccacccccgt gtccacctac atgctgacca acagcgagct gctgtccctg    780

atcaatgaca tgcccatcac caacgaccag aaaaagctga tgagcaacaa cgtgcagatc    840

gtgcggcagc agagctactc catcatgtgc atcatcaaag aagaggtgct ggcctacgtg    900

gtgcagctgc ccctgtacgg cgtgatcgac accccctgct ggaagctgca caccagcccc    960

ctgtgcacaa ccaacaccaa agagggcagc aacatctgcc tgacccggac cgaccggggc   1020

tggtactgcg acaacgccgg cagcgtgtcc ttctttccac aggccgagac atgcaaggtg   1080

cagagcaacc gggtgttctg cgacaccatg aacagcctga ccctgccctc cgaagtgaac   1140

ctgtgcaacg tggacatctt caaccccaag tacgactgca agatcatgac ctccaagacc   1200

gacgtgtcca gctccgtgat cacctccctg ggcgccatcg tgtcctgcta cggcaagacc   1260

aagtgcaccg ccagcaacaa gaacagaggc atcatcaaga ccttcagcaa cggctgcgac   1320

tacgtgtcca ataagggcgt ggacaccgtg tccgtgggca acacactgta ctacgtgaat   1380

aagcaggaag gcaagagcct gtacgtgaag ggcgagccca tcatcaactt ctacgacccc   1440
```

ctggtgttcc ccagcgacga gttcgacgcc agcatcagcc aggtgaacga gaagatcaac 1500
cagagcctgg ccttcatcag aaagagcgac gaactgctgt ccgccatcgg cggctacatc 1560
cccgaggccc ccagagatgg ccaggcctac gtgcggaagg acggcgagtg ggtgctgctg 1620
tctacatttc tgggcggcct ggtgcctaga ggctctcacc accaccatca ccacagcgcc 1680
tggtcccacc cccagttcga gaagtga 1707

<210> SEQ ID NO 44
<211> LENGTH: 1707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggaactgc tgatcctgaa ggccaacgcc atcaccacca tcctgaccgc cgtgaccttc 60
tgcttcgcca gcggccagaa catcaccgag gaattctacc agagcacctg cagcgccgtg 120
agcaagggct acctgagcgc cctgcggacc ggctggtaca ccagcgtgat caccatcgag 180
ctgtccaaca tcaaagaaaa caagtgcaac ggcaccgacg ccaaagtgaa gctgatcaag 240
caggaactgg acaagtacaa gaacgccgtg accgagctgc agctgctgat gcagagcacc 300
cccgccacca acaacagagc cagaagagag ctgccccggt tcatgaacta caccctgaac 360
aacgccaaga aaaccaacgt gaccctgagc aagaagagaa agagaagatt cctgggcttc 420
ctgctgggcg tgggcagcgc cattgccagc ggcgtggccg tgtgcaaagt gctgcacctg 480
gaaggcgaag tgaacaagat caagtccgcc ctgctgtcca ccaacaaggc cgtggtgtcc 540
ctgagcaacg gcgtgagcgt gctgaccagc aaggtgctgg atctgaagaa ctacatcgac 600
aagcagctgc tgcccatcgt gaacaagcag agctgcagca tcagcaacat cgagacagtg 660
atcgagttcc agcagaagaa caaccggctg ctggaaatca cccgggagtt cagcgtgaac 720
gccggagtga ccacccccgt gtccacctac atgctgacca acagcgagct gctgtccctg 780
atcaatgaca tgcccatcac caacgaccag aaaaagctga tgagcaacaa cgtgcagatc 840
gtgcggcagc agagctactc catcatgtgc atcatcaaag aagaggtgct ggcctacgtg 900
gtgcagctgc ccctgtacgg cgtgatcgac accccctgct ggaagctgca caccagcccc 960
ctgtgcacaa ccaacaccaa agagggcagc aacatctgcc tgacccggac cgaccggggc 1020
tggtactgcg acaacgccgg cagcgtgtcc ttctttccac aggccgagac atgcaaggtg 1080
cagagcaacc gggtgttctg cgacaccatg aacagcctga ccctgccctc cgaagtgaac 1140
ctgtgcaacg tggacatctt caaccccaag tacgactgca agatcatgac ctccaagacc 1200
gacgtgtcca gctccgtgat cacctccctg ggcgccatcg tgtcctgcta cggcaagacc 1260
aagtgcaccg ccagcaacaa gaacagaggc atcatcaaga ccttcagcaa cggctgcgac 1320
tacgtgtcca ataagggcgt ggacaccgtg tccgtgggca acacactgta ctacgtgaat 1380
aagcaggaag gcaagagcct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gaactgctgt ccgccatcgg cggctacatc 1560
cccgaggccc ccagagatgg ccaggcctac gtgcggaagg acggcgagtg ggtgctgctg 1620
tctacatttc tgggcggcct ggtgcctaga ggctctcacc accaccatca ccacagcgcc 1680
tggtcccacc cccagttcga gaagtga 1707

<210> SEQ ID NO 45
<211> LENGTH: 1707
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
atggaactgc tgatcctgaa ggccaacgcc atcaccacca tcctgaccgc cgtgaccttc 60
tgcttcgcca gcggccagaa catcaccgag gaattctacc agagcacctg cagcgccgtg 120
agcaagggct acctgagcgc cctgcggacc ggctggtaca ccagcgtgat caccatcgag 180
ctgtccaaca tcaaagaaaa caagtgcaac ggcaccgacg ccaaagtgaa gctgatcaag 240
caggaactgg acaagtacaa gaacgccgtg accgagctgc agctgctgat gcagagcacc 300
cccgccacca acaacagagc cagaagagag ctgccccggt tcatgaacta caccctgaac 360
aacgccaaga aaaccaacgt gaccctgagc aagaagagaa agagaagatt cctgggcttc 420
ctgctgggcg tgggcagcgc cattgccagc ggcgtggccg tgtccaaagt gctgcacctg 480
gaaggcgaag tgaacaagat caagtccgcc ctgctgtcca ccaacaaggc cgtggtgtcc 540
ctgagcaacg gcgtgagcgt gctgaccttc aaggtgctgg atctgaagaa ctacatcgac 600
aagcagctgc tgcccatcct gaacaagcag agctgcagca tcagcaacat cgagacagtg 660
atcgagttcc agcagaagaa caaccggctg ctggaaatca cccgggagtt cagcgtgaac 720
gccggagtga ccacccccgt gtccacctac atgctgacca acagcgagct gctgtccctg 780
atcaatgaca tgcccatcac caacgaccag aaaaagctga tgagcaacaa cgtgcagatc 840
gtgcggcagc agagctactc catcatgagc atcatcaaag aagaggtgct ggcctacgtg 900
gtgcagctgc ccctgtacgg cgtgatcgac accccctgct ggaagctgca caccagcccc 960
ctgtgcacaa ccaacaccaa agagggcagc aacatctgcc tgacccggac cgaccggggc 1020
tggtactgcg acaacgccgg cagcgtgtcc ttctttccac aggccgagac atgcaaggtg 1080
cagagcaacc gggtgttctg cgacaccatg aacagcctga ccctgccctc cgaagtgaac 1140
ctgtgcaacg tggacatctt caaccccaag tacgactgca agatcatgac ctccaagacc 1200
gacgtgtcca gctccgtgat cacctccctg ggcgccatcg tgtcctgcta cggcaagacc 1260
aagtgcaccg ccagcaacaa gaacagaggc atcatcaaga ccttcagcaa cggctgcgac 1320
tacgtgtcca ataagggcgt ggacaccgtg tccgtgggca acacactgta ctacgtgaat 1380
aagcaggaag gcaagagcct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gaactgctgt ccgccatcgg cggctacatc 1560
cccgaggccc ccagagatgg ccaggcctac gtgcggaagg acggcgagtg ggtgctgctg 1620
tctacatttc tgggcggcct ggtgcctaga ggctctcacc accaccatca ccacagcgcc 1680
tggtcccacc cccagttcga gaagtga 1707

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 46

```
His His His His His His
1               5


<210> SEQ ID NO 47
<211> LENGTH: 488
<212> TYPE: PRT
<213> ORGANISM: Human respiratory syncytial virus

<400> SEQUENCE: 47

Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg Phe
            100                 105                 110

Leu Gly Phe Leu Leu Gly Val Gly Ser Ala Ile Ala Ser Gly Val Ala
        115                 120                 125

Val Ser Lys Val Leu His Leu Glu Gly Glu Val Asn Lys Ile Lys Ser
    130                 135                 140

Ala Leu Leu Ser Thr Asn Lys Ala Val Val Ser Leu Ser Asn Gly Val
145                 150                 155                 160

Ser Val Leu Thr Ser Lys Val Leu Asp Leu Lys Asn Tyr Ile Asp Lys
                165                 170                 175

Gln Leu Leu Pro Ile Val Asn Lys Gln Ser Cys Ser Ile Ser Asn Ile
            180                 185                 190

Glu Thr Val Ile Glu Phe Gln Gln Lys Asn Asn Arg Leu Leu Glu Ile
        195                 200                 205

Thr Arg Glu Phe Ser Val Asn Ala Gly Val Thr Thr Pro Val Ser Thr
    210                 215                 220

Tyr Met Leu Thr Asn Ser Glu Leu Leu Ser Leu Ile Asn Asp Met Pro
225                 230                 235                 240

Ile Thr Asn Asp Gln Lys Lys Leu Met Ser Asn Asn Val Gln Ile Val
                245                 250                 255

Arg Gln Gln Ser Tyr Ser Ile Met Ser Ile Ile Lys Glu Glu Val Leu
            260                 265                 270

Ala Tyr Val Val Gln Leu Pro Leu Tyr Gly Val Ile Asp Thr Pro Cys
        275                 280                 285

Trp Lys Leu His Thr Ser Pro Leu Cys Thr Thr Asn Thr Lys Glu Gly
    290                 295                 300

Ser Asn Ile Cys Leu Thr Arg Thr Asp Arg Gly Trp Tyr Cys Asp Asn
305                 310                 315                 320

Ala Gly Ser Val Ser Phe Phe Pro Gln Ala Glu Thr Cys Lys Val Gln
                325                 330                 335

Ser Asn Arg Val Phe Cys Asp Thr Met Asn Ser Leu Thr Leu Pro Ser
            340                 345                 350

Glu Val Asn Leu Cys Asn Val Asp Ile Phe Asn Pro Lys Tyr Asp Cys
```

-continued

```
        355                 360                 365

Lys Ile Met Thr Ser Lys Thr Asp Val Ser Ser Ser Val Ile Thr Ser
    370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Val Asp Thr Val Ser Val Gly Asn Thr Leu Tyr
            420                 425                 430

Tyr Val Asn Lys Gln Glu Gly Lys Ser Leu Tyr Val Lys Gly Glu Pro
        435                 440                 445

Ile Ile Asn Phe Tyr Asp Pro Leu Val Phe Pro Ser Asp Glu Phe Asp
    450                 455                 460

Ala Ser Ile Ser Gln Val Asn Glu Lys Ile Asn Gln Ser Leu Ala Phe
465                 470                 475                 480

Ile Arg Lys Ser Asp Glu Leu Leu
                485
```